US006664287B2

(12) United States Patent
Avery et al.

(10) Patent No.: US 6,664,287 B2
(45) Date of Patent: Dec. 16, 2003

(54) ANTIOXIDANTS

(75) Inventors: Mitchell Allen Avery, Oxford, MS (US); Harrihar A. Pershadsingh, Bakersfield, CA (US)

(73) Assignee: Bethesda Pharmaceuticals, Inc., Bakersfield, CA (US)

( * ) Notice: Subject to any disclaimer, the term of this patent is extended or adjusted under 35 U.S.C. 154(b) by 0 days.

(21) Appl. No.: 09/809,518

(22) Filed: Mar. 14, 2001

(65) Prior Publication Data

US 2002/0048798 A1 Apr. 25, 2002

Related U.S. Application Data

(60) Provisional application No. 60/189,514, filed on Mar. 15, 2000.

(51) Int. Cl.[7] ............... A61K 31/385; C07D 339/00
(52) U.S. Cl. ............... 514/436; 549/20; 549/21; 549/22
(58) Field of Search ............... 558/488; 549/20, 549/21, 22; 514/436

(56) References Cited

U.S. PATENT DOCUMENTS

| | | | | |
|---|---|---|---|---|
| 2,432,797 A | * | 12/1947 | Peters et al. | |
| 2,839,445 A | * | 6/1958 | Harris, Jr. | |
| 2,840,505 A | * | 6/1958 | Gruneit | |
| 2,842,590 A | * | 7/1958 | Wagner | |
| 2,872,455 A | * | 2/1959 | Bullock | |
| 2,877,235 A | * | 3/1959 | Hornberger, Jr. | |
| 2,933,430 A | * | 4/1960 | Rosenberg | |
| 2,961,448 A | * | 11/1960 | Reed et al. | |
| 3,049,549 A | * | 8/1962 | Reed et al. | |
| 3,132,152 A | * | 5/1964 | Ohara et al. | |
| 4,125,539 A | * | 11/1978 | Gastrock et al. | |
| 4,877,779 A | * | 10/1989 | Rzeszotarski et al. | 514/63 |
| 4,923,891 A | * | 5/1990 | Deason et al. | 514/433 |
| 4,966,732 A | * | 10/1990 | Giray et al. | |
| 5,296,505 A | * | 3/1994 | Solladie et al. | 514/436 |
| 5,334,612 A | * | 8/1994 | Kalden et al. | |
| 5,360,815 A | * | 11/1994 | Fortin et al. | 514/432 |
| 5,405,866 A | * | 4/1995 | Eliason et al. | 514/436 |
| 5,530,141 A | * | 6/1996 | Shen et al. | |
| 5,705,192 A | * | 1/1998 | Bethge et al. | |
| 5,990,153 A | * | 11/1999 | Wood et al. | |
| 6,046,228 A | * | 4/2000 | Rice et al. | |
| 6,284,786 B1 | * | 9/2001 | Casciari et al. | |
| 6,288,106 B1 | * | 9/2001 | Pearson et al. | |
| 6,313,164 B1 | * | 11/2001 | Fujita et al. | |
| 6,331,559 B1 | * | 12/2001 | Bingham et al. | |
| 6,353,011 B1 | * | 3/2002 | Pershadsingh et al. | |
| 6,365,622 B1 | * | 4/2002 | Cavazza | |
| 6,369,098 B1 | * | 4/2002 | Pershadsingh et al. | |
| 6,387,945 B2 | * | 5/2002 | Packer et al. | |
| 6,432,434 B1 | * | 8/2002 | Meyerhoff et al. | |

* cited by examiner

*Primary Examiner*—Deborah C. Lambkin

(57) ABSTRACT

This invention comprises administering to a human or animal in need of treatment an effective amount of an antioxidant lipoic acid derivative and/or pharmaceutically acceptable salts and solvates thereof for the treatment or prevention of pathological (inflammatory, proliferative and degenerative diseases, e.g. diabetes mellitus, atherosclerosis, Alzheimer's disease and chronic viral diseases) and non-pathological (e.g. skin aging and wrinkle formation) conditions caused by oxidative damage. Methods of synthesizing novel antioxidant lipoic acid derivatives and their use in preventing or treating diseases or conditions caused by oxidative stress and other free radical mediated conditions are described. Another aspect of this invention is the use of these antioxidant compositions for the protection of skin from damage caused by ultraviolet radiation and dessication, and to provide improved skin feel by desquamating, cleansing and clarifying the skin. The compositions described in this invention increase cellular viability of epidermal cells, promote cytoprotection, and decrease the production of inflammatory mediators such as inflammatory cytokines in these cells. The antioxidant compositions are incorporated into sunscreen products, soap, moisturizing lotions, skin toners, and other skin care products.

5 Claims, No Drawings

ANTIOXIDANTS

CROSS-REFERENCE TO RELATED APPLICATION

U.S. Provisional Application No. 60/189514 was filed for this invention on Mar. 15, 2000 for which the inventors claim domestic priority.

BACKGROUND OF THE INVENTION

α-lipoic acid (thioctic acid, 1,2-dithiacyclopentane-3-valeric acid, 1,2-dithiolane-3-pentanoic acid) is widely distributed in plants and animals in the form of the R-enantiomer; it acts as coenzyme in many enzymatic reactions, constitutes a growth factor for a number of bacteria and protozoa and is used in death-head fungus poisoning. Lipoic acid (1,2-dithiolane-3-pentanoic acid) is a naturally occurring compound. It is a component of mitochondrial multienzyme complexes which dehydrogenates α-keto acids (e.g. pyruvate). In pathological conditions, lipoic acid is applied in the treatment of diabetic polyneuropathy, liver cirrhosis and metal intoxications. Particularly in diabetic polyneuropathy, the antioxidant activity of lipoic acid is considered to contribute to its therapeutic effect.

One aspect of this invention relates to the uses of optical isomers of the novel lipoic acid-related thiazolidinedione and phenyl acetic acid derivatives of the instant invention. In the case of the purely optical isomers of α-lipoic acid (R- and S-form, i.e. R-α-lipoic acid and S-α-lipoic acid), unlike the racemate (Biewenga et al. "An overview of lipoate chemistry." In: Lipoic Acid in Health and Disease. (Fuchs J, Packer L, Zimmer G, eds.), Marcel Dekker, Inc. 1997, pp 1–32), the R-enantiomer mainly has an anti-inflammatory activity, for example, being stronger by a factor of 10 than that of the racemate (Ulrich et al. U.S. Pat. No. 5,728,735 Mar. 17, 1998), and has been shown to have superior insulin-sensitizing activity and to confer improved cardiac function (Zimmer G et al. J Mol Cell Cardiol. 27:1895–903 (1995)) and ameliorate diabetic peripheral and autonomic neuropathy (Ziegler D, Gries F A. Diabetes. 46 Suppl 2:S62–6 (1997)). In contrast, the S-enantiomer has been shown to be more effective as an anti-nociceptive agent. The anti-nociceptive (analgesic) activity of the S-enantiomer is for example stronger by a factor of 5 to 6 than that of the racemate (Ulrich et al. U.S. Pat. No. 5,728,735 Mar. 17, 1998). Accordingly, the R- and S-enantiomers of the novel lipoic acid-related thiazolidinedione and phenyl acetic acid derivatives are considered to have superior efficacy in the treatment of specific diseases. For example, a particular stereoisomer, e.g. R-(+)-α-lipoic stereoisomeric thiazolidinedione derivative is expected to have superior anti-inflammatory activity whereas the corresponding optical isomers are expected to provide greater efficacy in the treatment of other diseases. In addition, the α-lipoic acid racemate and R and S isomeric forms display anti-inflammatory, anti-nociceptive (analgesic) and cytoprotective properties.

The metabolism of lipoic acid has been studied in Pseudomonas (Furr et al., Arch. Biochem. Biophys. 185:576–583 (1978)) and in rats (Spence et al., Arch. Biochem. Biophys. 174:13–19 (1976); Gal et al., Arch. Biochem. Biophys. 89:253–261 (1960); Harrison et al., Arch. Biochem. Biophys. 160:514–522 (1974)). It has been found that in these species lipoic acid is converted by beta oxidation of its pentanoic acid side chain. Regarding the antioxidant activity of lipoic acid, it has been proposed that reduction of lipoic acid to dihydrolipoic acid is an important step in its therapeutic effect.

Free Radical Formation, Oxidative Stress and Skin Damage

Natural aging of skin and exposure of skin ultraviolet (UV) wavelengths of sunlight can cause sunburn (erythema) and blistering (edema). Exposure to ultraviolet light can also cause the skin to feel dry and taut in moderate doses, and to peel if exposed to higher doses. These short term effects are readily perceptible and triggered by UV-induced formation of free radical, particularly activated oxygen radicals. Other more subtle effects that are not as readily discernable, but also involving free radical formation, such as photo-immunosuppression, cross-linking of deoxyribonucleic acid (DNA), formation of sunburn cells, and loss of Langerhans cells. Moreover, cross-linking of collagen, elastin, laminin and other extracellular matrix proteins, activation of matrix metalloproteinases (MMPs) and inhibition of tissue inhibitors of MMPs (TIMPS) result in the destruction, thinning and dessication of the extracellular matrix leading to the typical appearance of aged skin. The more serious long term effects can occur such as premature aging of the skin, actinic keratosis (a pre-cancerous condition) and frank skin cancer can ultimately develop.

Human skin can be protected from some of these environmental effects. Moisturizers can readily reverse the appearance of dryness regardless of whether it results from low humidity conditions or UV light, and relieve the tautness of the skin caused by UV light and the flaccidity and dryness caused by the aging process. These products either attract moisture from the environment to the skin's surface, or reduce the amount of moisture in the skin that can escape into the environment. These products also add needed moisture to the skin from the formulation itself, and add a layer of emollients on the skin surface to leave it softer and more supple.

Sunscreen products are known to protect the skin from some of the harmful effects of UV exposure. These products contain molecules that absorb the harmful wavelengths of ultraviolet light before they can reach the skin. The absorbed light is converted to heat and rapidly dissipated to the skin and environment, which allows these molecules to revert to a lower energy state, and subsequently absorb another photon of light. In this manner, sunscreen agents can absorb numerous photons of ultraviolet light in a relatively short period of time. By absorbing the harmful wavelengths of light, sunscreen products prevent many of the acute and chronic effects caused by ultraviolet light.

However, sunscreen products are not perfect in their mode of action. There is no single sunscreen agent that is capable of absorbing all of the harmful wavelengths striking the skin. Higher Sun Protection Factor (SPF) formulations address this problem by including a combination of sunscreen agents in the formulation. However, even when using a combination of sunscreen agents, these products do not provide complete protection, particularly from the longer ultraviolet wavelengths. Although these longer wavelengths do not readily elicit many of the acute damaging effects commonly attributed to ultraviolet light exposure, recent research indicates that these wavelengths can create free radicals in the skin. These free radicals may be responsible for the premature aging of the skin commonly linked to ultraviolet light exposure.

According to the free radical theory of premature aging of the skin, ultraviolet light can produce reactive oxygen species (ROS) that damage the skin. ROS are a collection of reactive free radicals produced from the oxygen molecule, and include singlet oxygen, the superoxide radical, hydrogen peroxide, and the hydroxyl radical, as well as the reaction products produced by these free radicals. Due to their reactivity, ROS relatively indiscriminately react with other molecules, and generate a cascade of harmful free radical reactions in the skin.

The skin possesses defense mechanisms against the generation of ROS. These defenses include the presence of enzymes such as superoxide dismutase, catalase, glutathione transferase, glutathione peroxidase and glutathione reductase, as well as antioxidants such as tocopherols, ubiquinone, ubiquinol, ascorbic acid and dehydroascorbic acid. Unfortunately, ultraviolet light entering the skin can easily overwhelm these defense systems, such that the amount of superoxide dismutase and glutathione transferase in the skin declines significantly upon irradiation with solar simulated ultraviolet light. Simultaneous with the loss of these reducing enzymes, there is a dramatic increase in conjugated double bonds formed in the skin from the linoleates present in cell membranes. There is also an increase in thiobarbituric acid reactive substances present in the skin, which represent a collection of molecules that are formed from ROS.

Prostaglandins, inflammatory interleukins are and other mediators of inflammation that are believed to be produced concomitant to ROS production and the kind of skin damage described above may create conditions that promote the formation of prostaglandins and sunburn cells. These mediators of inflammation are formed from arachidonic acid upon oxidation via the lipoxygenase pathway, and by free radical-induced (e.g. superoxide-induced) activation of nuclear factors, such as NF-κB, AP-1 and NFAT, that promote the expression of inflammatory cytokines. Additionally, there are other messenger systems in skin cells that could increase the amount of prostaglandins, inflammatory interleukins and other mediators that are activated by reactions involving ROS. For a comprehensive discussion of antioxidants and ROS in health and disease, see: "Antioxidants in Health and Disease", Eds; Basu T. K et al, CABI Publishing, United Kingdom, 1999. Sunburn cells are prematurely dead keratinocytes that are produced in skin as a result of ultraviolet light exposure. The contribution of ROS to the formation of sunburn cells has not been adequately researched. However, given the fact that ROS produce negative effects upon molecules in the cell membranes as well as in proteins including enzymes that control most cellular activity, it has been suggested that ROS could play a potentially important role in the formation of sunburn cells.

Since sunscreens are unable to completely protect the skin against the adverse effects of ultraviolet radiation, additional and alternative modes of protection have been proposed. Vitamins, such as Vitamin E acetate and succinate, have been shown to make the skin softer and smoother after topical application, which can offset some of the damaging effects of the sun. Vitamin A palmitate has been shown to create smoother skin and help enhance the process of cellular turnover. This enhancement rids the skin of the outermost dead layer of skin by bringing more youthful appearing skin cells to the surface. Other materials, such as hyaluronic acid and pyrrolidone carboxylic acid (PCA), have also been used for their ability to enhance the moisture binding capacity of the skin and therefore lead to smoother, softer skin.

Compositions that incorporate Vitamins A or E, or their derivatives, in sunscreen compositions, are shown in U.S. Pat. Nos. 4,454,112; 5,532,805; and 5,378,461. The use of Vitamin C in combination with Vitamins A, E, B and other agents in a skin protectant composition, is described in U.S. Pat. No. 4,938,960. An antioxidant preparation that is said to protect the skin against harmful ultraviolet radiation is disclosed in U.S. Pat. No. 5,607,921, and contains Vitamin C, in combination with Vitamins A and E, and monosaccharide or amide precursors. Sunscreen compositions containing panthenol and other agents are disclosed in U.S. Pat. Nos. RE 33,845; 5,505,935; 5,445,823; and 5,573,754. The antioxidant effect of superoxide dismutase when externally applied to the skin to protect against the effects of ultraviolet radiation is also described in U.S. Pat. No. 5,601,806.

In spite of advances in recent years in the protection of skin from harmful ultraviolet radiation, the epidemic of skin cancer and skin damage from the effects of this radiation has continued unabated. The loss of portions of the ozone layer from environmental pollution is believed to have contributed to an increase in ambient ultraviolet radiation that reaches exposed skin. Many skin protection preparations that could prevent sun damage have an unacceptable odor or texture that discourages their more frequent use, and many of the available skin protectants do not sufficiently protect the skin from these many mechanisms of injury. Hence there is a significant public health need for commercially acceptable or improved preparations that can be topically applied to human and animal skin, to offset the harmful effects of ultraviolet radiation.

It is therefore an object of the invention to provide a therapeutic or cosmetic composition containing new antioxidants, or agents that reduce sun induced skin damage and inflammation by aborting the production of inflammatory mediators and production of ROS in the skin.

It is another object of the invention to provide such a composition having a superior therapeutic or cosmetic effect. Yet another object is to provide such compositions that have characteristics that will encourage their use.

SUMMARY OF THE INVENTION

The present invention relates to pharmaceutical compositions or salts and solvates thereof, containing isolipoic acid, R-α-lipoic acid, S-α-lipoic or their derivatives, as an active ingredient. The compositions are useful because they inhibit, for example, inflammatory and proliferative processes, and oppose or ameliorate the oxidative stress imposed on organismal physiological processes, including the mediation of cytoprotective effects on cells, resulting in improved cell health and survival. Another aspect of this invention extends to metabolites of α-lipoic acid, including but not limited to 3-keto-lipoic acid, racemic dihydrolipoic acid, racemic lipoamide, and their optical isomers, R and S optical isomers.

Differences exist between the optical isomers of α-lipoic acid compared to the racemate, (DL)-lipoic acid. The R-enantiomer acts mainly as an anti-inflammatory and the S-enantiomer mainly as an analgesic, the optical isomers of α-lipoic acid being a number of times stronger (for example by at least a factor of 5) than the racemate of .α-lipoic acid. It has surprisingly been found that, in the case of the purely optical isomers of α-lipoic acid (R- and S-form, i.e. R-α-lipoic acid and S-α-lipoic acid), unlike the racemate, the R-enantiomer mainly has an anti-inflammatory activity, for example, being stronger by a factor of 10 than that of the racemate. The R-enantiomer has been shown to have insulin-sensitizing activity and improve diabetes-related organ damage, in particular diabetic neuropathy. In contrast, the S-enantiomer has been shown to be more effective as an anti-nociceptive agent. The anti-nociceptive (analgesic) activity of the S-enantiomer is for example stronger by a factor of 5 to 6 than that of the racemate. The enantiomers therefore constitute very much more specific and stronger acting active substances than the racemate.

Therefore, one aspect of the present invention provide improved pharmaceutical compositions which have, in particular, analgesic and anti-inflammatory activity. The invention relates to pharmaceutical compositions containing as active ingredient either R-α-lipoic acid or S-α-lipoic acid (i.e. the optical isomers of α-lipoic acid or derivatives thereof) or isolipoic acid or derivatives thereof, or a pharmaceutically acceptable salt of these compounds, their preparation and their use for the preparation of appropriate pharmaceutical and cosmeceutical compositions. These are particularly suitable for combating pain and inflammation. In another aspect of this invention, a cytoprotective activity is also obtained.

The amounts by weight set out herein relate, in each case, to the purely optical isomers of α-lipoic acid derivatives where applicable, i.e. not to the salts. When salts are used, the appropriate amounts must correspond in each case to the amounts of the free acid and be increased according to the gram-molecular weight of the salt.

This invention comprises the synthesis of novel synthetic lipoic acid derivatives and compositions thereof, and their use cosmetic, nutritional and pharmaceutical uses. The subject invention relates to compositions for oral, intravenous, intradermal, subcutaneous, intramuscular or topical application. Oral delivery is the preferred method of administration for most nutritional and pharmaceutical uses. For example, compounds described in this invention are administered orally as are anti-oxidant vitamins (e.g. vitamin C or vitamin E) or vitamin-like substances (e.g. flavonoids such flavones, isoflavones and polyphenols). In another aspect, these pharmaceutical compositions have a cytoprotective activity and are suitable for combating pain and inflammation.

In another aspect of this invention, the synthetic lipoic acid derivatives described in the instant invention are useful for systemic administration for use in the treatment of free radical mediated diseases, including inflammatory, proliferative, neurodegenerative, metabolic and infectious diseases and complications thereof. For example, in the case of diabetes mellitus, the related complications include diabetic nephropathy, diabetic retinopathy, atherosclerosis, ischemic heart disease, dyslipidemia, atherogenesis, thrombosis, and endothelium-related and inflammatory dysfunctions in diabetes. A description of diseases treatable with compounds described in this invention, see Tables I through VII.

In another aspect of this invention, these compositions are also useful for conditioning desquamating, and cleansing the skin and for relieving dry skin. These compositions can be in the form of leave-on products or products that are rinsed or wiped from the skin after use. The composition contains certain active ingredients including at least one cyclic polyanionic polyols, and/or at least one zwitterionic surfactant. Topical, intradermal, subcutaneous, intramuscular delivery are preferred methods of administration for most cosmetic uses, including their use in preventing skin aging and wrinkle formation, improving skin turgor and elasticity, improving or eliminating wrinkles, and improving the feel and visual appearance of skin, especially human facial skin. In a particular embodiment, the composition includes an antioxidant lipoic acid derivative in combination with other antioxidant species such as panthenol, grape seed extract, vitamin C, vitamin E, vitamin A or other retinoid, and superoxide dismutase, which exhibit a synergistic effect in protecting the skin from the adverse effects of dessication, aging and ultraviolet radiation.

TECHNICAL FIELD AND BACKGROUND OF COSMETIC USE

The compositions of the present invention are useful for topical application to human skin and for systemic (oral) use in mammals, including humans. The preferred method of delivery is topical application to the skin. These compositions provide improved skin feel, and can be in the form of leave-on products or products that are rinsed or wiped from the skin after use. These compositions are also useful for conditioning the skin, for desquamating the skin, for cleansing and clarifying the skin, for reducing skin pore size, and also for relieving dry skin.

The treatment of human skin with various agents has been undertaken for many years with the goal being to keep the skin clean and in a smooth and supple condition. Skin has the tendency to dry out when exposed to low humidity or to harsh detergent solutions for extended periods of time. From a physiological standpoint, dryness is a measure of the water content of the skin. Under normal conditions, the water content and vapor pressure of the skin are higher than those of the surrounding air, with consequent evaporation of water from the skin's surface. Skin becomes dry because of excessive loss of water from its surface, which results in loss of water from the stratum corneum. Low humidity speeds up this process, exacerbating the drying of skin. Also, continuous and prolonged contact with or immersion in soap or detergent solutions can contribute to dryness of the stratum corneum. The reason for this is that these solutions promote dissolution of the skin surface and lipids, and the dissolution of the hygroscopic water-soluble components of the skin. Also, in normal skin, the stratum corneum is shed as individual cells or as small clusters of cells.

Skin problems such as dry skin, psoriasis, ichthyosis, dandruff, acne, callus, photodamaged skin, aged skin, and sunburn can be described as disorders of keratinization in which the shedding of stratum corneum cells at the skin surface is altered relative to normal, young, healthy skin. Such alteration results in shedding of large clusters of cells leading to visible scaling of the skin, a build-up of keratinaceous material on the surface or in follicles or ducts, and a rough texture to the skin surface. These conditions can be improved by removal of the outermost keratinaceous material. In other words, by desquamation. Additionally there is an ongoing need to effectively deliver a wide variety of active ingredients to the skin, either via direct application of such a composition, or in the case of a cleansing composition, via the cleansing process.

Therefore, there is a need for topical skin care compositions which give the skin a smooth and elegant skin feel, which are useful for treating dry skin, and which are useful for providing a desquamation benefit. There is also a need for providing cleansing products have these attributes. There is also a need for composition which are also useful for delivering a wide variety of active ingredients to the skin, either directly to the skin or during the cleansing process.

In the present invention skin care compositions containing a combination of amphoteric surfactants, anionic surfactants, and cationic surfactants are useful for providing these skin care benefits. It is therefore an object of the present invention to provide skin care compositions for topical application to the skin. It is another object of the present invention to provide skin care compositions having improved skin conditioning properties, and which are also mild and nonirritating to the skin.

It is another object of the present invention to provide skin care compositions which improve skin dryness and which give the skin a smooth, soft, silky feel.

It is another object of the present invention to provide skin care compositions which are useful delivering a wide variety of active ingredients to the skin.

It is another object of the present invention to provide skin care compositions, which, when in the form of cleansing compositions, are useful for delivering a wide variety of active ingredients to the skin via the cleansing process.

It is another object of the present invention to provide methods for treating the skin of humans of all ages.

It is another object of the present invention to make skin feel soft and smooth, especially wrinkled skin, aged skin, dry skin, as a result of aging, weathering, exposure to physical insult (e.g. dessication, sunlight, UV radiation in sunlight), chemical insult (e.g. dehydration from excessive washing, caustic solvents).

It is another object of the present invention to provide methods for cleansing the skin, for clarifying the skin, for reducing skin dryness, for reducing pore size, and for delivering active ingredients to the skin.

DETAILED DESCRIPTION OF THE INVENTION

This invention comprises the synthesis of novel synthetic lipoic acid derivatives and compositions thereof, and their use cosmetic, nutritional and pharmaceutical uses. The subject invention relates to compositions for oral, intravenous, intradermal, subcutaneous, intramuscular or topical application. Oral delivery is the preferred method of administration for most nutritional and pharmaceutical uses. For example, compounds described in this invention are administered orally as are anti-oxidant vitamins (e.g. vitamin C or vitamin E) or vitamin-like substances (e.g. flavonoids such flavones, isoflavones and polyphenols). Topical, intradermal, subcutaneous, intramuscular delivery are preferred methods of administration for most cosmetic uses, including their use in preventing skin aging and wrinkle formation, improving skin turgor and elasticity, improving or eliminating wrinkles, and improving the feel and visual appearance of skin, especially human facial skin.

In another aspect of this invention, these compositions are also useful for conditioning desquamating, and cleansing the skin and for relieving dry skin. These compositions can be in the form of leave-on products or products that are rinsed or wiped from the skin after use. The composition contains certain active ingredients including at least one cyclic polyanionic polyols, and/or at least one zwitterionic surfactant. In another aspect, these pharmaceutical compositions have a cytoprotective activity and are suitable for combating pain and inflammation.

In another aspect of this invention, the natural and synthetic lipoic acid derivatives and their metabolites as described in the instant invention are useful for systemic administration for use in preventing skin aging and in the treatment of free radical mediated diseases, including inflammatory, proliferative, neurodegenerative, metabolic and infectious diseases and the complications. For example, in the case of diabetes mellitus, the related complications include diabetic nephropathy, diabetic retinopathy, atherosclerosis, ischemic heart disease, dyslipidemia, atherogenesis, thrombosis, and endothelium-related and inflammatory dysfunctions in diabetes (see Tables I through VII).

Salt formers that may be considered for R-α-lipoic acid and S-α-lipoic acid are, for example, conventional bases or cations which are physiologically acceptable in the salt form. Examples include: alkali metals or alkaline earth metals, ammonium hydroxide, basic amino acids such as arginine and lysine, amines having the formula NR1, R2, R3 in which the radicals R1, R2, and R3 are the same or different and represent hydrogen, C1, -C4, -alkyl or C1, -C4, -oxyalkyl, such as mono- and diethanolamine, 1-amino-2-propanol, 3-amino-1propanol; alkylene diamine with an alkylene chain consisting of 2 to 6 carbon atoms, such as ethylenediamine or hexamethylene tetramine, saturated cyclic amino compounds having 4–6 ring carbon atoms such as piperidine, piperazine, pyrrolidine, morpholine; N-methylglucamine, creatine, tromethamine.

ADMINISTRATION

The therapeutic compound is optionally administered topically by the use of a transdermal therapeutic system (see, Barry, *Dermatological Formulations*, (1983) p. 181 and literature cited therein). While such topical delivery systems have been designed largely for transdermal administration of low molecular weight drugs, by definition they are capable of percutaneous delivery. They can be readily adapted to administration of the therapeutic compounds of the invention by appropriate selection of the rate-controlling microporous membrane.

For ophthalmic applications (Table VII), the therapeutic compound is formulated into solutions, suspensions, and ointments appropriate for use in the eye. The concentrations are usually as discussed above for topico-local preparations. For ophthalmic formulations, see Mitra (ed.), *Ophthalmic Drug Delivery Systems*, Marcel Dekker, Inc., New York, N.Y. (1993) and also Havener, W. H., Ocular Pharmacology, C. V. Mosby Co., St. Louis (1983). The therapeutic compound is alternatively administered by aerosol. This is accomplished by preparing an aqueous aerosol, liposomal preparation or solid particles containing the compound. A nonaqueous (e.g., fluorocarbon propellent) suspension could be used. Sonic nebulizers are preferred because they minimize exposing the therapeutic compound to shear, which can result in degradation of the compound.

Ordinarily, an aqueous aerosol is made by formulating an aqueous solution or suspension of the therapeutic compound together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

For oral administration, either solid or fluid unit dosage forms can be prepared. For preparing solid compositions such as tablets, the compound of interest is mixed into formulations with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound of interest with an inert pharmaceutical diluent and filling the mixture into a hard gelatin capsule of appropriate size. Soft gelatin capsules are prepared by machine encapsulation of a slurry of the compound of interest with an acceptable vegetable oil, light liquid petrolatum or other inert oil. Fluid unit dosage forms for oral administration such as syrups, elixirs and suspensions can be prepared. The water soluble forms can be dissolved in an aqueous vehicle together with sugar, aromatic flavoring agents and preservatives to form a syrup. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Slow or extended-release delivery systems, including any of a number of biopolymers (biological-based systems), systems employing liposomes, and polymeric delivery systems, can be utilized with the compositions described herein to provide a continuous or long term source of therapeutic compound. Such slow release systems are applicable to formulations for topical, ophthalmic, oral, and parenteral use.

The single dose of active ingredient of may for example be:
a) in the oral medicinal form between 100 mg–3 g, preferably 200 mg–1 g.
b) in parenteral medicinal forms (for example intravenous, intramuscular) between 100 mg–12 g, preferably 200 mg–6 g.
c) in medicinal forms for inhalation (solutions or aerosols) between 100 mg–2 g, preferably 200 mg–1 g.
d) in medicinal forms for rectal or vaginal application between 100 mg–2 g, preferably 200 mg–1 g. The doses according to a) to d) may for example be administered 1 to 6 times, preferably 1 to 4 times daily or, however, as a permanent infusion, for example with the aid of an infusoniate, i.e., with an infusion apparatus for accurate hourly dosage of an active substance in solution.

The daily dose of a lipoic acid derivative in humans should for example be between 70–80 mg per kg weight; the single dose for example 16–20 mg per kg body weight, this dose appropriately being given 4 times daily: the pharmaceutical compositions therefore preferably contain 1–1.5 g of the lipoic acid derivative in a pharmaceutical formulation, a dose of this type preferably being given 4 times each day.

The recommended treatment is, for example, 3 times daily, 1 to 4 tablets with a content of 50 mg to 2 g of active ingredient per tablet, or, for example, in intravenous injection 1 to 4 times daily, one ampoule/infusion bottle of 1 to 500 ml content with 200 mg to 6 g of active ingredient. In the case of oral administration the minimum daily dose is for example 300 mg; the maximum daily dose, given orally, should not exceed 12 g.

The dose amounts mentioned refer, in each case, to the free acids R- or S-α-lipoic acid derivative. Should these be used in the form of their salts, the quoted dosages/dosage ranges should be increased in accordance with the higher molecular weight of the salts. The formulations/products of the invention may preferably also contain additional vitamins, in particular vitamin B1 and/or vitamin E.

For the treatment of disorders caused by retroviruses, in particular HIV viruses, appropriate pharmaceutical compositions should contain such an amount of R- or S-lipoic acid or a lipoic acid derivative, this should be administered in such an amount, that single or repeated application achieves in the body a level of activity between 3.5 and 200 mg/kg, preferably 7 and 100 mg, in particular between 35 and 70 mg/kg body weight.

For the analgesic activity the general dose range of S-α-lipoic acid that may be considered is, for example: 1–100 mg/kg orally. For the anti-inflammatory and cytoprotective activity the general dose range of R-α-lipoic acid that may be considered is, for example: 1–100 mg/kg orally.

Apart from its anti-nociceptive (analgesic) main activity, S-α-lipoic acid or respective derivative also possesses an anti-inflammatory and cytoprotective activity, however to a lesser extent. In addition to the main anti-inflammatory and anti-arthritic activity, R-α-lipoic acid also has anti-nociceptive and cytoprotective activity, albeit to a lesser extent.

The optical isomers of α-lipoic acid or isolipoic acid or derivative thereof display a good analgesic, anti-inflammatory, anti-proliferative, anti-artherosclerotic, anti-atherogenetic, anti-restenotic, anti-vasuloocclusive and cytoprotective activity in, for example investigative models of these diseases. Indications that may for example be considered are described in Table I through VII, including inflammatory, degenerative articular and extra-articular rheumatic disorders, non-rheumatic states of inflammation and swelling, Arthrosis deformans, chondropathies, periarthritis, inflammatory and non-inflammatory skin disorders such as for example neurodermitis and psoriasis, inflammatory and non-inflammatory disorders of the gastro-intestinal tract, such as for example gastritis, Ulcus ventriculi, ileitis, duodenitis, jejunitis, colitis, polyneuropathy of diabetogenic, alcoholic, hepatic and uraemic origin, degeneration of the liver parenchyma, hepatitis, fatty liver and fatty cirrhosis as well as chronic liver disorders, inflammatory respiratory tract disorders, such as bronchial asthma, sarcoidosis, ARDS (acute respiratory distress syndrome).

The daily doses of the dosage forms of the invention for analgesic or cytoprotective or anti-inflammatory activity are, for example, 0.1 to 600 mg, preferably 15 to 400 mg and in particular 50 to 200 mg of R-α-lipoic acid or S-α-lipoic acid or isolipoic acid derivative. In accordance with the invention the optical isomers of α-lipoic acid (R- or S-form in each case) are given in a daily dose of 10–600 mg, for example of 25 to 400 mg or 10 to 200 mg. The maximum daily dose for the cytoprotective activity and for the treatment of pain and inflammation should not exceed 600 mg. The daily doses may be given in the form of a single administration of the total amount or in the form of 1 to 6, in particular 1–4, partial doses per day. In general an administration of 1–4 times, in particular 1–3 times daily is preferred.

For example the preferred daily dose of lipoic acid or lipoic acid derivative is preferably 80 mg for the parenteral form of application and 200 mg for the oral form dosed once or twice daily. In particular, the daily dose for the parenteral form of application is 100 mg or 200 mg for the oral form. The pharmaceutical compositions are preferably administered orally but may also be administered parenterally (intravenously, intraarticularly, intramuscularly, subcutaneously, intradermally), or delivered or applied in the form of a solution, suspension, gel, lotion, ointment or other suitable delivery vehicle topically, directly to the skin, intraorally, sublingually, as an inhalation, or per rectum, or per vagina directly applied or as a suppository.

Pharmaceutical compositions containing compounds described in this invention as active ingredient may for example be formulated in the form of tablets, capsules, pills or coated tablets, granulates, pellets, plasters, solutions or emulsions, the active ingredient in each case optionally being combined with appropriate auxiliary and carrier substances. In the case of solutions, these contain for example 0.5 to 20% by weight, preferably 1 to 10% by weight of one of the optical isomers of α-lipoic acid (in each case either the iso-form or R-form or S-form or derivative thereof).

The dosage unit of the pharmaceutical composition with the optical isomers of α-lipoic acid or a therapeutically useful salt thereof (in each case either the R-form or the S-form) may, for example, contain:

a) in the case of oral medicinal forms: 10 to 600 mg, preferably 20 to 400 mg, in particular 50 to 200 mg of the compound. The doses may for example be given 1 to 6 times, preferably 1 to 4 times, in particular 1 to 3 times daily. In each case, however, a total dosage of 600 mg per day should not usually be exceeded for the cytoprotective activity and for the treatment of pain and inflammation. The same also applies to the following medicinal forms listed under b) to e).

b) in the case of parenteral medicinal forms (for example intravenous, intramuscular or intra-articular): 10 to 300 mg, preferably 15 to 200 mg, in particular 20 to 100 mg of the compound. The doses may, for example, be given 1 to 6 times, preferably 1 to 4 times, in particular 1 to 3 times daily.

c) in the case of medicinal forms for application to the skin and mucous membranes (for example as solutions, lotions, emulsions, ointments, plasters and the like): 10 to 500 mg of the compound, preferably 40 to 250 mg, in particular 50 to 200 mg. These doses may for example be administered 1 to 6 times, preferably 1 to 4 times, in particular 1 to 3 times daily.

d) in the case of medicinal forms for inhalation (solutions or aerosols): 0.1 to 300 mg, preferably 0.25 to 150 mg, in particular 0.5 to 80 mg of a compound described herein. These doses may, for example, be administered 1 to 6 times, preferably 1 to 4 times, in particular 1 to 3 times daily.

Should lotions be used, the compounds are preferably used in the form of a salt. It is of course also possible to prepare pharmaceutical formulations which contain 2 to, for example, 6 times the above mentioned dosage units. In particular the tablets or capsules contain 20 to 500 mg, pellets, powders or granulates 20 to 400 mg, suppositories 20 to 300 mg of a compound of the instant invention.

The above mentioned dosages always relate to the free optical isomers of α-lipoic acid and lipoic acid derivatives as described in this invention. Should the optical isomers of these compounds be used in the form of a salt, the dosages/dosage ranges should be correspondingly increased due to the higher molecular weight.

COMPOSITIONS/FORMULATIONS FOR TOPICAL ADMINISTRATION

The compositions of the present invention are useful for application to human skin. These compositions are useful for conditioning the skin, for desquamating the skin, for treating dry skin, for delivering active ingredients to the skin, and in the cleansing embodiments, for cleansing the skin without over-drying or irritating the skin.

Without being limited by theory it is believed that the amphoteric surfactant of these compositions can potentially complex with both the anionic and cationic surfactant components. Additionally, the anionic surfactant can potentially complex with the cationic surfactant component. These multiple complexes tend to be viscous and lubricious leading to a soft or smooth, elegant skin feel. These complexes are also believed to be highly stable relative to the individual surfactant components. These complexes are useful for aiding in the delivery to the skin of any active ingredients which can be present in the compositions. In the case of a cleansing composition, these complexes tend to deposit out from the composition, thereby helping to carry any active ingredients to the skin's surface, while leaving a soft, smooth skin feel. Because the postulated complexes can contain various combinations of amphoteric, anionic, and cationic surfactants, these complexes are also effective for cleansing the skin and for promoting the desquamation process. Because the charges on the individual surfactants are complexed, the surfactants are tendered less harsh and irritating to the skin versus the free surfactants.

The compositions of the present invention can be formulated into a wide variety of product types including, but not limited to creams, lotions, mousses, sprays, "rinse-off" cleansers, "water-less" cleansers, bars, gels, and the like. The term "rinse", as used herein, means that the composition is in a form that can be used in a cleansing process whereby the composition is ultimately rinsed or washed from the skin with water to complete the cleansing process. The term "water-less", as used herein, means that the composition is in the form that can be used in a cleansing process without water whereby the composition is typically removed by wiping with a device such as a cotton ball, a cotton pad, a tissue, a towel, and the like.

The term "pharmaceutically-acceptable," as used herein, means that the compositions and components thereof so described are of sufficiently high purity and are suitable for use in contact with human skin and tissues without undue toxicity, irritation, incompatibility, instability, allergic response, and the like.

The term "pharmaceutically-acceptable salts," as used herein means any of the commonly-used salts that are suitable for use in contact with human skin and tissues without undue toxicity, irritation, incompatibility instability, allergic response, and the like.

Amphoteric Surfactant

The composition of the present invention comprise from about 0.1% to about 20%, more preferably from about 0.2% to about 10%, and most preferably from about 0.5% to about 5% of an amphoteric surfactant. The term "amphoteric surfactant," as used herein, is also intended to encompass zwitterionic surfactants, which are well known to formulators skilled in the art as a subset of amphoteric surfactants.

A wide variety of amphoteric surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radical contains an ionizable water solubilizing group, e.g., carboxy, sulfonate, sulfate, phosphate, or phosphonate. Nonlimiting examples of amphoteric surfactant useful in the compositions of the present invention are disclosed in McCutcheon's, Detergents and Emulsifiers, North American edition (1986), published by allured Publishing Corporation; and McCutcheon's, Functional Materials, North American Edition (1992); both of which are incorporated by reference herein in their entirety.

Preferred amphoteric or zwitterionic surfactants are the betaines, sultaines, and hydroxysultaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, stearyl betaine, lauryl dimethyl sulfoethyl betaine, lauryl bis-(2-hydroxyethyl) sulfopropyl betaine, and amidobetaines and amidosulfobetaines (wherein the RCONH(CH2)3 radical is attached to the nitrogen atom of the betaine), oleyl betaine (available as amphoteric Velvetex OLB-50 from Henkel), and cocamidopropyl betaine (available as Velvetex BK-35 and BA-35 from Henkel). Examples of sultaines and hydroxysultaines include materials such as cocamidopropyl hydroxysultaine (available as Mirataine CBS from Rhone-Poulenc).

Preferred for use herein are amphoteric surfactants produced according to the teaching of U.S. Pat. No. 5,607,980 Mar. 4, 1997 and U.S. Pat. No. 5,821,237 Oct. 13, 1998. Preferred amphoteric surfactants of the present invention include cetyl dimethyl betaine, cocoamidopropyl betaine, stearyl dimethyl betaine, and cocoamidopropyl hydroxy sultaine. Still more preferred are cetyl dimethyl betaine, stearyl dimethyl betaine, and cocamidopropyl betaine. Most preferred is cetyl dimethyl betaine.

Examples of other useful amphoteric surfactants are alkyliminoacetates, and iminodialkanoates and aminoalkanoates according to the teaching of U.S. Pat. No. 5,821,237 Oct. 13, 1998. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072 which is incorporated herein by reference in its entirety; N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include phosphates, such as coamidopropyl PG-dimonium chloride phosphate (commercial available as Monaquat PTC, from Mona Corp.).

Anionic Surfactant

The compositions of the present invention comprise from about 0.1% to about 20%, more preferably from about 0.2% to about 10%, and most preferably from about 0.5% to about 5% of an anionic surfactant. Nonlimiting examples of anionic surfactants useful in the compositions of the present invention are disclosed in McCutcheon's, Detergents and Emulsifiers, North American edition (1986), published by allured Publishing Corporation; McCutcheon's, Functional Materials, North American Edition (1992); and U.S. Pat. No. 3,929,678, to Laughlin et al., issued Dec. 30, 1975 all of which are incorporated by reference herein in their entirety.

A wide variety of anionic surfactants are useful herein. Nonlimiting examples of anionic surfactants include the alkoyl isethionates, and the alkyl ether sulfates according to the teaching of U.S. Pat. No. 5,607,980 Mar. 4, 1997 and U.S. Pat. No. 5,821,237 Oct. 13, 1998. Nonlimiting examples of these isethionates include those alkoy isethonates selected from the group consisting of ammonium cocoyl isethionate, sodium cocoyl isethionate, sodium lauroyl isethionate, sodium stearoyl isethionate, and mixtures thereof, according to the teaching of U.S. Pat. No. 5,607,980 Mar. 4, 1997 and U.S. Pat. No. 5,821,237 Oct. 13, 1998.

Still other anionic synthetic surfactants include the class designated as succinamates, olefin sulfonates having about 12 to about 24 carbon atoms, and b-alkyloxy alkane sulfonates. Examples of these materials are sodium lauryl sulfate and ammonium lauryl sulfate. Other anionic materials include the sarcosinates nonlimiting examples of which include sodium lauroyl sarcosinate, sodium cocyl sarcosinate, and ammonium lauroyl carcosinate. Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, caster oil, tallow, lard, etc.) The fatty acids can also be synthetically prepared. Soaps are described in more detail in U.S. Pat. No. 4,557,853, cited above.

Other anionic materials include phosphates such as monoalkyl, dialkyl, and trialkylphosphate salts. Other anionic materials include alkanoyl sarcosinates corresponding to the formula RCON(CH3)CH2 CH2 CO2 M wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

Nonlimiting examples of preferred anionic surfactants useful herein include those selected from the group consisting of sodium lauryl sulfate, ammonium lauryl sulfate, ammonium cetyl sulfate, sodium cetyl surface, sodium stearyl sulfate, ammonium cocoyl isethionate, sodium lauroyl isethionate, sodium lauroyl sarcosinate, and mixtures thereof.

Especially preferred for use herein is sodium lauryl sulfate.

Cationic Surfactant

The compositions of the present invention comprise from about 0.1% to about 15%, more preferably from about 0.2% to about 10%, and most preferably from about 0.5% to about 5% of a cationic surfactant. Nonlimiting examples of cationic surfactants useful in the compositions of the present invention are disclosed in McCutcheon's, Detergents and Emulsifiers, North American edition (1986), published by allured Publishing Corporation; and McCutcheon's, Functional Materials, North American Edition (1992); both of which are incorporated by reference herein in their entirety. Nonlimiting examples of cationic surfactants useful herein include cationic ammonium salts according to the teaching of U.S. Pat. No. 5,607,980 Mar. 4, 1997 and U.S. Pat. No. 5,821,237 Oct. 13, 1998, incorporated by reference herein.

Alternatively, other useful cationic surfactants include amino-amides according to the teaching of U.S. Pat. No. 5,607,980 Mar. 4, 1997 and U.S. Pat. No. 5,821,237 Oct. 13, 1998, incorporated by reference herein. Nonlimiting examples of these cationic emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof.

Additional quaternary ammonium salts include those wherein the C12 to C22 alkyl carbon chain is derived from a tallow fatty acid or from a coconut fatty acid. The term "tallow" refers to an alkyl group derived from tallow fatty acids (usually hydrogenated tallow fatty acids), which generally have mixture of alkyl chains in the C16 to C18 range. The term "coconut" refers to an alkyl group derived from a coconut fatty acid, which generally have mixtures of alkyl chains in the C12 to C14 range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammoniums nitrate, di(coconutalkyl)dimethyl ammonium chloride, di(coconutalkyl)dimethyl ammonium bromide tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Preferred cationic surfactants useful herein include those selected from the group consisting of dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, and mixtures thereof.

Water

The compositions of the present invention comprise from about 45% to about 99.7%, more preferably from about 60% to about 95%, and most preferably from about 70% to about 90% of water. The exact level of water will depend upon the form of the product and the desired moisture content.

Additional Components

The compositions of the present invention can comprise a wide range of additional components. The CTFA Cosmetic Ingredient Handbook, Second Edition, 1992, which is incorporated by reference herein in its entirety, describes a wide variety of cosmetic and pharmaceutical ingredients commonly used in the skin care industry, which are suitable for use in the compositions of the present invention. Nonlimiting examples of functional classes of ingredients are described at page 537 of this reference. Examples of these functional classes include: absorbents, abrasives, anti-acne agents, anticaking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, fragrance comoponents, humectants, opacifying agents, pH adjusters, plasticers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include emulsifiers, sequestrants, skin sensates, and the like.

Nonlimiting examples of these additional components cited in the CTFA Cosmetic Ingredient Handbook, as well as other materials useful herein, include the following: vitamins and derivatives thereof [e.g., vitamin C, Vitamin A (i.e. retinoic acid), retinol, esters of retinoic acid, esters of retinol, retinoids, pathenol, pathenol esters, tocopherol, tocopherol esters, phytic acid, phytic acid esters, lycopene, flavones, flavonones, isoflavones, flavonols and other flavonoids]; oil or sebum control agents such as clays silicones and drug actives; sunscreening agents; other silicone material such as dimethiconol, dimethicone copolyol, and amodimethicone, and the like; anti-oxidants; antimicrobial agents; preservatives; emulsifiers; polyethylene glycols and polypropylene glycols; polymers for aiding the film-forming properties and substantivity of the compositions (such as a copolymer of eicosene and vinyl pyrrolidone, an example of which is available from GAF Chemical Corporation as Ganex.RTM. V-220); preservatives for maintaining the antimicrobial integrity of the compositions; anti-acne medicaments (e.g., resorcinol, sulfur, salicylic acid, erythromycin, zinc, and the like); skin bleaching (or lightening) agents including but not limited to hydroquinone, kojic acid; antioxidants; chelators and sequestrants; thickening agents such as carbomers (homopolymers of acrylic acid crosslinked with an allyl ether of pentaerythritol or an ally ether of sucrose), crosslinked and noncrosslinked nonionic and cationic polyacrylamides [e.g., Salcare.RTM. SC92 which has the CTFA designation polyquaternium 32 (and) mineral oil, and Salcare.RTM. SC95 which has the CTFA designation polyquaternium 37 (and) mineral oil (and) PPG-1 trideceth-6, and the nonionic Seppi-Gel polyacrylamides available from Seppic Corp.]; proteins and peptides; enzymes; ceramides; aesthetic components such as fragrances, pigments, colorings, essential oils, skin senates, astringents, skin soothing agents, skin healing agents and the like, [nonlimiting examples of these aesthetic components include clove oil, menthol, camphor, eucalyptus oil, eugenol, menthyl lactate, witch hazel distillate, bisabolol, dipotassium glycyrrhizinate and the like]; and skin conditioning agents such as urea and glycerol, and also the propoxylated glycerols described in U.S. Pat. No. 4,976,953, or Orr et al., issued Dec. 11, 1990, which is incorporated by reference herein in its entirety.

Some of these additional ingredients are described in more detail below.

Active Ingredients

The compositions of the present invention comprise a safe and effective amount of one or more active ingredients of pharmaceutically-acceptable salts thereof. The term "safe and effective amount" as used herein, means an amount of an active ingredient high enough to modify the condition to be treated or to deliver the desired skin benefit, but low enough to avoid serious side effects, at a reasonable benefit to risk ratio within the scope of sound medical judgement. What is a safe and effective amount of the active ingredient will vary with the specific active, the ability of the active to penetrate through the skin, the age, health condition, and skin condition of the user, and other like factors.

Typically, the active ingredients of the present invention comprise from about 0.001% to about 20%, preferably from about 0.01% to about 15%, and more preferably from about 0.025% to about 10% by weight of the composition.

The active ingredients useful herein can be categorized by their therapeutic benefit or their postulated mode of action. However, it is to be understood that the active ingredients useful herein can in some instances provide more than one therapeutic benefit or operate via more than one mode of action. Therefore, classifications herein are made for the sake of convenience and are not intended to limit the active ingredient to that particular application or applications listed. Also, pharmaceutically-acceptable salts of these active ingredients are useful herein. The following active ingredients are useful in the compositions of the present invention.

Anti-Acne Actives: Examples of useful anti-acne actives include the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cystein; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxisopropanol, ethyl acetate, clindamycin and meclocycline; sebostats such as flavonoids; and bile salts such as scymnol sulfate and its derivatives, deoxycholate, and cholate.

Anti-Wrinkle and Anti-Skin Atrophy Actives: Examples of antiwrinkle and anti-skin atrophy actives include retinoic acid and its derivatives (e.g., cis and trans); retinol, retinyl esters, salicylic acid and derivatives thereof; sulfur-containing D and L amino acids and their derivatives and salts, particularly the N-acetyl derivatives, a preferred example of which is N-acetyl-L-cystein; thiols, e.g., ethane thiol; alpha-hydroxy acids, e.g. glycolic acid, and lactic acid; phytic acid, lipoic acid; lysophosphatidic acid, and skin peel agents (e.g., phenol and the like).

Non-Steroidal Anti-Inflammatory Actives (NSAIDS): Examples of NSAIDS include the following categories: propionic acid derivatives; acetic acid derivatives; fenamic acid derivatives; biphenylcarboxylic acid derivatives; and oxicams. All of these NSAIDS are fully described in U.S. Pat. No. 4,985,459 to Sunshine et al., issued Jan. 15, 1991, incorporated by reference herein in its entirety. Examples of useful NSAIDS include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, microprofen, tioxaprofen, suprofen, alminoprofen, tiaprofenic acid, fluprofen and bucloxic acid. Also useful are the steroidal anti-inflammatory drugs including hydrocortisone and the like.

Topical Anesthetics: Examples of topical anesthetic drugs include benzocaine, lidocaine, bupivacaine, chlorprocaine, dibucaine, etidocaine, mepivacaine, tetracaine, dyclonine, hexyclaine, procaine, cocaine, ketamine, pramoxine, phenol, and pharmaceutically acceptable salts thereof.

Artificial Tanning Agents and Accelerators: Examples of artificial tanning agents and accelerators include dihydroxyacetone, tyrosine, tyrosine esters such as ethyl tyrosinate, and phospho-DOPA.

Antimicrobial and Antifungal Actives: Examples of antimicrobial and antifungal actives include .beta.-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin steaerate, amikacin sulfate, doxycycline hydrochloride, capreomycin sulfate, chlorhexidine gluconate, chlorhexidine hydrochloride, chlortetracycline, hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mendelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xyleneol, nystatin, tolnaftate and clotrimazole.

Phytoestrogens: Also useful herein are plant-derived compounds with estrogen-like activity. A wide variety of such compounds exist and are called phytoestrogens. Particular examples of these plant-derived compounds with estrogen-like compounds include isoflavones, especially soy-derived isoflavones, such as genistein and daidzein.

Sunscreen Actives: Also useful herein are sunscreening actives. A wide variety of sunscreening agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of Cosmetic Science and Technology, all of which are incorporated herein by reference in their entirety. Non-limiting examples of sunscreens which are useful in the compositions of the present invention are those selected from the group consisting of 2-ethylhexyl p-methoxycinnamate, 2-ethylhexyl-N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropy dibenzoylmethane, 3-benzylidene camphor, 3-(4-methylbenzylidene) camphor, titanium dioxide, zinc oxide, silica, iron oxide, and mixtures thereof. Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. The sunscreening agents disclosed therein have, in a single molecule, two distinct chromophore moieties which exhibit different ultraviolet radiation absorption spectra. One of the chromophore moieties absorbs predominantly in the UVB radiation range and the other absorbs strongly in the UVA radiation range. These sunscreening agents provide higher efficacy, broader UV absorption, lower skin penetration and longer lasting efficacy relative to conventional sunscreens. Especially preferred examples of these sunscreens include those selected from the group consisting of 4-N,N-(2-ethylhexyl)methylaminobenzoic acid ester of 2,4-dihydroxybenzophenone, 4-N,N-(2-ethylhexyl)-methylaminobenzoic acid ester with 4-hydroxydibenzoylmethane, 4-N,N-(2-ethylhexyl)-methylaminobenzoic acid ester of 2-hydroxy-4-(2-hydroxyethoxy)-benzophenone, 4-N,N-(2-ethylhexyl)-methylaminobenzoic acid ester of 4-(2-hydroxyethoxy)-dibenzoylmethane, and mixtures thereof. Generally, the sunscreens can comprise from about 0.5% to about 20% of the compositions useful herein. Exact amounts will vary depending upon the sunscreen chosen and the desired Sun Protection Factor (SPF). SPF is a commonly used measure of photoprotection of a sunscreen against erythema. See Federal Register, Vol. 43, No. 166, pp. 38206–38269, Aug. 25, 1978, which is incorporated herein by reference in its entirety.

Preferred examples of actives useful herein include those selected from the group consisting of salicylic acid, 3-hydroxy benzoic acid, glycolic acid, lactic acid, 4-hydroxy benzoic acid, acetyl salicylic acid, 2-hydroxybutanoic acid, 2-hydroxypentanoic acid,2-hydroxyhexanoic acid, cis-retinoic acid, trans-retinoic acid, retinol, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbailide, octopirox, lidocaine hydrochloride, clotrimazole, miconazole, neocycin sulfate, p-aminobenzoic acid, 2-phenylbenzimidazole-5-sulfonic acid, dihydroxyacetone, and mixtures thereof.

More preferred examples of actives useful herein include those selected from the group consisting of salicylic acid, benozyl peroxide, acetyl salicylic acid, cis-retinoic acid, trans-retinoic acid, retinol, phytic acid, N-acetyl-L-cystein, lipoic acid, azelaic acid, tetracycline, ibuprofen, naproxen acetominophen, hydrocortisone, resorcinol, phenoxyethanol, phenoxypropanol, phenoxyisopropanol, 2,4,4'-trichloro-2'-hydroxy diphenyl ether, 3,4,4'-trichlorocarbanilide, octopirox, 2-phenylbenzimidazole-5-sulfonic acid, dihydroxyacetone, and mixtures thereof.

Most preferred examples of actives useful herein include those selected from the group consisting of salicyclic acid, benzoyl peroxide, cis-retinoic acid, trans-retinoic acid, retinol, phytic acid, N-acetyl L-cysteine, azelaic acid, lipoic acid, resorcinol, lactic acid, glycolic acid, ibuprofen, naproxen, hydrocortisone, phenoxyethanol, phenoxypropanol, phenoxyisopropanol, 2,4,4'-trichloro-2'-hydroxy diphenyl ether, 3,4,4'-trichlorocarbanilide, 2-ethylhexyl p-methoxycinnamic acid, oxybenzone, 2-phenylbenzimidazole-5-sulfonic acid, dihydroxyacetone, and mixtures thereof.

Humectants and Moisturizers

The compositions of the present invention can also comprise one or more humectants or moisturizers. A variety of these materials can be employed and each can be present at a level of from about 0.1% to about 20%, more preferably from about 0.5% to about 15%, and most preferably from about 1% to about 10%. Nonlimiting examples of humectants include materials selected from the group consisting of guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof. Also, useful are propoxylated glycerols as described in U.S. Pat. No. 4,976,953, to Orr et al., issued Dec. 11, 1990, which is incorporated by reference herein in its entirety.

An especially preferred humectant for use herein is glycerol.

Insoluble Particles

The compositions of the present invention can comprise from about 0.1% to about 20%, more preferably from about 0.25% to about 15%, and most preferably from about 0.5% to about 10%, based on the weight of the total composition, of insoluble particles which are useful for enhancing the cleansing effect, when the compositions of the present invention are in the form of a cleansing composition.

The term "insoluble", as used herein, means that the particles are essentially insoluble in the compositions of the present invention. In particular, the insoluble particles should have a solubility less than about 1 gram per 100 grams of composition at 25 degree C., preferably less than about 0.5 grams per 100 grams of composition at 25 degree C., and more preferably less than about 0.1 grams per 100 grams of composition at 25 degree C.

Useful herein are both micronized and conventional size insoluble particles. The micronized particles, for the most part, are of a size that is below the tactile threshold and are essentially nonabrasive to the skin. The conventional size particles are tactilely perceptible and are added for the scrubbing and abrasive effect which they provide. The micronized particles have a mean particle size diameter and particle size distribution such that they are below the tactile perception threshold of most users, and yet are not so small as to be ineffective for aiding in oil, dirt, and debris (e.g., make-up) removal. It is found herein that particles having a mean particle size diameter greater than about 75 microns are tactilely perceived during the cleansing process and it is important to minimize the amount of these larger particles if it is desired that the particles not be felt by the user. Conversely, it is found that particles having a means particle size diameter of less than about 1 to about 5 microns are generally less effective for providing a cleansing benefit. Without being limited by theory, it is believed that the micronized cleansing particles should be of a size that is on the order of the thickness of the dirt, oil, or debris layer to be cleaned away. This layer is believed to be on the order of a few microns in thickness in most instance. It is therefore found in the present invention that the micronized particles should have a mean particle size diameter from about 1 to about 75 microns, more preferably from about 15 to about 60 microns, and most preferably from about 20 to about 50 microns, so as to provide effective cleansing without being tactilely perceptible. Particles having a wide range of shapes, surface characteristics, and hardness characteristics can be utilized herein provided the particle size requirements are met. Micronized particles of the present invention can be derived from a wide variety of materials including those derived from inorganic, organic, natural, and synthetic sources.

Nonlimiting examples of these materials include those selected from the group consisting of almond meal, alumina, aluminum oxide, aluminum silicate, apricot seed powder, attapulgite, barley flour, bismuth oxychloride, boron nitride, calcium carbonate, calcium phosphate, calcium pyrophosphate, calcium sulfate, cellulose, chalk, chitin, clay, corn cob meal, corn cob powder, corn flour, corn meal, corn starch, diatomaceous earth, dicalcium phosphate, dicalcium phosphate dihydrate, fullers earth, hydrated silica, hydroxyapatite, iron oxide, jojoba seed powder, kaolin, loofah, magnesium trisilicate, mica, microcrystalline cellulose, montmorillonite, oat bran, oat flour, oatmeal, peach pit powder, pecan shell powder, polybutylene, polyethylene, polyisobutylene, polymethylstyrene, polypropylene, polystyrene, polyurethane, nylon, teflon (i.e. polytetrafluoroethylene), polyhalogenated olefins, pumice rice bran, rye flour, cericite, silica, silk, sodium bicarbonate, sodium silicoaluminate, soy flour synthetic hectorite, talc, tin oxide, titanium disoide, tricalcium phosphate, walnut shell powder, wheat bran, wheat flour, wheat starch, zirconium silicate, and mixtures thereof. Also useful are micronized particles made from mixed polymers (e.g., copolymers terpolymers, etc.), such as polyethlene/polypropylene copolymer, polyethylene/propylene/isobutylene copolymer, polyethlene/styrene copolymer, and the like. Typically, the polymeric and mixed polymeric particles are treated via an oxidation process to destroy impurities and the like. The polymeric and mixed polymeric particles can also optionally be crosslinked with a variety of common crosslinking agents, nonlimiting examples of which include butadiene, divinyl benzene, methylenebisacrylamide, allyl ethers of sucrose, allyl ethers of pentaerythritol, and mixtures thereof. Other examples of useful micronized particles include waxes and resins such as paraffins, carnuba wax, ozekerite wax, candellila wax, urea-formaldehyde resins, and the like. When such waxes and resins are used herein it is important that these materials are solids at ambient and skin temperatures.

Among the preferred water-insoluble, micronized particulate materials useful herein are the synthetic polymeric particles selected from the group consisting of polybutylene, polyethylene, polyisobutylene, polymethylstyrene, polypropylene, polystyrene, polyurethane, nylon, teflon, and mixtures thereof. Most preferred are polyethylene and polypropylene micronized particles, with the oxidized versions of these materials being especially preferred. Examples of commercially available particles useful herein include the ACumist.TM. micronized polyethylene waxes available from Allied Signal (Morristown, N.J.) available as the A, B, C, and D series in a variety of average particle sizes ranging from 5 microns to 60 microns. Preferred are the ACumist.TM. A-25, A-30, and A-45 oxidized polyethylene particles having a mean particle size of 25, 30, and 45 microns, respectively. Examples of commercially available polyproylene particles include the Porpyltex series available from Micro Powders (Dartek).

The conventional size insoluble particles are well-known to formulation chemists in the art. These particles typically have larger particle sizes than the micronized particles described herein. These particles generally have an average size diameter that is about 75 microns or greater, which is above the tactile threshold described above. These conventional size particles typically have average particles sizes ranging up to about 400 microns and larger. These particles can be made from the same materials as for the micronized particles just described. Among the preferred conventional size particulate materials useful herein are the synthetic polymeric particles selected from the group consisting of polybutylene, polyethylene, polyisobutylene, polymethylstyrene, polyethylene and polypropylene micronized particles, with the oxidized versions of these materials being especially preferred. An example of a commercially available conventional size particle useful herein is ACuscrub.TM.51, available from Allied Signal (Morristown, N.J.) having a mean particle size of about 125 microns.

Emulsifiers

The compositions herein can comprise various emulsifiers. These emulsifiers are useful for emulsifying the various carrier components of the compositions herein. Suitable emulsifiers can include any of a wide variety of nonionic, cationic, anionic, and zwitterionic emulsifiers disclosed in the prior patents and other references. See McCutcheon's, Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety.

Suitable emulsifier types include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps and mixtures thereof. Suitable emulsifiers can include, but are not limited to, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

The emulsifiers can be used individually or as a mixture of two or more and can comprise from about 0.1% to about 10%, more preferably from about 0.15% to about 7%, and most preferably from about 0.2% to about 5% of the compositions of the present invention.

Oils

The compositions of the present invention can comprise from about 0.25% to about 40%, preferably from about 0.5% to about 25%, and more preferably from about 0.75% to about 15% of an oil selected from the group consisting of mineral oil, petrolatum, C7–C40 branched chain hydrocarbons, C1–C30 alcohol esters of C1–C30 carboxylic acids, C1–C30 alcohol esters of C2–C30 dicarboxylic acids, monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glucol diesters of C1–C30 carboxylic acids, propylene glycol monoesters of C1–C30 carboxylic acids, propylene glucol diesters of C1–C30 carboxylic acids, C1–C30 carboxylic acid monesters and polyesters of sugars, polydialkylsiloxanes, polydiarylsiloxanes, polyalkarylsiloxanes, cyclomethicones having 3 to 9 silicon atoms, vegetable oils, hydrogenated vegetable oils, polypropylene glycols, polypropylene glycol C4–C20 alkyl ethers, di C8–C30 alkyl ethers, and mixtures thereof.

The oil materials generally having low solubility in water, generally less than about 1% by weight at 25 degree C. Nonlimiting examples of suitable oil components include, but are not limited to, the following materials. Some of these materials are further described in U.S. Pat. No. 4,919,934, to Deckner et al., issued Apr. 24, 1990, which is incorporated herein by reference in its entirety.

Mineral oil, which is also known as petrolatum liquid, is a mixture of liquid hydrocarbons obtained from petroleum. See The Merck Index, Tenth Edition, Entry 7048, p. 1033 (1983) and International Cosmetic Ingredient Dictionary, Fifth Edition, vol. 1, p. 415–417 (1993), which are incorporated by reference herein in their entirety.

Petrolatum, which is also known as petroleum jelly, is a colloidal system of nonstraight-chain solid hydrocarbons and high-boiling liquid hydrocarbons, in which most of the liquid hydrocarbons are held inside the micelles. See The Merck Index, Tenth Edition, Entry 7047, p. 1033 (1983); Schindler, Drug. Cosmet. Ind., 89, 36–37, 76, 78–80, 82 (1961); and International Cosmetic Ingredient Dictionary, Fifth Edition, vol. 1, p. 537 (1993), which are incorporated by reference herein in their entirety.

Straight and branched chain hydrocarbons having from about 7 to about 40 carbon atoms are useful herein. Nonlimiting examples of these hydrocarbon materials include dodecane, isododecane, squalane, cholesterol, hydrogenated polyisobutylene, docosane (i.e. a $C_{22}$ hydrocarbon), hexadecane, isohexadecane (a commercially available hydrocarbon sold as Permethyl.RTM. 101A by Presperse, South Plainfield, N.J.). Also useful are the C7–C40 isoparaffins, which are C7–C40 branched hydrocarbons.

Useful oils include C1–C30 alcohol esters of C1–C30 carboxylic acids and of C2–C30 dicarboxylic acids, including straight and branched chain materials as well as aromatic derivatives. Also useful are esters such as monoglycerides of C1–C30 carboxylic acids, deglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, and propylene glycol diesters of C1–C30 carboxylic acids. Straight chain, branched chain and aryl carboxylic acids are included herein. Also useful are propoxylated and ethoxylated drivatives of these materials. Nonlimiting examples include diisopropyl sebacate, diisopropyl adipate, isopropyl myristate, isopropyl palmitate, myristyl propionate, ethylene glycol distearate, 2-ethylhexyl palmitate, isodecyl neopentanoate, $C_{12-15}$ alcohols benzoate, di-2-ethylhexyl maleate, cetyl palmitate, myristyl myristate, stearyl stearate, cetyl stearate, behenyl behenrate, dioctyl maleate, dioctyl sebacate, diisopropyl adipate, cetyl octanoate, diisopropyl dilinoleate, caprilic/capric triglyceride, PEG-6 caprylic/capric triglyceride, PEG-8 caprylic/capric triglyceride, and mixtures thereof.

Also useful are various C1–C30 monesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, surcrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboyxlic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behanate in a 2:6 molar ratio; and the octaester of sucrose wherein the esterifying carboxylic acid moieties are laurate, linoleate and behenate in a 1:3:4 molar ratio. A preferred solid material is surcrose polyester in which the degree of esterification is 7–8, and in which the fatty acid moieties are C18 mono- and/or di-unsaturated and behenic, in a molar ratio of unsaturates:behenic of 1:7 to 3:5. A particularly preferred solid sugar polyester is the octaester of sucrose in which there are about 7 behenic fatty acid moieties and about 1 oleic acid moiety in the molecule. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

Silicones such as polydialkylsiloxanes, polydiarylsiloxanes, polyalkarylsiloxanes, and cyclomethicones having 3 to 9 silicon atoms are useful oils. These silicones include both volatile and nonvolatile materials. These silicones are disclosed in U.S. Pat. No. 5,069,897, to Orr, issued Dec. 3, 1991, which is incorporated by reference herein in its entirety. The polyalkylsiloxanes include, for example, polyalkylsiloxanes with viscosities of from about 0.5 to about 100,000 centistokes at 25 degree C. Commercially available polyalkylsiloxanes include the polydimethylsiloxanes, which are also known as dimethicones, nonlimiting examples of which include the Vicasil.RTM. series sold by General Electric Company and the Dow Corning.RTM. 200 series sold by Dow Corning Corporation. Specific examples of polydimethylsiloxanes useful as emollients herein include Dow Corning.RTM. 200 fluid having a viscosity of 0.65 centistokes and a boiling point of 100 degree C., Dow Corning.RTM. 225 fluid having a viscosity of 10 centistokes and a boiling point greater than 200 degree C., and Dow Corning.RTM. 200 fluids having viscosities of 50, 350, and 12,500 centistokes, respectively, and boiling points greater than 200 degree C. Cyclic polyalkylsiloxanes useful herein include those corresponding to the general chemical formula $[SiR_2—O]_n$ wherein R is an alkyl group (preferably R is methyl or ethyl, more preferably methyl) and n is an integer from about 3 to about 9, more preferably n is an integer from about 3 to about 7, and most preferably n is an integer from about 4 to about 6. When R is methyl, these materials are typically referred to as cyclomethicones. Commercially available cyclomethicones include Dow Corning.degree. 244 fluid having a viscosity of 2.5 centistokes, and a boiling point of 172 degree C., which primarily contains the cyclomethicone tetramer (i.e. n=4), Dow Corning.RTM. 344 fluid having a viscosity of 2.5 centistokes and a boiling point of 178 degree C., which primarily contains the cyclomethicone pentamer (i.e. n=5), and Dow Corning.RTM. 245 fluid having a viscosity of 4.2 centistokes and a boiling point of 205 degree C., which primarily contains a mixture of the cyclomethicone tetramer and pentamer (i.e. n=4 and 5), Dow Corning.RTM. 345 fluid having a viscosity of 4.5 centistokes and a boiling point of 217 degree C., which primarily contains a mixture of the cyclomethicone tetramer, pentamer, and hexamer (i.e. n=4, 5, and 6). Also useful are materials such as trimethylsiloxysilicate, which is a polymeric material corresponding to the general chemical formula $[(CH_2)_3]_x[SiO_2]_y$, wherein x is an integer from about 1 to about 500 and y is an integer from about 1 to about 500. A commercially available trimethylsiloxysilicate is sold as a mixture with dimethicone as Dow Corning.RTM. 593 fluid. Also useful herein are dimethiconols, which are hydroxy terminated dimethyl silicones. Commercially available dimethiconols are typically sold as mixtures with dimethicone or cyclomethicone (e.g. Dow Corning.RTM.1401, 1402, and 1403 fluids). Also useful herein are polyalkylaryl siloxanes, with polymethyphenyl siloxanes having viscosities from about 15 to about 65 centistokes at 25 degree C. being preferred. These materials are available, for example, as SF 1075 methylphenyl fluid (sold by General Electric Company) and 556 Cosmetic Grade phenyl trimethicone fluid (sold by Dow Corning Corporation).

Vegetable oils and hydrogenated vegetable oils are also useful herein. Examples of vegetable oils and hydrogenated vegetable oils include safflower oil, caster oil, coconut oil, cottenseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated caster oil, hydrogenated coconut oil, hydrogenated cottenseed oil, hydrogenated menhaden oil, hydrogenated palm kernel oil, hydrogenated palm oil, hydrogenated peanut oil hydrogenated soybean oil, hydrogenated rapeseed oil, hydrogenated linseed oil, hydrogenated rice bran oil, hydrogenated sesame oil, hydrogenated sunflower seed oil, and mixtures thereof.

Also useful are polyproylene glycols, C4–C20 alkyl ethers of polypropylene glycols, C1–C20 carboxylic acid esters of polypropylene glycols, and di-C8–C30 alkyl ethers. Nonlimiting examples of these materials include PPG-14 butyl ether, PPG-15 stearyl ether, PPG-9, PPG-12, PPG-15, PPG-17, PPG-20, PPG-26, PPG-30, PPG-34, dioctyl ether, dodecyl octyl ether, and mixtures thereof.

Method of Forming the Complexes

The complexes that are believed to be formed from the amphoteric, anionic, and cationic surfactants of the present invention are preferably preprepared by the following procedures. The amphoteric and anionic surfactants are first combined in aqueous solution, thereby forming what is believed to be a dispersion of the complex between these two materials. This dispersion is then combined directly with an aqueous solution of the cationic surfactant. Alternatively, this dispersion can be added directly to a composition already containing the desired cationic surfactant.

Methods of Treating the Skin

The present invention also relates to methods wherein an effective amount of the composition of the present invention is applied to the skin. These compositions are useful for conditioning and treating dry skin and for providing active ingredients to the skin. A wide range of quantities of the compositions of the present invention can be used. Quantities which are typically applied can range from about 0.1 mg/cm2 to about 25 mg/cm2.

In further embodiments, the compositions of the present invention are useful for personal cleansing, especially for cleansing of the face and neck areas. Typically, a suitable or effective amount of the cleansing composition is applied to the area to be cleansed. Alternatively, a suitable amount of the cleansing composition can be applied via intermediate application to a washcloth, sponge, pad, cotton ball or other application device. If desired, the area to be cleansed can be premoistened with water. It has been found that the compositions of the present invention can be combined with water during the cleansing process and rinsed-off from the skin. Alternatively, the composition can be used along and wiped-off from the skin using a pad, cotton ball, tissue, or other like device. The cleansing process is typically a two-step process involving application of the composition followed either by rinsing of the produce with water or wiping without the use of water. Generally, an effective amount of composition to be used will depend upon the needs and usage habits of the individual.

EXAMPLES OF HOW TO PRACTICE THE INVENTION

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name.

Example 1

A leave-on lotion composition containing benzoyl peroxide is prepared by combining the following ingredients using conventional mixing techniques.

| Ingredients | Weight Percent |
| --- | --- |
| Phase A | |
| Water | QS 100 |
| Glycerin | 4.00 |
| Disodium EDTA | 0.10 |
| Carbomer | 0.60 |
| Acrylates/C10-30 Alkylacrylates Crosspolymer | 0.05 |
| Phase B | |
| Stearyl Alcohol | 2.25 |
| Cetyl Alcohol | 2.25 |
| Steareth-100 | 0.50 |
| Distearyl Dimethyl Ammonium Chloride | 0.20 |
| Phase C | |
| Triethanolamine | 0.50 |
| Phase D | |
| Lipoic acid derivative | 1.0–20.0 |
| Phase E | |
| Cetyl Dimethyl Betaine | 1.00 |
| Sodium Lauryl Sulfate | 0.50 |

In a suitable vessel, the Phase A ingredients are heated with stirring to about 75 degree C. In a separate vessel, the Phase B ingredients are heated with stirring to about 75 degree C. Phase B is then added to Phase A with mixing. Next Phase C is added with mixing. Next, the mixture is cooled to 35 degree C. Next the active lipoic acid derivative, synthesized as described in this invention, is added with mixing. In a separate vessel, the Phase E ingredients are combined and added to the remaining mixture with stirring.

The resulting leave-on composition is useful for preventing and treating acne (including rosacea) while being mild to the skin. Alternatively, a composition is prepared in which the cetyl dimethyl betaine is replaced with stearyl dimethyl betaine.

Example 2

A personal cleanser composition containing salicylic acid is prepared by combining the following ingredients using conventional mixing techniques.

| Ingredients | Weight Percent |
|---|---|
| Phase A | |
| Water | QS 100 |
| Glycerin | 3.00 |
| Disodium EDTA | 0.01 |
| Phase B | |
| PPG-15 Stearyl Ether | 4.00 |
| Stearyl Alcohol | 2.88 |
| Distearyl Dimonium Chloride | 1.50 |
| Cetyl Alcohol | 0.80 |
| Steareth-21 | 0.50 |
| Behenyl Alcohol | 0.32 |
| PPG-30 | 0.25 |
| Steareth-2 | 0.25 |
| Phase C | |
| Lipoic acid derivative | 1.00–20.00 |
| Fragrance | 0.27 |
| Phase D | |
| Cocamidopropyl Betaine | 2.00 |
| Sodium Lauryl Sulfate | 1.00 |

In a suitable vessel, the Phase A ingredients are heated with stirring to about 75 degree C. In a separate vessel, the Phase B ingredients are heated with stirring to about 75 degree C. Phase B is then added to Phase A with mixing. Next, the oxidized polyethylene beads are added slowly with mixing to prevent agglomeration. Next the fragrance is added with mixing. Next, the mixture is cooled to 35 degree C. In a separate vessel, the Phase D ingredients are combined and added to the remaining mixture with stirring (typically these ingredients are available as aqueous solutions and are combined as such).

The resulting cleansing composition is useful for preventing and treating skin damage induced by sunlight (UV radiation) and for cleansing the skin. Alternatively, a composition is prepared in which the sodium lauryl sulfate is replaced with sodium lauroyl isetheonate.

Example 3

A personal cleanser is prepared by combining the following ingredients using conventional mixing techniques.

| Ingredients | Weight Percent |
|---|---|
| Phase A | |
| Water | QS 100 |
| Glycerin | 3.00 |
| Disodium EDTA | 0.10 |
| Methylparaben | 0.15 |
| Phase B | |
| PPG-15 Stearyl Ether | 4.00 |
| Stearyl Alcohol | 2.88 |
| Distearyl Dimonium Chloride | 1.50 |
| Cetyl Alcohol | 0.80 |
| Steareth-21 | 0.50 |
| Behenyl Alcohol | 0.32 |
| PPG-30 | 0.25 |
| Steareth-2 | 0.25 |
| Propylparaben | 0.10 |
| Phase C | |
| Fragrance | 0.27 |
| Menthol | 0.05 |
| Lipoic acid derivative | 1.00–20.00 |
| Phase D | |
| Cetyl Dimethyl Betaine | 2.00 |
| Sodium Lauryl Sulfate | 1.00 |

In a suitable vessel, the Phase A ingredients are heated with stirring to about 75 degree C. In a separate vessel, the Phase B ingredients are heated with stirring to about 75 degree C. Phase B is then added to Phase A with mixing. Next the fragrance and menthol are added with mixing. Next, the mixture is cooled to 35 degree C. In a separate vessel, the Phase D ingredients are combined and added to the remaining mixture with stirring (typically these ingredients are available as aqueous solutions and are combined as such).

The resulting cleansing composition is useful for cleansing the skin, for preventing or ameliorating skin dryness and wrinkle formation in the skin, for preventing thinning of the skin, for increasing the thickness, hydration and pliability of the skin, and for inhibiting the aging process in skin. Alternatively, a composition is prepared in which the menthol is eliminated and the water level is correspondingly increased.

Alternatively, a composition is prepared in which the sodium lauryl sulfate is replaced with sodium lauroyl isetheonate.

Example 4

A leave-on cream composition is prepared by combined the following ingredients using conventional mixing techniques.

| Ingredients | Weight Percent |
|---|---|
| Phase A | |
| Water | QS 100 |
| Glycerin | 5.00 |
| Disodium EDTA | 0.10 |
| Methylparaben | 0.20 |
| Phase B | |
| PPG-15 Stearyl Ether | 4.00 |
| Stearyl Alcohol | 1.44 |
| Distearyl Dimonium Chloride | 0.50 |
| Cetyl Alcohol | 0.40 |

-continued

| Ingredients | Weight Percent |
|---|---|
| Steareth-21 | 0.50 |
| Behenyl Alcohol | 0.16 |
| Steareth-2 | 0.15 |
| Propylparaben | 0.10 |
| Phase C | |
| Fragrance | 0.12 |
| Lipoic acid derivative | 1.0–20.0 |
| Phase D | |
| Cetyl Dimethyl Betaine | 1.00 |
| Sodium Lauryl Sulfate | 0.50 |

In a suitable vessel, the Phase A ingredients are heated with stirring to about 75 degree C. In a separate vessel, the Phase B ingredients are heated with stirring to about 75 degree C. Phase B is then added to Phase A with mixing. Next the fragrance is added with mixing. Next, the mixture is cooled to 35 degree C. In a separate vessel, the Phase D ingredients are combined and added to the remaining mixture with stirring (typically these ingredients are available as aqueous solutions and are combined as such).

The resulting leave-on cream is useful for conditioning the skin and provides a soft/smooth skin feel. for preventing or ameliorating skin dryness, for preventing thinning of the skin, for increasing the thickness, hydration and pliability of the skin, and for inhibiting the aging process in skin. Alternatively, a composition is prepared in which the sodium lauryl sulfate is replaced with sodium lauroyl isetheonate.

Example 5

A leave-on lotion composition containing a lipoic acid derivative is prepared by combining the following ingredients using conventional mixing techniques.

| Ingredients | Weight Percent |
|---|---|
| Phase A | |
| Water | QS 100 |
| Glycerin | 3.00 |
| Tetrasodium EDTA | 0.02 |
| Phase B | |
| PPG-15 Stearyl Ether | 4.00 |
| Stearyl Alcohol | 0.75 |
| Salicylic Acid | 2.00 |
| Cetyl Alcohol | 0.75 |
| Steareth-21 | 0.45 |
| Steareth-2 | 0.05 |
| Distearyl Dimethyl Ammonium Chloride | 0.75 |
| Polyquatemium-37 (and) Mineral Oil (and) PPG-1 Trideceth-6 | 0.75 |
| Phase C | |
| Triethanolamine | 0.15 |
| Phase D | |
| Lipoic acid derivative | 1.0–20.0 |
| Fragrance | 0.10 |
| Phase E | |
| Cetyl Dimethyl Betaine | 2.00 |
| Sodium Lauryl Sulfate | 1.00 |

In a suitable vessel, the Phase A ingredients are heated with stirring to about 75 degree C. In a separate vessel, the Phase B ingredients are heated with stirring to about 75 degree C. Phase B is then added to Phase A with mixing. Next Phase C is added with mixing.

Next the Phase D ingredients are added with mixing. Next, the mixture is cooled to 35 degree C. In a separate vessel, the Phase E ingredients are combined and added to the remaining mixture with stirring.

The resulting leave-on composition is useful for preventing treating acne while being mild to the skin and providing a soft/smooth skin feel, and for preventing or ameliorating skin dryness and wrinkle formation in the skin, for preventing thinning of the skin, for increasing the thickness, hydration and pliability of the skin, and for inhibiting the aging process in skin. Alternatively, a composition is prepared in which the sodium lauryl sulfate is replaced with sodium lauroyl isetheonate.

Example 6

Alternative Liquid Formulation

The following alternative formulations demonstrate the typical use of the protective skin composition of the present invention in skin care and over the counter (OTC) pharmaceutical products. These formulations are listed only as examples of the types of compositions that could be used, and are not all encompassing of the possible uses of the technology in skin care and OTC pharmaceutical products. One skilled in the art of formulation will readily envision other possible uses for this technology, and the invention is not restricted the use of the formulations listed below. All ingredients of the formulations listed below are shown in percentage by weight (% w/w). The following is a general formula for ligand formulations of the composition.

| Materials | General Use Range (Wt %) |
|---|---|
| Purified Water | 19.00000–98.71330 |
| Surfactants | 0.50–5.00 |
| Lipoic acid derivative | 1.0–20.0 |
| Humectant | 0.50–5.00 |
| Fragrance | 0.001–1.00 |
| Preservatives | 0.20–3.00 |
| Sequestering Agent | 0.01–0.50 |
| Menthol | 0.005–1.00 |
| Vitamin A Palmitate | 0.0005–0.50 |
| Vitamin B Acetate | 0.05–30.00 |
| Magnesium Ascorbyl Phosphate | 0.0001–3.00 |
| Beta Glucan | 0.005–5.00 |
| Superoxide Dismutase | 0.0001–1.00 |
| Grape Seed Extract | 0.00001–1.00 |
| Panthenol | 0.005–5.00 |
| Total | 100.00000% |

Example 7

Alternative Skin Toner

The following composition is useful for preventing treating acne (including rosacea) while being mild to the skin and providing a soft/smooth skin feel, and for preventing or ameliorating skin dryness and wrinkle formation in the skin, for preventing thinning of the skin, for increasing the thickness, hydration and pliability of the skin, and for inhibiting the aging process in skin.

| Materials | Specific Use Concentration (Wt %) |
|---|---|
| Purified Water | 79.4719 |
| Surfactants | 2.0000 |
| Witch Hazel Distillate | 15.0000 |
| Humectant | 1.0000 |
| Lipoic acid derivative | 1.0–20.0 |
| Fragrance | 0.0350 |
| Preservatives | 1.9000 |
| Sequestering Agent | 0.1000 |
| Menthol | 0.0100 |
| Plant Extracts | 0.0700 |
| Vitamin A Palmitate | 0.0050 |
| Vitamin B Acetate | 0.1000 |
| Magnesium Ascorbyl Phosphate | 0.0040 |
| Beta Glucan | 0.1000 |
| Superoxide Dismutase | 0.0040 |
| Grape Seed Extract | 0.0001 |
| Panthenol | 0.2000 |
| Total | 100.0000% |

Example 8

Alternative Skin Moisturizing Lotion

The following oil-in-water formulation was developed as a moisturizing lotion for the skin.

| Materials | Specific Use Concentration (Wt %) |
|---|---|
| Purified Water | 79.4719 |
| O/W Emulsifiers | 11.0000 |
| Humectants | 5.0000 |
| Fragrance | 0.0500 |
| Preservatives | 2.7000 |
| Sequestering Agent | 0.1000 |
| Emollients | 12.0000 |
| Thickeners | 0.3000 |
| Vitamin A Palmitate | 0.0500 |
| Vitamin E Acetate | 1.0000 |
| Magnesium Ascorbyl Phosphate | 0.2500 |
| Beta Glucan | 1.0000 |
| Superoxide Dismutase | 0.0400 |
| Grape Seed Extract | 0.0050 |
| Panthenol | 2.0000 |
| Lipoic acid derivative | 1.0–20.0 |
| Total | 100.0000% |

Example 9

Synthetic (Moisturizing) Soap Bar

The following is a general formulation for a moisturizing soap bar.

| Materials | General Use Range (Wt %) |
|---|---|
| Purified Water | 0.00–15.00 |
| Detergents and Cleansing Agents | 32.0000–97.9573 |
| Buffering Agents | 1.00–3.00 |
| Humectants and Skin Conditioning Agents | 0.50–5.00 |
| Fragrance | 0.001–1.00 |
| Preservatives | 0.01–2.00 |
| Thickeners and Coloring Agents | 0.01–30.00 |
| Vitamin A Palmitate | 0.0005–0.50 |
| Vitamin E Acetate | 0.05–30.00 |

-continued

| Materials | General Use Range (Wt %) |
|---|---|
| Magnesium Ascorbyl Phosphate | 0.0001–3.00 |
| Beta Glucan | 0.005–5.00 |
| Superoxide Dismutase | 0.0001–1.00 |
| Grape Seed Extract | 0.00001–1.00 |
| Panthenol | 0.005–5.00 |
| Lipoic acid derivative | 1.0–20.0 |
| Total | 100.00000% |

Example 10

Moisturizing Soap Bar for Sensitive Facial Skin

| Materials | Specific Use Concentration (Wt %) |
|---|---|
| Purified Water | 9.3400 |
| Detergents and Cleansing Agents | 48.2000 |
| Buffering Agents | 2.4800 |
| Humectants and Skin Conditioning Agents | 13.0870 |
| Fragrance | 0.2400 |
| Preservatives | 0.0900 |
| Thickeners and Colorants | 25.6600 |
| Vitamin A Palmitate | 0.0050 |
| Vitamin E Acetate | 0.4900 |
| Magnesium Ascorbyl Phosphate | 0.0040 |
| Beta Glucan | 0.0100 |
| Superoxide Dismutase | 0.0040 |
| Grape Seed Extract | 0.1950 |
| Panthenol | 0.1950 |
| Lipoic acid derivative | 1.0–5.0 |
| Total | 100.0000% |

The following compositions are disclosed herein. A first compound of this invention is disclosed as:

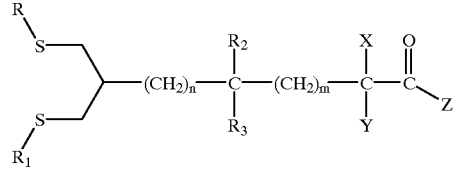

wherein:

R and $R_1$ together form a single bond between the two sulfur atoms to give a 1,2-dithiolane ring;

R and $R_1$ both attach to the same carbonyl group (C=O) to form a 1,3-dithian-2-one ring;

R and $R_1$ both attach to the same carbon atom to form a 1,3-dithiane ring, in particular, thioketals are suggested such as where the connection is $C(Me)_2$, a dimethylketal otherwise known as a 2,2-dimethyl-1,3-dithiane;

R is H, or an acyl group —$COR_4$;

R is a —$CH_2OCOR_4$ or —$CH(R_j)OCOR_4$;

$R_1$ is H, or an acyl group —$COR_4$;

$R_1$ is a —$CH_2OCOR_4$ or —$CH(R_j)OCOR_4$;

R and $R_1$ can simultaneously both be H or acyl (—$COR_4$), or a combination of H and acyl where the H or the acyl can be on either S atom (e.g., R=H, $R_1$=acyl; $R_1$=H, R=acyl);

$R_2$, $R_3$ and $R_4$=any combination of H, heterosubstituted (alcohols, ketones, carboxylates, sulfides, sulfoxides, sulfones, sulfonamides, amines, amides, urethanes, thiourethanes, ureas, carbonates, acetals, ketals, etc.) or unsubstituted normal, branched, cyclic or substituted cyclic hydrocarbons from C1–C20; aryl ring, substituted aryl ring; alkylaryl rings and substituted arylalkyl rings; heterocyclic rings and substituted heterocyclic rings; heteroaromatic rings and substituted heteroaromatic rings; alkylheteroaryl rings and substituted alkylheteroaryl rings; also contained are $NHR_{15}$, $NR_{15}R_{16}$, $OR_{15}$, $SR_{15}$; these groups can contain antioxidant molecules linked through ester or other carbonyl bonds (e.g. ascorbic acid, retinol, vitamin E, vitamin D, hydroquinone, di(t-butylated)hydroxytoluene BHT, t-butylatedhydroxyanisole BHA, t-butylhydroquinone TBHQ, propyl gallate, reduced coenzyme-Q, flavones and isoflavones such as apigenin, quercetin, genistein, and daidzein);

n=0–8 carbons;

m=0–8 carbons;

X=H, OH, or $R_5$, substituted —$OR_6$, —$SR_6$, —$NR_6R_7$, —$PO(OR_6)_2$; —$SOR_6$, —$SO_2R_6$, —$SO_2NR_6R_7$, COOH; $COOR_6$; $CONR_6R_7$, F, Cl, Br, substituted and unsubstituted aryl, heteroaryl, arylalkyl, alkylheteroaryl, heterocyclic, saturated and unsaturated rings;

Y=H, OH, or $R_8$, substituted —$OR_9$, —$SR_9$, —$NR_9R_{10}$, —$PO(OR_9)_2$; —$SOR_9$, —$SO_2R_9$, —$SO_2NR_9R_{10}$, COOH; $COOR_9$; $CONR_9R_{10}$, F, Cl, Br, substituted and unsubstituted aryl, heteroaryl, arylalkyl, alkylheteroaryl, heterocyclic, saturated and unsaturated rings; and Z=H, OH, $OR_{11}$, NHOH, $NH_2$, $NHR_{12}$, $NR_{12}R_{13}$, $SR_{14}$; normal or branched hydrocarbons from C1–C20, aryl ring, substituted aryl ring; alkylaryl rings and substituted arylalkyl rings; heterocyclic rings and substituted heterocyclic rings; heteroaromatic rings and substituted heteroaromatic rings; alkylheteroaryl rings and substituted alkylheteroaryl rings; Z can be other antioxidant molecules linked through ester or other carbonyl bonds (e.g. ascorbic acid, retinol, vitamin E, vitamin D, hydroquinone, di(t-butylated)hydroxytoluene BHT, t-butylatedhydroxyanisole BHA, t-butylhydroquinone TBHQ, propyl gallate, reduced coenzyme-Q, flavones and isoflavones such as apigenin, quercetin, genistein, and daidzein).

A second compound is disclosed herein, having the formula

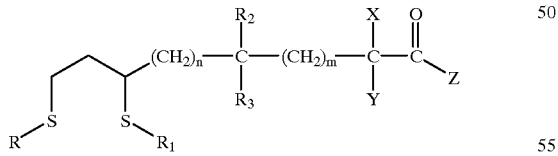

wherein:

R and $R_1$ together form a single bond between the two sulfur atoms to give a 1,2-dithiolane ring;

R and $R_1$ both attach to the same carbonyl group (C=O) to form a 1,3-dithian-2-one ring;

R and $R_1$ both attach to the same carbon atom to form a 1,3-dithiane ring, in particular, thioketals are suggested such as where the connection is C(Me)$_2$, a dimethylketal otherwise known as a 2,2-dimethyl-1,3-dithiane;

R is H, or an acyl group —$COR_4$;

R is a —$CH_2OCOR_4$ or —$CH(R_j)OCOR_4$;

$R_1$ is H, or an acyl group —$COR_4$;

$R_1$ is a —$CH_2OCOR_4$ or —$CH(R_j)OCOR_4$;

R and $R_1$ can simultaneously both be H or acyl ($COR_4$), or a combination of H and acyl where the H or the acyl can be on either S atom (e.g., R=H, $R_1$=acyl; $R_1$=H, R=acyl);

$R_2$, $R_3$ and $R_4$=any combination of H, heterosubstituted (alcohols, ketones, carboxylates, sulfides, sulfoxides, sulfones, sulfonamides, amines, amides, urethanes, thiourethanes, ureas, carbonates, acetals, ketals, etc.) or unsubstituted normal, branched, cyclic or substituted cyclic hydrocarbons from C1–C20; aryl ring, substituted aryl ring; alkylaryl rings and substituted arylalkyl rings; heterocyclic rings and substituted heterocyclic rings; heteroaromatic rings and substituted heteroaromatic rings; alkylheteroaryl rings and substituted alkylheteroaryl rings; also contained are $NHR_{15}$, $NR_{15}R_{16}$, $OR_{15}$, $SR_{15}$; these groups can contain antioxidant molecules linked through ester or other carbonyl bonds (e.g. ascorbic acid, retinol, vitamin E, vitamin D, hydroquinone, di(t-butylated)hydroxytoluene BHT, t-butylatedhydroxyanisole BHA, t-butylhydroquinone TBHQ, propyl gallate, reduced coenzyme-Q, flavones and isoflavones such as apigenin, quercetin, genistein, and daidzein);

n=0–8 carbons;

m=0–8 carbons;

X=H, OH, or $R_5$, substituted —$OR_6$, —$SR_6$, —$NR_6R_7$, —$PO(OR_6)_2$; —$SOR_6$, —$SO_2R_6$, —$SO_2NR_6R_7$, —COOH; —$COOR_6$; —$CONR_6R_7$, —$COR_6$, —F, —Cl, —Br, substituted and unsubstituted aryl, heteroaryl, arylalkyl, alkylheteroaryl, heterocyclic, saturated and unsaturated rings;

Y=H, OH, or $R_8$, substituted —$OR_9$, —$SR_9$, —$NR_9R_{10}$, —$PO(OR_9)_2$; —$SOR_9$, —$SO_2R_9$, —$SO_2NR_9R_{10}$, —COOH; —$COOR_9$; —$CONR_9R_{10}$, —$COR_6$, —F, —Cl, —Br, substituted and unsubstituted aryl, heteroaryl, arylalkyl, alkylheteroaryl, heterocyclic, saturated and unsaturated rings; and Z=H, OH, $OR_{11}$, $NH_2$, NHOH, $NHR_{12}$, $NR_{12}R_{13}$, $SR_{14}$; normal or branched hydrocarbons from C1–C20, aryl ring, substituted aryl ring; alkylaryl rings and substituted arylalkyl rings; heterocyclic rings and substituted heterocyclic rings; heteroaromatic rings and substituted heteroaromatic rings; alkylheteroaryl rings and substituted alkylheteroaryl rings; Z can be other antioxidant molecules linked through ester or other carbonyl bonds (e.g. ascorbic acid, retinol, vitamin E, vitamin D, hydroquinone, di(t-butylated)hydroxytoluene BHT, t-butylatedhydroxyanisole BHA, t-butylhydroquinone TBHQ, propyl gallate, reduced coenzyme-Q, flavones and isoflavones such as apigenin, quercetin, genistein, and daidzein).

The above compounds may be modified in following detail:

1) The first compound where n is an integer from 1–6, and m is an integer from 1–6, $R_2$, $R_3$, X, and Y are hydrogen atoms, and Z is —$OR_0$, wherein $R_0$ is a member of a group consisting of hydrogen and optionally substituted ($C_1$–$C_{15}$)alkyl, arylalkanyl or heteroarylalkyl.

2) The first compound where n is an integer from 1–6, and m is an integer from 1–6, $R_2$, $R_3$ are hydrogen atoms, and either X or Y is an alkoxyl or hydroxyl group —$OR_6$, wherein $R_6$ is a member of a group consisting of hydrogen and optionally substituted ($C_1$–$C_{15}$) hydrocarbons, where further the stereogenic carbon bearing X and Y can be either in R or S configuration, or racemic; and Z is $OR_0$, wherein $R_0$ is a member of a group consisting of hydrogen and optionally substituted ($C_1$–$C_{15}$)alkyl, arylalkanyl or heteroarylalkyl.

3) The first compound where n is an integer from 1–6, and m is an integer from 1–6, $R_2$, $R_3$ are hydrogen atoms, and either X or Y is an amine group —$NR_6R_7$, wherein $R_6$ and $R_7$ are members of a group consisting of hydrogen and optionally substituted ($C_1$–$C_{15}$) hydrocarbons, or can together form a ring, where further the stereogenic carbon bearing X and Y can be either in R or S configuration, or racemic; and Z is $OR_0$, wherein $R_0$ is a member of a group consisting of hydrogen and optionally substituted ($C_1$–$C_{15}$)alkyl, arylalkanyl or heteroarylalkyl.

4) The first compound where n is an integer from 1–6, and m is an integer from 1–6, $R_2$, $R_3$ are hydrogen atoms, and either X or Y is a sulfide or thiol group —$SR_{18}$, wherein $R_{17}$ is a member of a group consisting of hydrogen and optionally substituted ($C_1$–$C_{15}$) hydrocarbons, where further the stereogenic carbon bearing X and Y can be either in R or S configuration, or racemic; and Z is $OR_0$, wherein $R_0$ is a member of a group consisting of hydrogen and optionally substituted ($C_1$–$C_{15}$)alkyl, arylalkanyl or heteroarylalkyl.

5) The first compound where n is an integer from 1–6, and m is an integer from 1–6, $R_2$, $R_3$ are hydrogen atoms, and either X or Y is a sulfone or sulfoxide group —$S(O)_wR_6$, wherein $R_6$ is a member of a group consisting of hydrogen and optionally substituted ($C_1$–$C_{15}$) hydrocarbons, w is an integer from 1 to 2, where further the stereogenic carbon bearing X and Y can be either in R or S configuration, or racemic; and Z is $OR_0$, wherein $R_0$ is a member of a group consisting of hydrogen and optionally substituted ($C_1$–$C_{15}$)alkyl, arylalkanyl or heteroarylalkyl.

6) The first compound where n is an integer from 1–6, and m is an integer from 1–6, $R_2$, $R_3$ are hydrogen atoms, and either X or Y is a sulfonamide group —$SO_2NR_6R_7$, wherein $R_6$ and $R_7$ are members of a group consisting of hydrogen and optionally substituted ($C_1$–$C_{15}$) hydrocarbons, where further the stereogenic carbon bearing X and Y can be either in R or S configuration, or racemic; and Z is $OR_0$, wherein $R_0$ is a member of a group consisting of hydrogen and optionally substituted ($C_1$–$C_{15}$)alkyl, arylalkanyl or heteroarylalkyl.

7) The first compound where n is an integer from 1–6, and m is an integer from 1–6, $R_2$, $R_3$ are hydrogen atoms, and either X or Y is a phosphonate group —$PO(OR_6)_2$, wherein $R_6$ is a member of a group consisting of hydrogen and optionally substituted ($C_1$–$C_{15}$) hydrocarbons, where further the stereogenic carbon bearing X and Y can be either in R or S configuration, or racemic; and Z is $OR_0$, wherein $R_0$ is a member of a group consisting of hydrogen and optionally substituted ($C_1$–$C_{15}$)alkyl, arylalkanyl or heteroarylalkyl.

8) The first compound where n is an integer from 1–6, and m is an integer from 1–6, $R_2$, $R_3$ are hydrogen atoms, and either X or Y is a carboxylate or ester group —$CO_2R_6$, wherein $R_6$ is a member of a group consisting of hydrogen and optionally substituted ($C_1$–$C_{15}$) hydrocarbons, where further the stereogenic carbon bearing X and Y can be either in R or S configuration, or racemic; and Z is $OR_0$, wherein $R_0$ is a member of a group consisting of hydrogen and optionally substituted ($C_1$–$C_{15}$)alkyl, arylalkanyl or heteroarylalkyl.

9) The first compound where n is an integer from 1–6, and m is an integer from 1–6, $R_2$, $R_3$ are hydrogen atoms, and either X or Y is a carboxylate or ester group —$COR_6$, wherein $R_6$ is a member of a group consisting of hydrogen and optionally substituted ($C_1$–$C_{15}$) hydrocarbons, where further the stereogenic carbon bearing X and Y can be either in R or S configuration, or racemic; and Z is $OR_0$, wherein $R_0$ is a member of a group consisting of hydrogen and optionally substituted ($C_1$–$C_{15}$)alkyl, arylalkanyl or heteroarylalkyl.

10) The first compound where n is an integer from 1–6, and m is an integer from 1–6, $R_2$, $R_3$ are hydrogen atoms, and either X or Y is a halogen group —F, —Cl or —Br, where further the stereogenic carbon bearing X and Y can be either in R or S configuration, or racemic; and Z is $OR_0$, wherein $R_0$ is a member of a group consisting of hydrogen and optionally substituted ($C_1$–$C_{15}$)alkyl, arylalkanyl or heteroarylalkyl.

11) The first compound where n is an integer from 1–6, and m is an integer from 1–6, $R_2$, $R_3$ are hydrogen atoms, and either X or Y is a substituted or unsubstituted aryl, heteroaryl, arylalkyl, alkylheteroaryl, heterocyclic, saturated and unsaturated ring or ring bearing group —$R_{18}$, wherein the stereogenic carbon bearing X and Y can be either in R or S configuration, or racemic; and Z is $OR_0$, wherein $R_0$ is a member of a group consisting of hydrogen and optionally substituted ($C_1$–$C_{15}$)alkyl, arylalkanyl or heteroarylalkyl.

12) The compound described in paragraph 2) above where $R_6$ is naught and X and Y together form a carbonyl.

13) The compound described in paragraph 3) above where one or both of $R_6$ and $R_7$ 50 H, and X and Y together form an imine.

14) The compound described in paragraph 1) above where R and $R_1$ are hydrogen atoms; Z is $OR_0$, wherein $R_0$ is a member of a group consisting of hydrogen and optionally ubstituted ($C_1$–$C_{15}$)alkyl, arylalkanyl or heteroarylalkyl.

15) The compound described in paragraph 1) above where one of R and $R_1$ are $COR_4$, and the other is hydrogen; Z is $OR_0$, wherein $R_0$ is a member of a group consisting of hydrogen and optionally substituted ($C_1$–$C_{15}$)alkyl, arylalkanyl or heteroarylalkyl; and $R_4$ is H, heterosubstituted (alcohols, ketones, carboxylates, sulfides, sulfoxides, sulfones, sulfonamides, amines, amides, urethanes, thiourethanes, ureas, carbonates, acetals, ketals, etc.) or unsubstituted normal, branched, cyclic or substituted cyclic hydrocarbons from C1–C20; aryl ring, substituted aryl ring; alkylaryl rings and substituted arylalkyl rings; heterocyclic rings and substituted heterocyclic rings; heteroaromatic rings and substituted heteroaromatic rings; alkylheteroaryl rings and substituted alkylheteroaryl rings. Also contained are $NHR_{19}$, $NR_{19}R_{20}$, $OR_{19}$, $SR_{19}$.

16) The compound described in paragraph 15) above where both of R and $R_1$ are $COR_4$, wherein $R_4$ can be identical.

17) The compound described in paragraph 16) above where $R_4$ of R and $R_1$ are both —$CH_3$.

18) The compound described in paragraph 15) above where $R_4$ of R is different from the $R_4$ of $R_1$.

19) The compound described in paragraph 18) above where $R_4$ of R is —$(CH_2)_gNH_2$—HCl or other acid salts, G is an integer from 0 to 14; and $R_4$ of $R_1$ is —$CH_3$.

20) The compound described in paragraph 18) above where $R_4$ of R is —$CH_2CH_3$; and $R_4$ of $R_1$ is —$CH_3$.

21) The compound described in paragraph 18) above where $R_4$ of R is —$CH_2(CH_2)_w COOH$ (and salts thereof); and $R_4$ of $R_1$ is —$CH_3$. W is an integer from 0 to 24. Preferred compounds occur with azelaic acid (w=7).

22) The compound described in paragraph 18) above where $R_4$ of R is —$(CH_2)_u(CH=CH)_w(CH_2)_v(CH=CH)_h(CH_2)_i$COOH (and salts thereof); and $R_4$ of $R_1$ is —$CH_3$. W is an integer from 0 to 14, u is an integer from 0 to 6, v is an integer from 0 to 6, h is an integer from 0 to 6 and i is an integer from 0 to 6. Preferred compounds occur when v, w and h are 1.

23) The compound described in paragraph 18) above where $R_4$ of R is —$OCH_2CH_3$; and $R_4$ of $R_1$ is —$NHCH_3$.

24) The compound described in paragraph 18) above where $R_4$ of R is —$OCH_2CH_3$; and $R_4$ of $R_1$ is —$N(CH_3)_2$.

25) The compound described in paragraph 18) above where $R_4$ of R is —$SCH_2CH_3$; and $R_4$ of $R_1$ is —$NHCH_3$.

26) The compound described in paragraph 18) above where $R_4$ of R is —$SCH_2CH_3$; and $R_4$ of $R_1$ is —$N(CH_3)_2$.

27) The compound described in paragraph 16) above where $R_4$ of R and $R_1$ are both —$OCH_3$.

28) The compound described in paragraph 16) above where $R_4$ of R and $R_1$ are both —$SCH_3$.

29) The compound described in paragraph 16) above where $R_4$ of R and $R_1$ are both —$NHCH_3$.

30) The compound described in paragraph 16) above where $R_4$ of R and $R_1$ are both —$N(CH_3)_2$.

31) The compound described in paragraph 16) above where $R_4$ of R and $R_1$ are both —$(CH_2)_u(CH=CH)_w(CH_2)_v$COOH (and salts thereof); and $R_4$ of $R_1$ is —$CH_3$. W is an integer from 0 to 14, u is an integer from 0 to 6 and v is an integer from 0 to 6. A preferred example occurs when u and v together equal 7, for azelaic acid.

32) The compound described in paragraph 16) above where $R_4$ of R and $R_1$ are both —$(CH_2)_gNH_2$—HCl or other acid salts. G is an integer from 0 to 14.

33) The compound described in paragraph 1) above where R and $R_1$ join to form a 4-substituted 1,2-dithiolane ring; $R_2$ and $R_3$ are hydrogen; X and Y are hydrogen; Z is $OR_0$, wherein $R_0$ is a member of a group consisting of hydrogen and optionally substituted ($C_1$–$C_{15}$)alkyl, arylalkanyl or heteroarylalkyl.

34) The compound described in paragraph 33) above where $R_0$ is hydrogen, methyl, ethyl, propyl, butyl, isopropyl, (2-methyl)-1-propyl (i.e. isobutyl), pentyl, (2,2-dimethyl)-1-propyl (i.e. neo-pentyl), (3-methyl)-1-butyl (i.e. isovaleryl), R or S or rac (1-methyl)-1-butyl, R or S or rac (2-methyl)-1-butyl, R or S or rac (1-methyl)-1-pentyl, R or S or rac (2-methyl)-1-pentyl, R or S or rac (3-methyl)-1-pentyl, (4-methyl)-1-pentyl, and so on. Preferred $R_0$ derivatives are ethyl and propyl.

35) The compounds described in paragraphs 1) through 33) above where Z=$NHR_0$. Preferred $R_0$ derivatives are ethyl, propyl, 2-(N,N'-dimethylamino)ethyl- (and acid salts thereof), and aryl or heteroaryl rings.

36) The compounds described in paragraphs 1) through 33) above where Z=$SR_0$. Preferred $R_0$ derivatives are ethyl, propyl, 2-(N,N'-dimethylamino)ethyl- (and acid salts thereof), and aryl or heteroaryl rings.

37) The compounds described in paragraphs 1) through 33) above where $R_0$ is an antioxidant such as ascorbic acid (Vitamin C), retinol (Pro-Vitamin A), vitamin E (the various tocopherols and tocophatrienes), vitamin D, hydroquinone, di(t-butylated)hydroxytoluene BHT, t-butylatedhydroxyanisole BHA, t-butylhydroquinone TBHQ, propyl gallate, reduced coenzyme-Q, flavones and isoflavones such as apigenin, quercetin, genistein, and daidzein.

38) The second compound where n is an integer from 1–6, and m is an integer from 1–6, $R_2$, $R_3$, X, and Y are hydrogen atoms, and Z is —$OR_0$, wherein $R_0$ is a member of a group consisting of hydrogen and optionally substituted ($C_1$–$C_{15}$)alkyl, arylalkanyl or heteroarylalkyl.

39) The second compound where n is an integer from 1–6, and m is an integer from 1–6, $R_2$, $R_3$ are hydrogen atoms, and either X or Y is an alkoxyl or hydroxyl group —$OR_6$, wherein $R_6$ is a member of a group consisting of hydrogen and optionally substituted ($C_1$–$C_{15}$) hydrocarbons, where further the stereogenic carbon bearing X and Y can be either in R or S configuration, or racemic; and Z is $OR_0$, wherein $R_0$ is a member of a group consisting of hydrogen and optionally substituted ($C_1$–$C_{15}$)alkyl, arylalkanyl or heteroarylalkyl.

40) The second compound where n is an integer from 1–6, and m is an integer from 1–6, $R_2$, $R_3$ are hydrogen atoms, and either X or Y is an amine group —$NR_6R_7$, wherein $R_6$ and $R_7$ are members of a group consisting of hydrogen and optionally substituted ($C_1$–$C_{15}$) hydrocarbons, or can together form a ring, where further the stereogenic carbon bearing X and Y can be either in R or S configuration, or racemic; and Z is $OR_0$, wherein $R_0$ is a member of a group consisting of hydrogen and optionally substituted ($C_1$–$C_{15}$)alkyl, arylalkanyl or heteroarylalkyl.

41) The second compound where n is an integer from 1–6, and m is an integer from 1–6, $R_2$, $R_3$ are hydrogen atoms, and either X or Y is a sulfide or thiol group —$SR_{18}$, wherein $R_{17}$ is a member of a group consisting of hydrogen and optionally substituted ($C_1$–$C_{15}$) hydrocarbons, where further the stereogenic carbon bearing X and Y can be either in R or S configuration, or racemic; and Z is $OR_0$, wherein $R_0$ is a member of a group consisting of hydrogen and optionally substituted ($C_1$–$C_{15}$)alkyl, arylalkanyl or heteroarylalkyl.

42) The second compound where n is an integer from 1–6, and m is an integer from 1–6, $R_2$, $R_3$ are hydrogen atoms, and either X or Y is a sulfone or sulfoxide group —$S(O)_w R_6$, wherein $R_6$ is a member of a group consisting of hydrogen and optionally substituted ($C_1$–$C_{15}$) hydrocarbons, w is an integer from 1 to 2, where further the stereogenic carbon bearing X and Y can be either in R or S configuration, or racemic; and Z is $OR_0$, wherein $R_0$ is a member of a group consisting of hydrogen and optionally substituted ($C_1$–$C_{15}$)alkyl, arylalkanyl or heteroarylalkyl.

43) The second compound where n is an integer from 1–6, and m is an integer from 1–6, $R_2$, $R_3$ are hydrogen atoms, and either X or Y is a sulfonamide group —$SO_2NR_6R_7$, wherein $R_6$ and $R_7$ are members of a group consisting of hydrogen and optionally substituted ($C_1$–$C_{15}$) hydrocarbons, where further the stereogenic carbon bearing X and Y can be either in R or S configuration, or racemic; and Z is $OR_0$, wherein $R_0$ is a member of a group consisting of hydrogen and optionally substituted ($C_1$–$C_{15}$)alkyl, arylalkanyl or heteroarylalkyl.

44) The second compound where n is an integer from 1–6, and m is an integer from 1–6, $R_2$, $R_3$ are hydrogen atoms, and either X or Y is a phosphonate group —$PO(OR_6)_2$, wherein $R_6$ is a member of a group consisting of hydrogen and optionally substituted ($C_1$–$C_{15}$) hydrocarbons, where further the stereogenic carbon bearing X and Y can be either in R or S configuration, or racemic; and Z is $OR_0$, wherein $R_0$ is a member of a group consisting of hydrogen and optionally substituted ($C_1$–$C_{15}$)alkyl, arylalkanyl or heteroarylalkyl.

45) The second compound where n is an integer from 1–6, and m is an integer from 1–6, $R_2$, $R_3$ are hydrogen atoms, and either X or Y is a carboxylate or ester group —$CO_2R_6$, wherein $R_6$ is a member of a group consisting of hydrogen and optionally substituted ($C_1$–$C_{15}$) hydrocarbons, where further the stereogenic carbon bearing X and Y can be either in R or S configuration, or racemic; and Z is $OR_0$, wherein $R_0$ is a member of a group consisting of hydrogen and optionally substituted ($C_1$–$C_{15}$)alkyl, arylalkanyl or heteroarylalkyl.

46) The second compound where n is an integer from 1–6, and m is an integer from 1–6, $R_2$, $R_3$ are hydrogen atoms, and either X or Y is a carboxylate or ester group —$COR_6$, wherein $R_6$ is a member of a group consisting of hydrogen and optionally substituted ($C_1$–$C_{15}$) hydrocarbons, where further the stereogenic carbon bearing X and Y can be either in R or S configuration, or racemic; and Z is $OR_0$, wherein $R_0$ is a member of a group consisting of hydrogen and optionally substituted ($C_1$–$C_{15}$)alkyl, arylalkanyl or heteroarylalkyl.

47) The second compound where n is an integer from 1–6, and m is an integer from 1–6, $R_2$, $R_3$ are hydrogen atoms, and either X or Y is a halogen group —F, —Cl or —Br, where further the stereogenic carbon bearing X and Y can be either in R or S configuration, or racemic; and Z is $OR_0$, wherein $R_0$ is a member of a group consisting of hydrogen and optionally substituted ($C_1$–$C_{15}$)alkyl, arylalkanyl or heteroarylalkyl.

48) The second compound where n is an integer from 1–6, and m is an integer from 1–6, $R_2$, $R_3$ are hydrogen atoms, and either X or Y is a substituted or unsubstituted aryl, heteroaryl, arylalkyl, alkylheteroaryl, heterocyclic, saturated and unsaturated ring or ring bearing group —$R_{18}$, wherein the stereogenic carbon bearing X and Y can be either in R or S configuration, or racemic; and Z is $OR_0$, wherein $R_0$ is a member of a group consisting of hydrogen and optionally substituted ($C_1$–$C_{15}$)alkyl, arylalkanyl or heteroarylallyl.

49) The compound described in paragraph 39) above where $R_6$ is naught and X and Y together form a carbonyl.

50) The compound described in paragraph 40) above where one or both of $R_6$ and $R_7$=H, and X and Y together form an imine.

51) The compound described in paragraph 38) above where R and $R_1$ are hydrogen atoms; Z is $OR_0$, wherein $R_0$ is a member of a group consisting of hydrogen and optionally substituted ($C_1$–$C_{15}$)alkyl, arylalkanyl or heteroarylalkyl.

52) The compound described in paragraph 38) above where one of R and $R_1$ are $COR_4$, and the other is hydrogen; Z is $OR_0$, wherein $R_0$ is a member of a group consisting of hydrogen and optionally substituted ($C_1$–$C_{15}$)alkyl, arylalkanyl or heteroarylalkyl; and $R_4$ is H, heterosubstituted (alcohols, ketones, carboxylates, sulfides, sulfoxides, sulfones, sulfonamides, amines, amides, urethanes, thiourethanes, ureas, carbonates, acetals, ketals, etc.) or unsubstituted normal, branched, cyclic or substituted cyclic hydrocarbons from C1–C20; aryl ring, substituted aryl ring; alkylaryl rings and substituted arylalkyl rings; heterocyclic rings and substituted heterocyclic rings; heteroaromatic rings and substituted heteroaromatic rings; alkylheteroaryl rings and substituted alkylheteroaryl rings. Also contained are $NHR_{19}$, $NR_{19}R_{20}$, $OR_{19}$, $SR_{19}$.

53) The compound described in paragraph 52) above where both of R and $R_1$ are $COR_4$, wherein $R_4$ can be identical.

54) The compound described in paragraph 53) above where $R_4$ of R and $R_1$ are both —$CH_3$.

55) The compound described in paragraph 52) above where $R_4$ of R is different from the $R_4$ of $R_1$.

56) The compound described in paragraph 55) above where $R_4$ of R is —$(CH_2)_g NH_2$—HCl or other acid salts, G is an integer from 0 to 14; and $R_4$ of $R_1$ is —$CH_3$.

57) The compound described in paragraph 55) above where $R_4$ of $R_1$ is —$(CH_2)_g NH_2$—HCl or other acid salts, G is an integer from 0 to 14; and $R_4$ of R is —$CH_3$.

58) The compound described in paragraph 55) above where $R_4$ of R is —$CH_2CH_3$; and $R_4$ of $R_1$ is —$CH_3$.

59) The compound described in paragraph 55) above where $R_4$ of $R_1$ is —$CH_2CH_3$; and $R_4$ of R is —$CH_3$.

60) The compound described in paragraph 55) above where $R_4$ of R is —$CH_2(CH_2)_w COOH$ (and salts thereof); and $R_4$ of $R_1$ is —$CH_3$. W is an integer from 0 to 14.

61) The compound described in paragraph 55) above where $R_4$ of $R_1$ is —$CH_2(CH_2)_w COOH$ (and salts thereof); and $R_4$ of R is —$CH_3$. W is an integer from 0 to 14. When w=6, the ester is from preferred azelaic acid.

62) The compound described in paragraph 55) above where $R_4$ of R is —$(CH_2)_u(CH=CH)_w(CH_2)_v(CH=CH)_h(CH_2)_i$ COOH (and salts thereof); and $R_4$ of $R_1$ is —$CH_3$. W is an integer from 0 to 14, u is an integer from 0 to 6, v is an integer from 0 to 6, h is an integer from 0 to 6 and i is an integer from 0 to 6. Preferred compounds occur when v, w and h are 1.

63) The compound described in paragraph 55) above where $R_4$ of $R_1$ is —$(CH_2)_u(CH=CH)_w(CH_2)_v(CH=CH)_h(CH_2)_iCH_3$; and $R_4$ of R is —$CH_3$. W is an integer from 0 to 14, u is an integer from 0 to 6, v is an integer from 0 to 6, h is an integer from 0 to 6 and i is an integer from 0 to 6. Preferred compounds occur linoleic acid esters where v, w and h are 1, while u=7 and I=4.

64) The compound described in paragraph 55) above where $R_4$ of R is —$(CH_2)_u(CH=CH)_w(CH_2)_v(CH=CH)_h(CH_2)_iCH_3$; and $R_4$ of $R_1$ is —$CH_3$. W is an integer from 0 to 14, u is an integer from 0 to 6, v is an integer from 0 to 6, h is an integer from 0 to 6 and i is an integer from 0 to 6. Preferred compounds occur linoleic acid esters where v, w and h are 1, while u=7 and I=4.

65) The compound described in paragraph 55) above where $R_4$ of R is —$OCH_2CH_3$; and $R_4$ of $R_1$ is —$NHCH_3$.

66) The compound described in paragraph 55) above where P4 of $R_1$ is —$OCH_2CH_3$; and $R_4$ of R is —$NHCH_3$.

67) The compound described in paragraph 55) above where $R_4$ of R is —$OCH_2CH_3$; and $R_4$ of $R_1$ is —$N(CH_3)_2$.

68) The compound described in paragraph 55) above where $R_4$ of $R_1$ is —$OCH_2CH_3$; and $R_4$ of R is —$N(CH_3)_2$.

69) The compound described in paragraph 55) above where $R_4$ of R is —$SCH_2CH_3$; and $R_4$ of $R_1$ is —$NHCH_3$.

70) The compound described in paragraph 55) above where $R_4$ of $R_1$ is —$SCH_2CH_3$; and $R_4$ of R is —$NHCH_3$.

71) The compound described in paragraph 55) above where $R_4$ of R is —$SCH_2CH_3$; and $R_4$ of $R_1$ is —$N(CH_3)_2$.

72) The compound described in paragraph 55) above where $R_4$ of $R_1$ is —$SCH_2CH_3$; and $R_4$ of R is —$N(CH_3)_2$.

73) The compound described in paragraph 53) above where $R_4$ of R and $R_1$ are both —$OCH_3$.

74) The compound described in paragraph 53) above where $R_4$ of R and $R_1$ are both —$SCH_3$.

75) The compound described in paragraph 53) above where $R_4$ of R and $R_1$ are both —$NHCH_3$.

76) The compound described in paragraph 53) above where $R_4$ of R and $R_1$ are both —$N(CH_3)_2$.

77) The compound described in paragraph 53) above where $R_4$ of R and $R_1$ are both —$(CH_2)_u(CH=CH)_w(CH_2)_v$ COOH (and salts thereof); W is an integer from 0 to 14, u is an integer from 0 to 6 and v is an integer from 0 to 6.

78) The compound described in paragraph 53) above where $R_4$ of R and $R_1$ are both —$(CH_2)_g NH_2$—HCl or other acid salts. G is an integer from 0 to 14.

79) The compound described in paragraph 53) above where $R_4$ of R and $R_1$ are both —$CH_2CH_3$.
80) The compound described in paragraph 53) above where $R_4$ of R and $R_1$ are both —$(CH_2)_4CH_3$.
81) The compound described in paragraph 53) above where $R_4$ of R and $R_1$ are both R or S or rac —$CH_eOH(CH_2)_b$ $(CH_3)_d$, where b is an integer from 0 to 8 and d is an integer from 0 to 1. When both b and d are 0, e=2; d can only be 0 when b is 0.
82) The compound described in paragraph 53) above where $R_4$ of R and $R_1$ are both —$(CH_2)_fCO2H$ (and salts thereof), in which F is an integer from 1 to 24, where 7 is preferred (azaleic acid).
83) The compound described in paragraph 38) above where R and $R_1$ join to form a 3-substituted 1,2-dithiolane ring; $R_2$ and $R_3$ are hydrogen; X and Y are hydrogen; Z is $OR_0$, wherein $R_0$ is a member of a group consisting of hydrogen and optionally substituted ($C_1$–$C_{15}$)alkyl, arylalkanyl or heteroarylalkyl.
84) The compound described in paragraph 83) above where $R_0$ is hydrogen, methyl, ethyl, propyl, butyl, isopropyl, (2-methyl)-1-propyl (i.e. isobutyl), pentyl, (2,2-dimethyl)-1-propyl (i.e. neo-pentyl), (3-methyl)-1-butyl (i.e. isovaleryl), R or S or rac (l-methyl)-1-butyl, R or S or rac (2-methyl)-1-butyl, R or S or rac (1-methyl)-1-pentyl, R or S or rac (2-methyl)-1-pentyl, R or S or rac (3-methyl)-1-pentyl, (4-methyl)-1-pentyl, and so forth. Preferred $R_0$ derivatives are ethyl and propyl.
85) The compounds described in paragraphs 38) through 83) above where $Z=NHR_0$. Preferred $R_0$ derivatives are ethyl, propyl, 2-(N,N'-dimethylamino)ethyl- (and acid salts thereof), and aryl or heteroaryl rings.
86) The compounds described in paragraphs 38) through 83) above where $Z=SR_0$. Preferred $R_0$ derivatives are ethyl, propyl, 2-(N,N'-dimethylamino)ethyl- (and acid salts thereof), and aryl or heteroaryl rings.
87) The compounds described in paragraphs 38) through 83) above where $R_0$ is an antioxidant such as ascorbic acid (Vitamin C), retinol (Pro-Vitamin A), vitamin E (the various tocopherols and tocophatrienes), vitamin D, hydroquinone, di(t-butylated)hydroxytoluene BHT, t-butylatedhydroxyanisole BHA, t-butylhydroquinone TBHQ, propyl gallate, reduced coenzyme-Q, flavones and isoflavones such as apigenin, quercetin, genistein, and daidzein.
88) The first compound where n is an integer from 1–6, and m is an integer from 1–6, $R_2$ or $R_3$, and X and Y are hydrogen atoms, one of $R_2$ or $R_3$ is a member of a group consisting of optionally substituted ($C_1$–$C_{15}$)alkyl, arylalkanyl or heteroarylalkyl in which the stereogenic center to which the $R_2$ or $R_3$ is attached is either of R or S configuration, or is a racemic mixture; and Z is —$OR_0$, wherein $R_0$ is a member of a group consisting of hydrogen and optionally substituted ($C_1$–$C_{15}$)alkyl, arylalkanyl or heteroarylalkyl. Preferred examples include where $R_2$ or $R_3$ are the (2-methyl)-1-propyl (i.e. isobutyl) group, the benzyl moiety, a 2,3 or 4-pyridylmethylenyl group, a 2 or 3 furylmethylenyl group, a cyclopropylmethylenyl group, and so forth.
89) The compound described in paragraph 88) above where $R_0$ is hydrogen, methyl, ethyl, propyl, butyl, isopropyl, (2-methyl)-1-propyl (i.e. isobutyl), pentyl, (2,2-dimethyl)-1-propyl (i.e. neo-pentyl), (3-methyl)-1-butyl (i.e. isovaleryl), R or S or rac (1-methyl)-1-butyl, R or S or rac (2-methyl)-1-butyl, R or S or rac (1-methyl)-1-pentyl, R or S or rac (2-methyl)-1-pentyl, R or S or rac (3-methyl)-1-pentyl, (4-methyl)-1-pentyl, and so forth. Preferred $R_0$ derivatives are ethyl, propyl, and isobutyl.
90) The compound described in paragraph 89) above where n is an integer from 1–6, and m is an integer from 1–6; either X or Y is an alkoxyl or hydroxyl group —$OR_6$, wherein $R_6$ is a member of a group consisting of hydrogen and optionally substituted ($C_1$–$C_{15}$) hydrocarbons, where further the stereogenic carbon bearing X and Y can be either in R or S configuration, or racemic.
91) The compound described in paragraph 89) above where n is an integer from 1–6, and m is an integer from 1–6; either X or Y is an amine group —$NR_6R_7$, wherein $R_6$ and $R_7$ are members of a group consisting of hydrogen and optionally substituted ($C_1$–$C_{15}$) hydrocarbons, or can together form a ring, where further the stereogenic carbon bearing X and Y can be either in R or S configuration, or racemic.
92) The compound described in paragraph 89) above where n is an integer from 1–6, and m is an integer from 1–6; either X or Y is a sulfide or thiol group —$SR_{18}$, wherein $R_{17}$ is a member of a group consisting of hydrogen and optionally substituted ($C_1$–$C_{15}$) hydrocarbons, where further the stereogenic carbon bearing X and Y can be either in R or S configuration, or racemic.
93) The compound described in paragraph 89) above where n is an integer from 1–6, and m is an integer from 1–6; either X or Y is a sulfone or sulfoxide group —$S(O)_wR_6$, wherein $R_6$ is a member of a group consisting of hydrogen and optionally substituted ($C_1$–$C_{15}$) hydrocarbons, w is an integer from 1 to 2, where further the stereogenic carbon bearing X and Y can be either in R or S configuration, or racemic.
94) The compound described in paragraph 89) above where n is an integer from 1–6, and m is an integer from 1–6; either X or Y is a sulfonamide group —$SO_2NR_6R_7$, wherein $R_6$ and $R_7$ are members of a group consisting of hydrogen and optionally substituted ($C_1$–$C_{15}$) hydrocarbons, where further the stereogenic carbon bearing X and Y can be either in R or S configuration, or racemic.
95) The compound described in paragraph 89) above where n is an integer from 1–6, and m is an integer from 1–6; either X or Y is a phosphonate group —$PO(OR_6)2$, wherein $R_6$ is a member of a group consisting of hydrogen and optionally substituted ($C_1$–$C_{15}$) hydrocarbons, where further the stereogenic carbon bearing X and Y can be either in R or S configuration, or racemic.
96) The compound described in paragraph 89) above where n is an integer from 1–6, and m is an integer from 1–6; either X or Y is a carboxylate or ester group $CO_2R_6$, wherein $R_6$ is a member of a group consisting of hydrogen and optionally substituted ($C_1$–$C_{15}$) hydrocarbons, where further the stereogenic carbon bearing X and Y can be either in R or S configuration, or racemic.
97) The compound described in paragraph 89) above where n is an integer from 1–6, and m is an integer from 1–6; either X or Y is a carboxylate or ester group —$COR_6$, wherein $R_6$ is a member of a group consisting of hydrogen and optionally substituted ($C_1$–$C_{15}$) hydrocarbons, where further the stereogenic carbon bearing X and Y can be either in R or S configuration, or racemic.
98) The compound described in paragraph 89) above where n is an integer from 1, and m is an integer from 1–6; either X or Y is a halogen group —F, —Cl or —Br, where further the stereogenic carbon bearing X and Y can be either in R or S configuration, or racemic.
99) The compound described in paragraph 89) above where n is an integer from 1–6, and m is an integer from 1–6; either X or Y is a substituted or unsubstituted aryl, heteroaryl, arylalkyl, alkylheteroaryl, heterocyclic, saturated and unsaturated ring or ring bearing group $R_{18}$, wherein the stereogenic carbon bearing X and Y can be either in R or S configuration, or racemic.

100) The compound described in paragraph 90) above where $R_6$ is naught and X and Y together form a carbonyl.

101) The compound described in paragraph 91) above where one or both of $R_6$ and $R_7$=H, and X and Y together form an imine.

102) The compound described in paragraph 89) above where R and $R_1$ are hydrogen atoms.

103) The compound described in paragraph 89) above where one of R and $R_1$ are $COR_4$, and the other is hydrogen; $R_4$ is optionally substituted (alcohols, ketones, carboxylates, sulfides, sulfoxides, sulfones, sulfonamides, amines, amides, urethanes, thiourethanes, ureas, carbonates, acetals, ketals, etc.) or normal, branched, cyclic or substituted cyclic hydrocarbons from C1–C20; aryl ring, substituted aryl ring; alkylaryl rings and substituted arylalkyl rings; heterocyclic rings and substituted heterocyclic rings; heteroaromatic rings and substituted heteroaromatic rings; alkylheteroaryl rings and substituted alkylheteroaryl rings. Also contained are $NHR_{19}$, $NR_{19}R_{20}$, $OR_{19}$, $SR_{19}$.

104) The compound described in paragraph 103) above where both of R and $R_1$ are $COR_4$, wherein $R_4$ can be identical.

105) The compound described in paragraph 104) above where $R_4$ of R and $R_1$ are both —$CH_3$.

106) The compound described in paragraph 103) above where $R_4$ of R is different from the $R_4$ of $R_1$.

107) The compound described in paragraph 106) above where $R_4$ of R is —$(CH_2)_gNH_2$—HCl or other acid salts, G is an integer from 0 to 14; and $R_4$ of $R_1$ is —$CH_3$.

108) The compound described in paragraph 106) above where $R_4$ of R is —$CH_2CH_3$; and $R_4$ of $R_1$ is —$CH_3$.

109) The compound described in paragraph 106) above where $R_4$ of R is —$CH_2(CH_2)_w COOH$ (and salts thereof); and $R_4$ of $R_1$ is —$CH_3$. W is an integer from 0 to 24. Preferred compounds occur with azelaic acid (w=7).

110) The compound described in paragraph 106) above where $R_4$ of R is —$(CH_2)_u(CH=CH)_w(CH_2)_v(CH=CH)_h (CH_2)_i COOH$ (and salts thereof); and $R_4$ of $R_1$ is —$CH_3$. W is an integer from 0 to 14, u is an integer from 0 to 6, v is an integer from 0 to 6, h is an integer from 0 to 6 and i is an integer from 0 to 6. Preferred compounds occur when v, w and h are 1.

111) The compound described in paragraph 106) above where $R_4$ of R is —$OCH_2CH_3$; and $R_4$ of $R_1$ is —$NHCH_3$.

112) The compound described in paragraph 106) above where $R_4$ of R is —$OCH_2CH_3$; and $R_4$ of $R_1$ is —$N(CH_3)_2$.

113) The compound described in paragraph 106) above where $R_4$ of R is —$SCH_2CH_3$; and $R_4$ of $R_1$ is —$NHCH_3$.

114) The compound described in paragraph 106) above where $R_4$ of R is —$SCH_2CH_3$; and $R_4$ of $R_1$ is —$N(CH_3)_2$.

115) The compound described in paragraph 104) above where $R_4$ of R and $R_1$ are both —$OCH_3$.

116) The compound described in paragraph 104) above where $R_4$ of R and $R_1$ are both —$SCH_3$.

117) The compound described in paragraph 104) above where $R_4$ of R and $R_1$ are both —$NHCH_3$.

118) The compound described in paragraph 104) above where $R_4$ of R and $R_1$ are both —$N(CH_3)_2$.

119) The compound described in paragraph 104) above where $R_4$ of R and $R_1$ are both —$(CH_2)_u(CH=CH)_w(CH_2)_v COOH$ (and salts thereof); and $R_4$ of $R_1$ is —$CH_3$. W is an integer from 0 to 14, u is an integer from 0 to 6 and v is an integer from 0 to 6. A preferred example occurs when u and v together equal 7, for azelaic acid.

120) The compound described in paragraph 104) above where $R_4$ of R and $R_1$ are both —$(CH_2)_gNH_2$—HCl or other acid salts. G is an integer from 0 to 14.

121) The compound described in paragraph 89) above where R and $R_1$ join to form a 4-substituted 1,2-dithiolane ring; X and Y are hydrogen.

122) The compounds described in paragraphs 88 through 121 above where $Z=NHR_0$. Preferred $R_0$ derivatives are ethyl, propyl, 2-(N,N'-dimethylamino)ethyl- (and acid salts thereof), and aryl or heteroaryl rings.

123) The compounds described in paragraphs 88 through 121 above where $Z=SR_0$. Preferred $R_0$ derivatives are ethyl, propyl, 2-(N,N'-dimethylamino)ethyl- (and acid salts thereof), and aryl or heteroaryl rings.

124) The compounds described in paragraphs 88 through 121 above where $R_0$ is an antioxidant such as ascorbic acid (Vitamin C), retinol (Pro-Vitamin A), vitamin E (the various tocopherols and tocophatrienes), vitamin D, hydroquinone, di(t-butylated)hydroxytoluene BHT, t-butylatedhydroxyanisole BHA, t-butylhydroquinone TBHQ, propyl gallate, reduced coenzyme-Q, flavones and isoflavones such as apigenin, quercetin, genistein, and daidzein.

125) The second compound where n is an integer from 1–6, and m is an integer from 1–6, $R_2$ or $R_3$, and X and Y are hydrogen atoms, one of $R_2$ or $R_3$ is a member of a group consisting of optionally substituted $(C_1–C_{15})$alkyl, arylalkanyl or heteroarylalkyl in which the stereogenic center to which the $R_2$ or $R_3$ is attached is either of R or S configuration, or is a racemic mixture; and Z is —$OR_0$, wherein $R_0$ is a member of a group consisting of hydrogen and optionally substituted $(C_1–C_{15})$alkyl, arylalkanyl or heteroarylalkyl. Preferred examples include where $R_2$ or $R_3$ are the (2-methyl)-1-propyl (i.e. isobutyl) group, the benzyl moiety, a 2,3 or 4-pyridylmethylenyl group, a 2 or 3 furylmethylenyl group, a cyclopropylmethylenyl group, and so forth.

126) The compound described in paragraph 125) above where $R_0$ is hydrogen, methyl, ethyl, propyl, butyl, isopropyl, (2-methyl)-1-propyl (i.e. isobutyl), pentyl, (2,2-dimethyl)-1-propyl (i.e. neo-pentyl), (3-methyl)-1-butyl (i.e. isovaleryl), R or S or rac (1-methyl)-1-butyl, R or S or rac (2-methyl)-1-butyl, R or S or rac (1-methyl)-1-pentyl, R or S or rac (2-methyl)-1-pentyl, R or S or rac (3-methyl)-1-pentyl, (4-methyl)-1-pentyl, and so forth. Preferred $R_0$ derivatives are ethyl, propyl, and isobutyl.

127) The compound described in paragraph 126) above where n is an integer from 1–6, and m is an integer from 1–6; either X or Y is an alkoxyl or hydroxyl group —$OR_6$, wherein $R_6$ is a member of a group consisting of hydrogen and optionally substituted $(C_1–C_{15})$ hydrocarbons, where further the stereogenic carbon bearing X and Y can be either in R or S configuration, or racemic.

128) The compound described in paragraph 126) above where n is an integer from 1–6, and m is an integer from 1–6; either X or Y is an amine group —$NR_6R_7$, wherein $R_6$ and $R_7$ are members of a group consisting of hydrogen and optionally substituted $(C_1–C_{15})$ hydrocarbons, or can together form a ring, where further the stereogenic carbon bearing X and Y can be either in R or S configuration, or racemic.

129) The compound described in paragraph 126) above where n is an integer from 1–6, and m is an integer from 1–6; either X or Y is a sulfide or thiol group —$SR_{18}$, wherein $R_{17}$ is a member of a group consisting of hydrogen and optionally substituted ($C_1$–$C_{15}$) hydrocarbons, where further the stereogenic carbon bearing X and Y can be either in R or S configuration, or racemic.

130) The compound described in paragraph 126) above where n is an integer from 1–6, and m is an integer from 1–6; either X or Y is a sulfone or sulfoxide group —$S(O)_wR_6$, wherein $R_6$ is a member of a group consisting of hydrogen and optionally substituted ($C_1$–$C_{15}$) hydrocarbons, w is an integer from 1 to 2, where further the stereogenic carbon bearing X and Y can be either in R or S configuration, or racemic.

131) The compound described in paragraph 126) above where n is an integer from 1–6, and m is an integer from 1–6; either X or Y is a sulfonamide group —$SO_2NR_6R_7$, wherein $R_6$ and $R_7$ are members of a group consisting of hydrogen and optionally substituted ($C_1$–$C_{15}$) hydrocarbons, where further the stereogenic carbon bearing X and Y can be either in R or S configuration, or racemic.

132) The compound described in paragraph 126) above where n is an integer from 1–6, and m is an integer from 1–6; either X or Y is a phosphonate group —$PO(OR_6)_2$, wherein $R_6$ is a member of a group consisting of hydrogen and optionally substituted ($C_1$–$C_{15}$) hydrocarbons, where further the stereogenic carbon bearing X and Y can be either in R or S configuration, or racemic.

133) The compound described in paragraph 126) above where n is an integer from 1–6, and m is an integer from 1–6; either X or Y is a carboxylate or ester group —$CO_2R_6$, wherein $R_6$ is a member of a group consisting of hydrogen and optionally substituted ($C_1$–$C_{15}$) hydrocarbons, where further the stereogenic carbon bearing X and Y can be either in R or S configuration, or racemic.

134) The compound described in paragraph 126) above where n is an integer from 1–6, and m is an integer from 1–6; either X or Y is a carboxylate or ester group —$COR_6$, wherein $R_6$ is a member of a group consisting of hydrogen and optionally substituted ($C_1$–$C_{15}$) hydrocarbons, where further the stereogenic carbon bearing X and Y can be either in R or S configuration, or racemic.

135) The compound described in paragraph 126) above where n is an integer from 1–6, and m is an integer from 1–6; either X or Y is a halogen group —F, —Cl or —Br, where further the stereogenic carbon bearing X and Y can be either in R or S configuration, or racemic.

136) The compound described in paragraph 126) above where n is an integer from 1–6, and m is an integer from 1–6; either X or Y is a substituted or unsubstituted aryl, heteroaryl, arylalkyl, alkylheteroaryl, heterocyclic, saturated and unsaturated ring or ring bearing group —$R_{18}$, wherein the stereogenic carbon bearing X and Y can be either in R or S configuration, or racemic.

137) The compound described in paragraph 127) above where $R_6$ is naught and X and Y together form a carbonyl.

138) The compound described in paragraph 128) above where One or both of $R_6$ and $R_7$=H, and X and Y together form an imine.

139) The compound described in paragraph 126) above where R and $R_1$ are hydrogen atoms.

140) The compound described in paragraph 126) above where one of R and $R_1$ are $COR_4$, and the other is hydrogen; $R_4$ is optionally substituted (alcohols, ketones, carboxylates, sulfides, sulfoxides, sulfones, sulfonamides, amines, amides, urethanes, thiourethanes, ureas, carbonates, acetals, ketals, etc.) or normal, branched, cyclic or substituted cyclic hydrocarbons from C1–C20; aryl ring, substituted aryl ring; alkylaryl rings and substituted arylalkyl rings; heterocyclic rings and substituted heterocyclic rings; heteroaromatic rings and substituted heteroaromatic rings; alkylheteroaryl rings and substituted alkylheteroaryl rings. Also contained are $NHR_{19}$, $NR_{19}R_{20}$, $OR_{19}$, $SR_{19}$.

141) The compound described in paragraph 140) above where both of R and $R_1$ are $COR_4$, wherein $R_4$ can be identical.

142) The compound described in paragraph 141) above where $R_4$ of R and $R_1$ are both —$CH_3$.

143) The compound described in paragraph 140) above where $R_4$ of R is different from the $R_4$ of $R_1$.

144) The compound described in paragraph 143) above where $R_4$ of R is —$(CH_2)_gNH_2$—HCl or other acid salts, G is an integer from 0 to 14; and $R_4$ of $R_1$ is —$CH_3$.

145) The compound described in paragraph 143) above where $R_4$ of $R_1$ is —$(CH_2)_gNH_2$—HCl or other acid salts, G is an integer from 0 to 14; and $R_4$ of R is —$CH_3$.

146) The compound described in paragraph 143) above where P4 of R is —$CH_2CH_3$; and $R_4$ of $R_1$ is —$CH_3$.

147) The compound described in paragraph 143) above where $R_4$ of $R_1$ is —$CH_2CH_3$; and $R_4$ of R is —$CH_3$.

148) The compound described in paragraph 143) above where $R_4$ of R is —$CH_2(CH_2)_wCOOH$ (and salts thereof); and $R_4$ of R is —$CH_3$. W is an integer from 0 to 14.

149) The compound described in paragraph 143) above where $R_4$ of $R_1$ is —$CH_2(CH_2)_wCOOH$ (and salts thereof); and $R_4$ of R is —$CH_3$. W is an integer from 0 to 14. When w=6, the ester is from preferred azelaic acid.

150) The compound described in paragraph 143) above where $R_4$ of R is —$(CH_2)_u(CH=CH)_w(CH_2)_v(CH=CH)_h(CH_2)_iCOOH$ (and salts thereof); and $R_4$ of $R_1$ is —$CH_3$. W is an integer from 0 to 14, u is an integer from 0 to 6, v is an integer from 0 to 6, h is an integer from 0 to 6 and i is an integer from 0 to 6. Preferred compounds occur when v, w and h are 1.

151) The compound described in paragraph 143) above where $R_4$ of $R_1$ is —$(CH_2)_u(CH=CH)_w(CH_2)_v(CH=CH)_h(CH_2)_iCH_3$; and $R_4$ of R is —$CH_3$. W is an integer from 0 to 14, u is an integer from 0 to 6, v is an integer from 0 to 6, h is an integer from 0 to 6 and i is an integer from 0 to 6. Preferred compounds occur linoleic acid esters where v, w and h are 1, while u=7 and I=4.

152) The compound described in paragraph 143) above where $R_4$ of R is —$(CH_2)_u(CH=CH)_w(CH_2)_v(CH=CH)_h(CH_2)_iCH_3$; and $R_4$ of $R_1$ is —$CH_3$. W is an integer from 0 to 14, u is an integer from 0 to 6, v is an integer from 0 to 6, h is an integer from 0 to 6 and i is an integer from 0 to 6. Preferred compounds occur linoleic acid esters where v, w and h are 1, while u=7 and I=4.

153) The compound described in paragraph 143) above where $R_4$ of R is —$OCH_2CH_3$; and $R_4$ of $R_1$ is —$NHCH_3$.

154) The compound described in paragraph 143) above where $R_4$ of $R_1$ is —$OCH_2CH_3$; and $R_4$ of R is —$NHCH_3$.

155) The compound described in paragraph 143) above where $R_4$ of R is —$OCH_2CH_3$; and $R_4$ of $R_1$ is —$N(CH_3)_2$.

156) The compound described in paragraph 143) above where $R_4$ of $R_1$ is —$OCH_2CH_3$; and $R_4$ of R is —$N(CH_3)_2$.

157) The compound described in paragraph 143) above where $R_4$ of R is —$SCH_2CH_3$; and $R_4$ of $R_1$ is —$NHCH_3$.

158) The compound described in paragraph 143) above where $R_4$ of $R_1$ is —$SCH_2CH_3$; and $R_4$ of R is —$NHCH_3$.

159) The compound described in paragraph 143) above where $R_4$ of R is —$SCH_2CH_3$; and $R_4$ of $R_1$ is —$N(CH_3)_2$.
160) The compound described in paragraph 143) above where $R_4$ of $R_1$ is —$SCH_2CH_3$; and $R_4$ of R is —$N(CH_3)_2$.
161) The compound described in paragraph 141) above where $R_4$ of R and $R_1$ are both —$OCH_3$.
162) The compound described in paragraph 141) above where $R_4$ of R and $R_1$ are both —$SCH_3$.
163) The compound described in paragraph 141) above where $R_4$ of R and $R_1$ are both —$NHCH_3$.
164) The compound described in paragraph 141) above where $R_4$ of R and $R_1$ are both —$N(CH_3)_2$.
165) The compound described in paragraph 141) above where $R_4$ of R and $R_1$ are both —$(CH_2)_u(CH=CH)_w(CH_2)_vCOOH$ (and salts thereof); W is an integer from 0 to 14, u is an integer from 0 to 6 and v is an integer from 0 to 6.
166) The compound described in paragraph 141) above where $R_4$ of R and $R_1$ are both —$(CH_2)_gNH_2$—HCl or other acid salts. G is an integer from 0 to 14.
167) The compound described in paragraph 141) above where $R_4$ of R and $R_1$ are both —$CH_2CH_3$.
168) The compound described in paragraph 141) above where $R_4$ of R and $R_1$ are both —$(CH_2)_4CH_3$.
169) The compound described in paragraph 141) above where $R_4$ of R and $R_1$ are both R or S or rac $CH_eOH(CH_2)_b(CH_3)_d$, where b is an integer from 0 to 8 and d is an integer from 0 to 1. When both b and d are 0, e=2; d can only be 0 when b is 0.
170) The compound described in paragraph 141) above where $R_4$ of R and $R_1$ are both —$(CH_2)_fCO_2H$ (and salts thereof), in which F is an integer from 1 to 24, where 7 is preferred (azaleic acid).
171) The compound described in paragraph 126) above where R and $R_1$ join to form a 3-substituted 1,2-dithiolane ring; $R_2$ and $R_3$ are hydrogen; X and Y are hydrogen; Z is $OR_0$, wherein $R_0$ is a member of a group consisting of hydrogen and optionally substituted $(C_1–C_{15})$alkyl, arylalkanyl or heteroarylalkyl.
172) The compound described in paragraph 171) above where $R_0$ is hydrogen, methyl, ethyl, propyl, butyl, isopropyl, (2-methyl)-1-propyl (i.e. isobutyl), pentyl, (2,2-dimethyl)-1-propyl (i.e. neo-pentyl), (3-methyl)-1-butyl (i.e. isovaleryl), R or S or rac (1-methyl)-1-butyl, R or S or rac (2-methyl)-1-butyl, R or S or rac (1-methyl)-1-pentyl, R or S or rac (2-methyl)-1-pentyl, R or S or rac (3-methyl)-1-pentyl, (4-methyl)-1-pentyl, and so forth. Preferred $R_0$ derivatives are ethyl and propyl.
173) The compounds described in paragraphs 126) through 171) above where Z=$NHR_0$. Preferred $R_0$ derivatives are ethyl, propyl, 2-(N,N'-dimethylamino)ethyl- (and acid salts thereof), and aryl or heteroaryl rings.
174) The compounds described in paragraphs 126) through 171) above where Z=$SR_0$. Preferred $R_0$ derivatives are ethyl, propyl, 2-(N,N'-dimethylamino)ethyl- (and acid salts thereof), and aryl or heteroaryl rings.
175) The compounds described in paragraphs 126) through 171) above where $R_0$ is an antioxidant such as ascorbic acid (Vitamin C), retinol (Pro-Vitamin A), vitamin E (the various tocopherols and tocophatrienes), vitamin D, hydroquinone, di(t-butylated)hydroxytoluene BHT, t-butylatedhydroxyanisole BHA, t-butylhydroquinone TBHQ, propyl gallate, reduced coenzyme-Q, flavones and isoflavones such as apigenin, quercetin, genistein, and daidzein.
176) The first compound where $R_2$ and $R_3$ join together to form a ring that is either optionally substituted saturated cycloalkyl with a ring size from 3 to 15, or optionally substituted heterocycloalkyl or heterocycloalkenyl of ring size 3 to 15.
177) The second compound where $R_2$ and $R_3$ join together to form a ring that is either optionally substituted saturated cycloalkyl with a ring size from 3 to 15, or optionally substituted heterocycloalkyl or heterocycloalkenyl of ring size 3 to 15.
178) The compound described in paragraph 176) above where X and Y join together to form a ring that is either optionally substituted saturated cycloalkyl with a ring size from 3 to 15, or optionally substituted heterocycloalkyl or heterocycloalkenyl of ring size 3 to 15.
179) The compound described in paragraph 176) above where one of X or Y is H, OH, alkoxyl ($OR_0$), SH, sulife ($SR_0$), $NH_2$, $NHR_0$, $N(R_0)_2$, $SOR_0$, $SO_2R_0$, $PO(OR_0)_2$, $SO_2NHR_0$, $SON(R_0)_2$, COOH, $COOR_0$, $CONHR_0$, $CON(R_0)_2$, in which $R_0$ is optionally substituted saturated alkyl from C1–C15, or optionally substituted heteroalkyl or heteroalkenyl of C1–C15.
180) The compound described in paragraph 177) above where X and Y join together to form a ring that is either optionally substituted saturated cycloalkyl with a ring size from 3 to 15, or optionally substituted heterocycloalkyl or heterocycloalkenyl of ring size 3 to 15.
181) The compound described in paragraph 177) above where one of X or Y is H, OH, alkoxyl ($OR_0$), SH, sulife ($SR_0$), $NH_2$, $NHR_0$, $N(R_0)_2$, $SOR_0$, $SO_2R_0$, $PO(OR_0)_2$, $SO_2NHR_0$, $SON(R_0)_2$, COOH, $COOR_0$, $CONHR_0$, $CON(R_0)_2$, in which $R_0$ is optionally substituted saturated alkyl from C1–C15, or optionally substituted heteroalkyl or heteroalkenyl of C1–C15.
182) The compound described in paragraph 1) above where one of R and $R_1$ are —$CH_2OCOR_4$, and the other is hydrogen; Z is $OR_0$, wherein $R_0$ is a member of a group consisting of hydrogen and optionally substituted $(C_1–C_{15})$alkyl, arylalkanyl or heteroarylalkyl; and $R_4$ is H, heterosubstituted (alcohols, ketones, carboxylates, sulfides, sulfoxides, sulfones, sulfonamides, amines, amides, urethanes, thiourethanes, ureas, carbonates, acetals, ketals, etc.) or unsubstituted normal, branched, cyclic or substituted cyclic hydrocarbons from C1–C20; aryl ring, substituted aryl ring; alkylaryl rings and substituted arylalkyl rings; heterocyclic rings and substituted heterocyclic rings; heteroaromatic rings and substituted heteroaromatic rings; alkylheteroaryl rings and substituted alkylheteroaryl rings. Also contained are $NHR_{19}$, $NR_{19}R_{20}$, $OR_{19}$, $SR_{19}$.
183) The compound described in paragraph 182) above where both of R and $R_1$ are —$CH_2OCOR_4$, wherein $R_4$ can be identical.
184) The compound described in paragraph 183) above where $R_4$ of R and $R_1$ are both —$CH_3$.
185) The compound described in paragraph 182) above where $R_4$ of R is different from the $R_4$ of $R_1$.
186) The compound described in paragraph 185) above where $R_4$ of R is —$(CH_2)_gNH_2$—HCl or other acid salts, G is an integer from 0 to 14; and $R_4$ of $R_1$ is —$CH_3$.
187) The compound described in paragraph 185) above where $R_4$ of R is —$CH_2CH_3$; and $R_4$ of $R_1$ is —$CH_3$.
188) The compound described in paragraph 185) above where $R_4$ of R is —$CH_2(CH_2)_wCOOH$ (and salts thereof); and $R_4$ of $R_1$ is —$CH_3$. W is an integer from 0 to 24. Preferred compounds occur with azaleic acid (w=7).

189) The compound described in paragraph 185) above where $R_4$ of R is —$(CH_2)_u(CH=CH)_w(CH_2)_v(CH=CH)_h(CH_2)_iCOOH$ (and salts thereof); and $R_4$ of $R_1$ is —$CH_3$. W is an integer from 0 to 14, u is an integer from 0 to 6, v is an integer from 0 to 6, h is an integer from 0 to 6 and i is an integer from 0 to 6. Preferred compounds occur when v, w and h are 1.

190) The compound described in paragraph 185) above where $R_4$ of R is —$OCH_2CH_3$; and $R_4$ of $R_1$ is —$NHCH_3$.

191) The compound described in paragraph 185) above where $R_4$ of R is —$OCH_2CH_3$; and $R_4$ of $R_1$ is —$N(CH_3)_2$.

192) The compound described in paragraph 185) above where $R_4$ of R is —$SCH_2CH_3$; and $R_4$ of $R_1$ is —$NHCH_3$.

193) The compound described in paragraph 185) above where $R_4$ of R is —$SCH_2CH_3$; and $R_4$ of $R_1$ is —$N(CH_3)_2$.

194) The compound described in paragraph 183) above where $R_4$ of R and $R_1$ are both —$OCH_3$.

195) The compound described in paragraph 183) above where $R_4$ of R and $R_1$ are both —$SCH_3$.

196) The compound described in paragraph 183) above where $R_4$ of R and $R_1$ are both —$NHCH_3$.

197) The compound described in paragraph 183) above where $R_4$ of R and $R_1$ are both —$N(CH_3)_2$.

198) The compound described in paragraph 183) above where $R_4$ of R and $R_1$ are both —$(CH_2)_u(CH=CH)_w(CH_2)_vCOOH$ (and salts thereof); and $R_4$ of $R_1$ is —$CH_3$. W is an integer from 0 to 14, u is an integer from 0 to 6 and v is an integer from 0 to 6. A preferred example occurs when u and v together equal 7, for azelaic acid.

199) The compound described in paragraph 183) above where $R_4$ of R and $R_1$ are both —$(CH_2)_gNH_2$—HCl or other acid salts. G is an integer from 0 to 14.

200) The compounds described in paragraphs 182), 183) or 185) above where $R_0$ is methyl, ethyl, propyl, butyl, isopropyl, (2-methyl)-1-propyl (i.e. isobutyl), pentyl, (2,2-dimethyl)-1-propyl (i.e. neo-pentyl), (3-methyl)-1-butyl (i.e. isovaleryl), R or S or rac (1-methyl)-1-butyl, R or S or rac (2-methyl)-1-butyl, R or S or rac (1-methyl)-1-pentyl, R or S or rac (2-methyl)-1-pentyl, R or S or rac (3-methyl)-1-pentyl, (4-methyl)-1-pentyl, and so on. Preferred $R_0$ derivatives are ethyl and propyl.

201) The compounds described in paragraphs 182) through 200) where Z=$NHR_0$. Preferred $R_0$ derivatives are ethyl, propyl, 2-(N,N'-dimethylamino)ethyl- (and acid salts thereof), and aryl or heteroaryl rings.

202) The compounds described in paragraphs 182) through 200) where Z=$SR_0$. Preferred $R_0$ derivatives are ethyl, propyl, 2-(N,N'-dimethylamino)ethyl- (and acid salts thereof), and aryl or heteroaryl rings.

203) The compounds described in paragraphs 182) through 200) where $R_0$ is an antioxidant such as ascorbic acid (Vitamin C), retinol (Pro-Vitamin A), vitamin E (the various tocopherols and tocophatrienes), vitamin D, hydroquinone, di(t-butylated)hydroxytoluene BHT, t-butylatedhydroxyanisole BHA, t-butylhydroquinone TBHQ, propyl gallate, reduced coenzyme-Q, flavones and isoflavones such as apigenin, quercetin, genistein, and daidzein.

204) The compound described in paragraph 38) above where one of R and $R_1$ are —$CH_2OCOR_4$, and the other is hydrogen; Z is $OR_0$, wherein $R_0$ is a member of a group consisting of hydrogen and optionally substituted $(C_1-C_{15})$alkyl, arylalkanyl or heteroarylalkyl; and $R_4$ is H, heterosubstituted (alcohols, ketones, carboxylates, sulfides, sulfoxides, sulfones, sulfonamides, amines, amides, urethanes, thiourethanes, ureas, carbonates, acetals, ketals, etc.) or unsubstituted normal, branched, cyclic or substituted cyclic hydrocarbons from C1–C20; aryl ring, substituted aryl ring; alkylaryl rings and substituted arylalkyl rings; heterocyclic rings and substituted heterocyclic rings; heteroaromatic rings and substituted heteroaromatic rings; alkylheteroaryl rings and substituted alkylheteroaryl rings. Also contained are $NHR_{19}$, $NR_{19}R_{20}$, $OR_{19}$, $SR_{19}$.

205) The compound described in paragraph 204) above where both of R and $R_1$ are —$CH_2OCOR_4$, wherein $R_4$ can be identical.

206) The compound described in paragraph 205) above where $R_4$ of R and $R_1$ are both —$CH_3$.

207) The compound described in paragraph 204) above where $R_4$ of R is different from the $R_4$ of $R_1$.

208) The compound described in paragraph 207) above where $R_4$ of R is —$(CH_2)_gNH_2$—HCl or other acid salts, G is an integer from 0 to 14; and $R_4$ of $R_1$ is —$CH_3$.

209) The compound described in paragraph 207) above where $R_4$ of R is —$CH_2CH_3$; and $R_4$ of $R_1$ is —$CH_3$.

210) The compound described in paragraph 207) above where $R_4$ of R is —$CH_2(CH_2)_wCOOH$ (and salts thereof); and $R_4$ of $R_1$ is —$CH_3$. W is an integer from 0 to 24. Preferred compounds occur with azelaic acid (w=7).

211) The compound described in paragraph 207) above where $R_4$ of R is —$(CH_2)_u(CH=CH)_w(CH_2)_v(CH=CH)_h(CH_2)_iCOOH$ (and salts thereof); and $R_4$ of $R_1$ is —$CH_3$. W is an integer from 0 to 14, u is an integer from 0 to 6, v is an integer from 0 to 6, h is an integer from 0 to 6 and i is an integer from 0 to 6. Preferred compounds occur when v, w and h are 1.

212) The compound described in paragraph 207) above where P4 of R is —$OCH_2CH_3$; and $R_4$ of $R_1$ is —$NHCH_3$.

213) The compound described in paragraph 207) above where $R_4$ of R is —$OCH_2CH_3$; and $R_4$ of $R_1$ is —$N(CH_3)_2$.

214) The compound described in paragraph 207) above where $R_4$ of R is —$SCH_2CH_3$; and $R_4$ of R is —$NHCH_3$.

215) The compound described in paragraph 207) above where $R_4$ of R is —$SCH_2CH_3$; and $R_4$ of $R_1$ is —$N(CH_3)_2$.

216) The compound described in paragraph 205) above where $R_4$ of R and $R_1$ are both —$OCH_3$.

217) The compound described in paragraph 205) above where $R_4$ of R and $R_1$ are both —$SCH_3$.

218) The compound described in paragraph 205) above where $R_4$ of R and $R_1$ are both —$NHCH_3$.

219) The compound described in paragraph 205) above where $R_4$ of R and $R_1$ are both —$N(CH_3)_2$.

220) The compound described in paragraph 205) above where $R_4$ of R and $R_1$ are both —$(CH_2)_u(CH=CH)_w(CH_2)_vCOOH$ (and salts thereof); and $R_4$ of $R_1$ is —$CH_3$. W is an integer from 0 to 14, u is an integer from 0 to 6 and v is an integer from 0 to 6. A preferred example occurs when u and v together equal 7, for azelaic acid.

221) The compound described in paragraph 205) above where $R_4$ of R and $R_1$ are both —$(CH_2)_gNH_2$—HCl or other acid salts. G is an integer from 0 to 14.

222) The compound described in paragraphs 204), 205, or 207 above where $R_0$ is methyl, ethyl, propyl, butyl, isopropyl, (2-methyl)-1-propyl (i.e. isobutyl), pentyl, (2,2-dimethyl)-1-propyl (i.e. neo-pentyl), (3-methyl)-1-butyl (i.e. isovaleryl), R or S or rac (1-methyl)-1-butyl, R or S or rac (2-methyl)-1-butyl, R or S or rac (1-methyl)-1-pentyl, R or S or rac (2-methyl)-1-pentyl, R or S or rac (3-methyl)-1-pentyl, (4-methyl)-1-pentyl, and so on. Preferred $R_0$ derivatives are ethyl and propyl.

223) The compound described in paragraphs 204) through 221) above where $Z=NHR_0$. Preferred $R_0$ derivatives are ethyl, propyl, 2-(N,N'-dimethylamino)ethyl- (and acid salts thereof), and aryl or heteroaryl rings.
224) The compound described in paragraphs 204) through 221) above where $Z=SR_0$. Preferred $R_0$ derivatives are ethyl, propyl, 2-(N,N'-dimethylamino)ethyl- (and acid salts thereof), and aryl or heteroaryl rings.
225) The compound described in paragraphs 204) through 221) above where $R_0$ is an antioxidant such as ascorbic acid (Vitamin C), retinol (Pro-Vitamin A), vitamin E (the various tocopherols and tocophatrienes), vitamin D, hydroquinone, di(t-butylated)hydroxytoluene BHT, t-butylatedhydroxyanisole BHA, t-butylhydroquinone TBHQ, propyl gallate, reduced coenzyme-Q, flavones and isoflavones such as apigenin, quercetin, genistein, and daidzein.
226) A compound of the formula

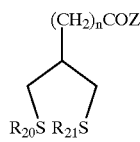

Wherein,
One of $R_{20}$ or $R_{21}$ must be a —NO, or both $R_{20}$ and $R_{21}$ can be —NO.
$R_{20}=$ —NO or —$COR_4$, or —$CH_2OCOR_4$, or —$CH(R_j)OCOR_4$ or H.
$R_{21}=$ —NO or —$COR_4$, or —$CH_2OCOR_4$, or —$CH(R_j)OCOR_4$ or H.
$Z=OH, OR_0, NHR_0, NHOH, NHNR_{22}R_{23}, NHCOR_0, NH(CH_2)_nNR_{24}R_{25}$.
n=0–8.
$R_0$ and $R_{20}$–$R_{27}$=optionally substituted C1–C20 alkyl, aryl, alkylaryl, alkenyl, heterocyclic, heteroaryl and alkylheteroaryl.
Z is $OR_0$, wherein $R_0$ is a member of a group consisting of hydrogen and optionally substituted ($C_1$–$C_{20}$)alkyl, arylalkanyl or heteroarylalkyl and various polyethylene glycol polymers.
$R_4$ is H, heterosubstituted (alcohols, ketones, carboxylates, sulfides, sulfoxides, sulfones, sulfonamides, amines, amides, urethanes, thiourethanes, ureas, carbonates, acetals, ketals, etc.) or unsubstituted normal, branched, cyclic or substituted cyclic hydrocarbons from C1–C20; aryl ring, substituted aryl ring; alkylaryl rings and substituted arylalkyl rings; heterocyclic rings and substituted heterocyclic rings; heteroaromatic rings and substituted heteroaromatic rings;
alkylheteroaryl rings and substituted alkylheteroaryl rings. Also contained are $NHR_{26}$, $NR_{26}R_{27}$, $OR_{26}$, $SR_{26}$.
227) A compound of the formula

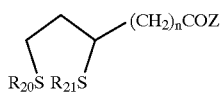

Wherein,
One of $R_{20}$ or $R_{21}$ must be a —NO, or both $R_{20}$ and $R_{21}$ can be —NO.
$R_{20}=$ —NO or —$COR_4$, or —$CH_2OCOR_4$, or —$CH(R_j)OCOR_4$ or H.
$R_{21}=$ —NO or —$COR_4$, or —$CH_2OCOR_4$, or —$CH(R_j)OCOR_4$ or H.
$Z=OH, OR_0, NHR_0, NHOH, NHNR_{22}R_{23}, NHCOR_0, NH(CH_2)_nNR_{24}R_{25}$.
n=0–8.
$R_0$ and $R_{20}$–$R_{27}$ optionally substituted C1–C20 alkyl, aryl, alkylaryl, alkenyl, heterocyclic, heteroaryl and alkylheteroaryl.
Z is $OR_0$, wherein $R_0$ is a member of a group consisting of hydrogen and optionally substituted ($C_1$–$C_{20}$)alkyl, arylalkanyl or heteroarylalkyl and various polyethylene glycol polymers.
$R_4$ is H, heterosubstituted (alcohols, ketones, carboxylates, sulfides, sulfoxides, sulfones, sulfonamides, amines, amides, urethanes, thiourethanes, ureas, carbonates, acetals, ketals, etc.) or unsubstituted normal, branched, cyclic or substituted cyclic hydrocarbons from C1–C20; aryl ring, substituted aryl ring; alkylaryl rings and substituted arylalkyl rings; heterocyclic rings and substituted heterocyclic rings;
heteroaromatic rings and substituted heteroaromatic rings;
alkylheteroaryl rings and substituted alkylheteroaryl rings. Also contained are $NHR_{26}$, $NR_{26}R_{27}$, $OR_{26}$, $SR_{26}$.
228) A compound as described in paragraph 227) above where n is an integer from 0–8, and Z is —$OR_0$, wherein $R_0$ is a member of a group consisting of hydrogen and optionally substituted ($C_1$–$C_{15}$)alkyl, arylalkanyl or heteroarylalkyl.

Example 10

Moisturizing Soap Bar for Sensitive Facial Skin

| Materials | Specific Use Concentration (Wt %) |
|---|---|
| Purified Water | 9.3400 |
| Detergents and Cleansing Agents | 48.2000 |
| Buffering Agents | 2.4800 |
| Humectants and Skin Conditioning Agents | 13.0870 |
| Fragrance | 0.2400 |
| Preservatives | 0.0900 |
| Thickeners and Colorants | 25.6600 |
| Vitamin A Palmitate | 0.0050 |
| Vitamin E Acetate | 0.4900 |
| Magnesium Ascorbyl Phosphate | 0.0040 |
| Beta Glucan | 0.0100 |
| Superoxide Dismutase | 0.0040 |
| Grape Seed Extract | 0.1950 |
| Panthenol | 0.1950 |
| Lipoic acid derivative | 1.0–5.0 |
| Total | 100.0000% |

The above moisturizing facial soap composition provides improved skin feel useful for conditioning desquamating, and cleansing the skin and for relieving dry skin.

All publications, patents and patent applications mentioned in this specification are herein incorporated by reference into the specification in their entirety for all purposes.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

The foregoing is offered primarily for purposes of illustration. It will be readily apparent to those of ordinary skill in the art that the operating conditions, materials, procedural steps and other parameters of the invention described herein may be further modified or substituted in various ways without departing from the spirit and scope of the invention. For example, the invention has been described with human patients as the usual recipient, but veterinary use is also contemplated. Thus, the preceding description of the invention should not be viewed as limiting but as merely exemplary. Instead the true scope of the invention should be determined by the following claims.

TABLE I

Examples of dermatological disorders preventable or treatable using compounds described in this invention Kertinizing skin diseases, keratitis, hidradenitis, ichthyosis
Psoriasis (all forms, including *p. vulgaris, p. guttata, p. discoidea, p. anthropica, p. universalis*)
Acne (all forms, including *a. vulgaris, a. rosacea, a. inversa, cystic acne*)
Warts, verruca (all forms, including common warts, anogenital (venereal) warts, viral warts including human papilloma virus (HPV) infections, conjunctival warts, oral/buccal warts)
Lupus associated skin lesions
Keratoses such as seborrheic keratosis, senile keratosis, actinic keratosis, photo-induced keratosis, skin aging, thinning skin, dry skin, erythema, redness, wrinkle formation, photo-induced skin aging, keratosis follicularis
Keloids and prophylaxis against keloid formation
Scar formation
Leukoplakia, lichen planus
Urticaria, pruritus
Androgenic alopecia in men and women, hirsutism in women

TABLE II

Examples of skin conditions preventable or treatable using compounds described in this invention as cosmetic agents Progressive thinning of the epidermis resulting from age-related depletion and destruction of matrix proteins such as collagen, proteoglycans, elastin and laminin, leading to friable skin.
Ultraviolet radiation-induced expression of matrix metalloproteinases in skin as a result of aging.
Sun-damaged skin, dry skin, chapped skin, wrinkled skin, aging skin, sagging skin, rough skin, weathered skin, inflamed skin, reddened skin, psoriasis, keratitis, hidradenitis, ichthyosis, acne, rosacea, warts, verrucae and related to human papilloma virus infection, atopic dermatitis, allergic dermatitis, chemical (irritant) dermatitis, seborrheic dermatitis, solar dermatitis, acute and chronic eczema, seborrheic keratosis, senile keratosis, actinic keratosis, photo-induced keratosis, skin aging, thinning skin, dry skin, wrinkle formation, photo-induced skin aging, keloids, lichen planus, comprising a compound of this, or a cosmetically acceptable salt thereof.
Acute and chronic dermatitides (inflammation of the skin), atopic dermatitis, allergic dermatitis, contact dermatitis, cosmetic dermatitis, chemical dermatitis, seborrheic dermatitis, solar dermatitis, acute and chronic eczema, diaper rash, sunburn.

TABLE III

Examples of diseases of various organ systems preventable or treatable using compounds described in this invention

| Organ System | Disease/Pathology |
|---|---|
| Cardio-vascular | Hypertension, vasculo-occlusive diseases including atherosclerosis, arteritis, endarteritis, endocarditis, myocarditis, arterial plaque (fibrous cap) rupture. thrombosis, restenosis after any invasive vascular procedures; acute coronary syndromes such as unstable angina, myocardial infarction, myocardial ischemia and other ischemic cardiomyopathies, non-ischemic cardiomyopathies, post-myocardial infarction cardiomyopathy and myocardial fibrosis, drug-induced cardiomyopathy. |
| Endocrine | Obesity, type 1 diabetes mellitus, type 2 diabetes mellitus, gestational diabetes, impaired glucose tolerance, Cushing's syndrome (e.g. secondary to chronic glucocorticoid therapy), polycystic ovarian syndrome, osteoporosis, osteopenia, accelerated aging of tissues and organs, e.g. Werner's syndrome. |
| Urogenital | Prostatitis, endometritis, endometriosis, benign prostatic hypertrophy, leiomyoma, polycystic kidney disease (e.g. autosomal dominant PKD), acute tubular necrosis, nephrotic syndrome, diabetic nephropathy, glomerulonephritis. Erectile (corpus cavernosum) dysfunction in men, erectile (clitoral) dysfunctional in women |
| Pulmonary | Asthma, chronic obstructive pulmonary disease (COPD), reactive airway disease, pulmonary fibrosis, pulmonary hypertension. |
| Connective tissue Joint | Rheumatoid arthritis, Raynaud's phenomenon/disease, Siogren's syndrome, systemic sclerosis, systemic lupus erythematosus, inflammatory bowel disease (ulcerative colitis, Crohn's disease) vasculitides, ankylosing spondylitis, osteoarthritis, reactive arthritis, psoriatic arthritis, fibromyalgia, osteoarthritis, sarcoidosis. |
| Liver/Other | Hepatic fibrosis, hepatic cirrhosis, hepatic steatosis, all etiologies, e.g. alcohol-induced (e.g. ethanol), drug-induced (e.g. tylenol), and toxin-induced (e.g. mushroom poisoning) Fibrocystic breast disease, fibroadenoma |
| Neurologic/psychiatric | Migraine headaches, vascular headaches, Alzheimer's disease, and secondary (e.g. HIV-related) dementias, degenerative CNS diseases (e.g. Parkinson's disease, amyotropic lateral sclerosis, multiple sclerosis, Guillain-Barre; Pain disorders including algesia, hyperalgesia, acute and chronic pain, allodynia; Primary and secondary encephalitis and encephalomyelitis (e.g. autoimmune encephalomyclitis, allergic encephalomyelitis); Primary and secondary neuritis, autoimmune neuritis Other autoimmune diseases (e.g. myesthenia gravis, Eaton-Lambert syndrome), congenital and secondary ataxias |

TABLE IV

Examples of viral infections and related pathologies preventable or treatable according to the methods of this invention

| Virus | Viral infection/cancer or other virus-associated pathology |
|---|---|
| HPV | Cervical and anogenital cancers; common and anogenital (venereal) warts, including verrucae, condyloma or condyloma acuminata, related non-neoplastic (e.g., keratitis, conjunctivitis) pre-neoplastic and neoplastic (e.g., conjunctival epithelial neoplasms) diseases of the eye. |
| HAV, HBV, HCV | Hepatitis, hepatocellular carcinoma, lymphoma. |
| CMV | Hepatitis, retinitis, meningitis. |
| HSV, VSV | Related mucocutaneous, oropharyngeal and genital diseases, related skin and respiratory infections, varicella-zoster, chicken pox, herpes zoster, post-herpetic neuralgia, conjunctivitis, keratoconjunctivitis, keratitis. |

TABLE IV-continued

Examples of viral infections and related pathologies preventable or treatable according to the methods of this invention

| Virus | Viral infection/cancer or other virus-associated pathology |
|---|---|
| HHV | Exanthem subitum, infectious mononucleosis. |
| EBV | Infectious mononucleosis, chronic fatigue syndrome, lymphoma, conjunctivitis, keratitis, and related eye infections. |
| Adeno-viruses | Upper and lower respiratory tract infections, pneumonia, conjunctivitis. |
| RSV | Upper and lower respiratory tract infections, pneumonia. |
| PMV | Mumps and related manifestations, e.g, conjunctivitis. |
| MV, RV | Measles, Rubella ("German measles") and related manifestations. |
| Coxsackie viruses | Conjunctivitis, diabetes mellitus, respiratory infections. |
| Influenza viruses | Upper and lower respiratory tract infections, pneumonia. |

HIV, Human Immunodeficiency Virus; HPV, Human Papilloma Virus; HAV, Hepatitis A Virus; HBV, Hepatitis B Virus; HAV, Hepatitis C Virus; CMV, Cytomegalovirus; HSV, Herpes Simplex Virus (Types I & II); HHV, Human Herpes Virus; EBV, Epstein-Barr Virus; RSV, Respiratory Syncytial Virus; VZV, Varicella-Zoster Virus; PMV, Paramyxovirus; MV, Measles (Rubeola) Virus; RV, Rubella Virus

TABLE V

HIV related infections and diseases preventable or treatable using compounds described in this invention

| Organ system | Viral infection/manifestation or other HIV-associated disease |
|---|---|
| Immunologic | AIDS, primary HIV infection. |
| Dermatological | Anogenital cancers including rectal and cervical cancer, Kaposi's sarcoma, atopic dermatitis, squamous cell carcinoma, hairy leukoplakia, molluscum contagiosum, warts (HPV infections), seborrheic dermatitis, psoriasis, xeroderma, HSV and varicella-zoster infections. |
| Hematologic | Non-Hodgkin's lymphoma, B cell lymphoma, anemia, neutropenia, thrombocytopenia. |
| Gastro-intestinal | Anorexia, gastroparesis, diarrhea, malabsorption, gastrointestinal CMV infections, esophagitis, colitis, hepatitis, lymphoma. |
| Ophthalmic | Conjunctivitis, keratitis, keratoconjunctivitis, uveitis, retinitis, chorioretinitis, CMV retinitis, iridocyclitis, vitreitis, choroiditis, papilledema, Kaposi's sarcoma, lymphoma, ocular palsies, conjunctival warts, pre-neoplastic and neoplastic diseases of the eye. |
| Cardiac | Myocarditis, endocarditis, pericarditis. |
| Pulmonary | CMV pneumonitis, lymphoid interstitial pneumonitis. |
| Nephrologic | HIV nephropathy, renal cell carcinoma, amyloidosis, uropathy. |
| Rheumatologic | Arthralgia, fibromyalgia, Reiter's syndrome, psoriatic arthritis, vasculitis. |
| Neurologic | Dementia, viral meningitis, viral encephalitis, HIV encephalopathy, progressive multifocal leukoencephalopathy, CNS lymphoma, peripheral and autonomic neuropathies. |
| Psychiatric | Dysphoric mood disorders, depression, depression associated with chronic diseases and medications, bipolar disorder, anxiety disorders, chronic fatigue syndrome, chronic pain, psychoses, substance abuse disorders and drug addiction. |
| Urogenital/sexual dysfunction | Sexual dysfunction and failure to achieve orgasm in men and women, erectile dysfunction, failure to achieve penile tumescence in men, sexual dysfunction and impaired engorgement of clitoris, labia and corpus corpora in women, dyspareunia and vaginismus in women. |

TABLE VI

Diseases of the eye preventable or treatable using compounds described in this invention
Disease Category/Examples of Diseases, Causes or Associated Conditions*

| | |
|---|---|
| Conjunctivitis | Acute allergic conjunctivitis (e.g. drug-related inflammation, hypersensitivity reactions), chronic (vernal) conjunctivitis, contact lens-associated conjunctivitis, e.g. giant papillary conjunctivitis, conjunctival ulceration, including ulceration associated with mucous membrane, conjunctival warts, follicular, hemorrhagic or catarrhal conjunctivitis, viral conjunctivitis - all viral etiologies. |
| Blepharitis | Inflammatory etiologies, e.g. blepharitis secondary to rosacea. |
| Keratitis | All etiologies |
| Keratoconjunctivitis | All etiologies |
| Ophthalmic fibrosis | Steven's-Johnson syndrome with progressive fibrosis and scarring, cicatrization and symblepharon. |
| Corneal injury | Corneal abrasion or ulceration (e.g. contact lens-related injury), or corneal injury of any etiology*. |
| Dry eye syndrome | See Table below |
| Pterygium, pinguecula | |
| Pemphigoid | Includes ophthalmic pemhigori |
| Scleritis/Episcleritis | |
| Iridocyclitis | |
| Endophthalmitis | |
| Uveal tract diseases | Including glaucoma (primary and secondary etiologies) Uveitis, uveoretinitis, panuveitis, all etiologies* |
| Vitreitis, retinitis | Congenital retinitis, retinitis pigmentosa |
| Infectious retinitis | Viral (e.g. herpes, cytomegalovirus, liv), tuberculous, syphititic, fungal (e.g. histoplasmosis) |
| Chorioretinopathies | Chorioretinitis, choroiditis, vitreitis, |
| Retinopathies | Diabetic retinopathy, hypertensive retinopathy |
| Maculopathies | Age-related-macular degeneration, white dot syndromes |

TABLE VI-continued

Diseases of the eye preventable or treatable using compounds described in this invention
Disease Category/Examples of Diseases, Causes or Associated Conditions*

Cataract                    Related to aging, diabetes, collagen vascular diseases
Ocular palsies

*Etiologies of ophthalmic diseases treatable according to the methods of this invention include diseases induced or caused by physical agents (e.g UV radiation), chemical agents (e.g. acids, caustic solvents) immunological etiologies (e.g. collagen vascular diseases, auto-immune, T lymphocyte-related), infectious agents such as viruses (HSV, CMV HIV), mycoplasma, tuberculosis, syphilis, fungae (histoplasmosis)

TABLE VII

Ophthalmic diseases preventable or treatable using compounds described in this invention Dry Eye Syndrome
1. Hypofunction of the lacrimal gland as in, e.g. Sjögren's Syndrome, progressive systemic sclerosis, sarcoidosis, leukemia, lymphyoma, amyloidosis, hemochromatosis; Infection, e.g. mumps; Injury, e.g. surgical removal of lacrimal gland, irradiation, chemical burn; Medications, e.g. antihistamines, antimuscarinics, general anesthetics, β-adrenergic blockers; Congenital causes; Neurogenic, e.g. facial nerve palsy.
2. Avitaminosis A, Stevens-Johnson syndrome, ocular pemphigoid, chronic conjuncitivitis (e.g. trachoma), chemical burns, drugs and medications
3. Defective Spreading of Team Film Caused by: eyelid abnormalities, including defects, colboma; ectropion or entropion, keratinization of lid margin, decreased or absent blinking secondary to: neurologic disorders, hyperthyroidism, contact lens, drugs and medications, herpes simplex keratitis, leprosy, conjunctival abnormalities, pterygium, symblepharon, proptosis
Macular disorders: All etiologies and manifestations, including age-related macular degeneration, exudative macular degeneration, atrophic macular degeneration, crystalline retinopathies, retinal toxicosis of systemic medications, idiopathic central serous choroidiopathy, macular edema
Retinovascular diseases and retinopathies: Retinopathy, vasculo-occlusive r., ischemic r., idiopathic r., hypertensive r., proliferative r., diabetic r., vitreoretinopathy, vasculopathies associated with telangiectasias or aneurysms, retinopathies associated with lupus erythematosus, rheumatoid arthritis, multiple sclerosis, myasthenia gravis, uveoretinitis or diabetes mellitus, glaucomatous retinopathies
Glaucoma: All etiologies and manifestations, including primary and secondary open-angle glaucoma, angle-closure glaucoma, glaucoma associated with intraocular inflammation, elevated intraocular pressure associated with acute glaucoma, steroid-induced glaucoma, glaucoma associated with intraocular hemorrhage, pseudoexfoliative syndrome, glaucomatous optic neuropathy and other degenerative changes (e.g. retinopathy) associated with glaucoma
Cataract: All etiologies and manifestations, including age-related (UV radiation) cataract, cataract associated with systemic diseases such as collagen vascular disease, diabetes metlitus, Wilson's disease
Other diseases: Primary or secondary retinal detachment

TABLE VIII

Ophthalmic diseases preventable or treatable using compounds described in this invention - Congenital degenerative retinopathies I. Primary pigmented retinopathies, all gene types Autosomal dominant retinitis pigmentosa
  Autosomal recessive retinitis pigmentosa
  X-linked recessive pigmented retinopathies, e.g. choroideremia
2. Secondary pigmented retinopathies (retinopathies associated with systemic diseases)

Autosomal dominant pigmented retinopathies, e.g. Paget's disease, Charcot-Marie-Tooth, disease, Steinert's disease, Pierre-Marie syndrome
  Autosomal recessive pigmented retinopathies, e.g. diabetes mellitus, mannosidoses, mucopolysccharidoses, Batten's d., Refsum's d., Usher syndrome
  X-linked recessive pigmented retinopathies, e.g. Hunter syndrome

TABLE IX

Diseases or conditions treatable using compounds described in this invention

I. Promote healing in the following clinical situations:

Surgical or traumatic wounds to healthy tissues or organs
Wounds caused by chemical or physical agents, e.g. ulcers caused by caustic or erosive chemicals, pressure sores, etc.
Wounds associated with disease states, e.g. diabetic ulcers etc.
Wounds in diseased tissues or organs
II. Promote cell survival and prevent apoytosis in neurodegenerative diseases:

Alzheimer's disease
Parkinson's disease
Amyotrophic lateral sclerosis
Spinal cord injury or transection secondary to trauma or disease
III. Attenuation or arrest of the following conditions or processes:

The natural aging of cells and tissues
Aging induced by chemical or physical agents, e.g. sun-induced skin aging

TABLE IX-continued

Diseases or conditions treatable using compounds described in this invention

Accelerated aging associated with diseases, e.g. Werner's syndrome
IV. Vitalization and revitalization of organs and tissues Promoting cell growth and preventing cell death in the aging process
Promoting therapeutic or non-pathological angiogenesis as a therapeutic approach to treating diseases such as congestive heart failure and cardiomyopathy
Promoting growth of organs and tissues for repair or transplantation All of the documents referred to herein are incorporated by reference as if reproduced in full below.

Methods claimed in this invention, in part, applies to lipoic acid, its structural modifications and its uses, as described in detail in the following patent applications:

1. U.S. Pat. No. 6,149,925 Mammone et al: Topical compositions for enhancing glutathione production
2. U.S. Pat. No. 6,180,133 Quan et al: Antioxidant composition for topicautransdermal prevention and treatment of wrinkles
3. U.S. Pat. No. 6,180,133 McAtee et al: Antioxidant composition for topical/transdermal prevention and treatment of wrinkles
4. U.S. Pat. No. 6,197,340 Byrd et al: Controlled release lipoic acid
5. U.S. Pat. No. 6,153,204 Fanger et al: Cosmetic or pharmaceutical preparations with a reduced feeling of stickiness
6. U.S. Pat. No. 6,130,254 Fisher et al: Methods for inhibiting photoaging of skin
7. U.S. Pat. No. 6,090,842 Packer et al: Lipoic acid analogs
8. U.S. Pat. No. 5,948,810 Wessel et al: Use of R-(+)-.alpha.-lipoic acid, R-(−)-dihydrolipoic acid and metabolites in the form of the free acid or as salts or esters or amides for the preparation of drugs for the treatment of diabetes mellitus as well as of its sequelae
9. U.S. Pat. No. 5,728,735 Ulrich et al: Pharmaceutical composition containing R-alpha.-lipoic acid or S-alpha.-lipoic acid as active ingredient
10. U.S. Pat. No. 5,607,980 McAtee et al: Topical compositions having improved skin feel
11. U.S. Pat. No. 5,709,868 Perricone: Lipoic acid in topical compositions
12. U.S. Pat. No. 5,411,991 Shander et al: Method of reducing hair growth employing sulfhydryl active compounds
13. U.S. Pat. No. 5,965,618 Perricone: Treatment of scar tissue using lipoic acid
14. U.S. Pat. No. 5,648,393 Treatment of male impotence with s-nitrosylated compounds
15. U.S. Pat. No. 5,574,068 S-nitrosothiols as smooth muscle relaxants and therapeutic uses thereof
16. U.S. Pat. No. 5,380,758 S-nitrosothiols as smooth muscle relaxants and therapeutic uses thereof While the above is a description of various embodiments of the present invention, further modifications may be employed without departing from the spirit and scope of the present invention. For example, the size, shape, and/or material of the various components may be changed as desired. Thus the scope of the invention should not be limited by the specific structures disclosed. Instead the true scope of the invention should be determined by the following claims.

What is claimed is:
1. A compound having the formula

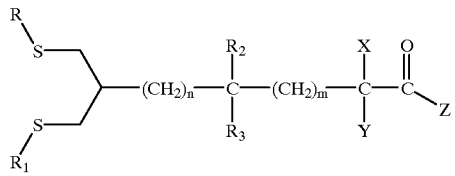

wherein R and $R_1$ are defined according to criteria selected from the group consisting of:
(1) R and $R_1$ are both attached to the same carbonyl group to form a 1,3-dithian-2-one ring;
(2) R and $R_1$ are both attached to the same carbon atom to form a 1,3-dithiane ring;
(3) With the exception that R and $R_1$ together are not H, R and $R_1$ are separately selected from a group consisting of:
H, an acyl group —$COR_4$, —$CH_2OCOR_4$, $CH(R_j)OCOR_4$; and each of $R_2$, $R_3$ and $R_4$ is separately selected from the group consisting of:
H; an optionally substituted alkyl; a branched alkyl; a cycloalkyl; a bicycloalkyl; a tricycloalkyl; a bicycloalkenyl; a tricycloalkenyl; an alkenyl; an allenyl; a cycloalkenyl; an alkylcycloalkyl; an alkylcycloalkenyl; an alkynyl; an aryl; an arylmethylenyl; an arylethylenyl; a heteroalkyl; a heterocyclic; a heteroaromatic; an alkylheterocyclic; an alkylheteroaryl; an alcohol; an ether $OR_5$; a mono-, di-, or unsubstituted amine ($NR_6R_7$); an ester ($COOR_8$); an aldehyde; a formate; a formamide ($NR_0CHO$); a mono-, di-, or unsubsituted amide ($CONR_9R_{10}$); a ketone ($COR_{11}$); an acyl ester ($OCOR_{12}$); an acyl carbonate ($OCOOR_{13}$); an acyl carbamate ($OCONR_{14}R_{15}$); an acyl urea ($NR_{16}CONR_{17}R_{18}$); a halide; a nitro; a nitroso; a hydrazide ($R_{19}NNR_{20}R_{21}$); an acyl hydrazide ($R_{22}CONR_{23}NR_{24}R_{25}$); a diacyl hydrazide ($R_{26}CONR_{27}NR_{28}COR_{29}$); a sulfide ($R_{30}S$—); a sulfoxide ($R_{31}SO$); a sulfone ($R_{32}SO_2$—); a sulfonamide ($R_{33}R_{34}NSO_2$—); a sulfonamidyl ($R_{35}NSO_2R_{36}$); a disulfide ($R_{37}SS$—); an acyl thioyl ($R_{38}COS$—); a thioyl carbonate ($R_{39}OCOS$—); a thioyl carbamate ($R_{40}R_{41}NCOS$—); a dithioester (—$CSSR_{42}$); a thiocarbonate (—$SCSSR_{43}$); an amidinyl ($R_{44}R_{45}C$—$C(=NH)NH_2$); a guanidinyl ($R_{46}N$—$C(=NH)NH_2$); an oxime ($R_{47}C=NOR_{48}$); a hydrazide ($R_{49}C=N$—$NR_{50}R_{51}$); an acyl hydrazide ($R_{52}C=N$—$NR_{53}COR_{54}$); an antioxidant molecule linked through an ester or other carbonyl bond; and $R_j$ is defined according to criteria selected from the group consisting of:
(1) $R_j$ is selected from the group consisting of:
H; an optionally substituted alkyl; a branched alkyl; a cycloalkyl; a bicycloalkyl; a tricycloalkyl; a bicycloalkenyl; a tricycloalkenyl; an alkenyl; an allenyl; a cycloalkenyl; an alkylcycloalkyl; an alkylcycloalkenyl; an alkynyl; an aryl; an arylmethylenyl; an arylethylenyl; a heteroalkyl; a heterocyclic; a heteroaromatic; an alkylheterocyclic; an alkylheteroaryl; an ether ($OR_5$); a di-substituted amine ($NR_6R_7$); an ester ($COOR_8$); an aldehyde; a mono-, di- or unsubstituted amide (CONR$_9$R$_{10}$); a ketone (COR$_{11}$); a sulfide (R$_{30}$S—); a sulfoxide (R$_{31}$SO—); and a sulfone (R$_{32}$SO$_2$—); or (2) R$_j$ comprises a functional group separated from the R$_j$ bearing C atom by at least one additional C atom wherein said functional group is selected from the group consisting of; a mono-, or unsubstituted amine (NR$_6$R$_7$); a formate; formamide (NR$_0$CHO); an acyl ester (OCOR$_{12}$); an acyl carbonate (OCOOR$_{13}$); an acyl carbamate (OCONR$_{14}$R$_{15}$); an acyl urea (NR$_{16}$CONR$_{17}$R$_{18}$); a halide; a nitro; a nitroso; a hydrazide (R$_{19}$NNR$_{20}$R$_{21}$); an acyl hydrazide (R$_{22}$CONR$_{23}$NR$_{24}$R$_{25}$); a diacyl hydrazide (R$_{26}$CONR$_{27}$NR$_{28}$COR$_{29}$); a sulfonamide (R$_{33}$R$_{34}$NSO$_2$—); a sulfonamidyl (R$_{35}$NSO$_2$R$_{36}$); a disulfide (R$_{37}$SS—); an acyl thioyl (R$_{38}$COS—); a thioyl carbonate (R$_{39}$OCOS—); a thioyl carbamate (R$_{40}$R$_{41}$NCOS—); a dithioester (—CSSR$_{42}$); a thiocarbonate (—SCSSR$_{43}$); an amidinyl (R$_{44}$R$_{45}$C—C(=NH)NH$_2$); a guanidinyl (R$_{46}$N—C(=NH)NH$_2$); an oxime (R$_{47}$C=NOR$_{48}$); a hydrazide (R$_{49}$C=N—NR$_{50}$R$_{51}$); an acyl hydrazide (R$_{52}$C=N—NR$_{53}$COR$_{54}$); an antioxidant molecule linked through an ester or other carbonyl bond; and n=0–8; and m=0–8; and X is selected from the group consisting of:
H, OH, R$_{55}$, —OR$_{56}$, —SR$_{57}$, —NR$_{58}$R$_{59}$, —PO(OR$_{60}$)$_2$, —SOR$_{61}$, —SO$_2$R$_{62}$, —SO$_2$NR$_{63}$R$_{64}$, COOH; COOR$_{65}$; CONR$_{66}$R$_{67}$, F, Cl, Br, a substituted aryl, an unsubstituted aryl, a heteroaryl, an arylalkyl, an alkylheteroaryl, a heterocyclic, a saturated ring, and an unsaturated ring; and Y is selected from the group consisting of:
H, OH, R$_{68}$, —OR$_{69}$, —SR$_{70}$, —NR$_{71}$R$_{72}$, —PO(OR$_{73}$)$_2$; —SOR$_{74}$, —SO$_2$R$_{75}$, —SO$_2$NR$_{76}$R$_{77}$, COOH; COOR$_{78}$; CONR$_{79}$R$_{80}$, F, Cl, Br, a substituted aryl, an unsubstituted aryl, a heteroaryl, an arylalkyl, an alkylheteroaryl, a heterocyclic, a saturated ring, and an unsaturated ring; and Z is selected from the group consisting of:
H, OH, OR$_{81}$, NHOH, NH$_{82}$, NHR$_{83}$, NR$_{84}$R$_{85}$, SR$_{86}$; a normal or branched hydrocarbon from C1–C20, an aryl ring, a substituted aryl ring; an alkylaryl ring, a substituted arylalkyl rings; a heterocyclic ring, a substituted heterocyclic ring; a heteroaromatic ring, a substituted heteroaromatic ring; an alkylheteroaryl ring, a substituted alkylheteroaryl rings; an antioxidant molecule linked through an ester or other carbonyl bond; and R$_0$ and each of R$_5$–R$_{86}$ is separately selected from the group consisting of:
H, an alkyl, a branched alkyl, a cycloalkyl, a bicycloalkyl, a bicycloalkenyl, an alkenyl, an allenyl, a cycloalkenyl, an alkylcycloalkyl, an alkylcycloalkenyl, an alkynyl, an aryl, an arylmethylenyl, an arylethylenyl, a heteroalkyl, a heterocyclic, a heteroaromatic, an alkylheterocyclic, and an alkylheteroaryl;

Or a pharmaceutically acceptable salt thereof.

2. A compound having the formula

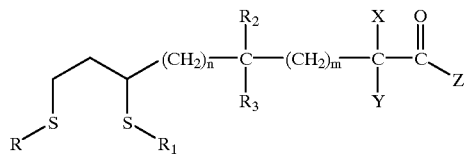

wherein R and R$_1$ are defined according to criteria selected from the group consisting of:
(1) R and R$_1$ are both attached to the same carbonyl group to form a 1,3-dithian-2-one ring;
(2) R and R$_1$ are both attached to the same carbon atom to form a 1,3-dithiane ring;
(3) With the exception that R and R$_1$ together are not H, R and R$_1$ are separately selected from a group consisting of:
H, an acyl group —COR$_4$, —CH$_2$OCOR$_4$, CH(R$_j$)OCOR$_4$; and each of R$_2$, R$_3$ and R$_4$ is separately selected from the group consisting of:
H; an optionally substituted alkyl; a branched alkyl; a cycloalkyl; a bicycloalkyl; a tricycloalkyl; a bicycloalkenyl; a tricycloalkenyl; an alkenyl; an allenyl; a cycloalkenyl; an alkylcycloalkyl; an alkylcycloalkenyl; an alkynyl; an aryl; an arylmethylenyl; an arylethylenyl; a heteroalkyl; a heterocyclic; a heteroaromatic; an alkylheterocyclic; an alkylheteroaryl; an alcohol; an ether OR$_5$; a mono-, di-, or unsubstituted amine (NR$_6$R$_7$); an ester (COOR$_8$); an aldehyde; a formate; a formamide (NR$_0$CHO); a mono-, di-, or unsubstituted amide (CONR$_9$R$_{10}$); a ketone (COR$_{11}$); an acyl ester (OCOR$_{12}$); an acyl carbonate (OCOOR$_{13}$); an acyl carbamate (OCONR$_{14}$R$_{15}$); an acyl urea (NR$_{16}$CONR$_{17}$R$_{18}$); a halide; a nitro; a nitroso; a hydrazide (R$_{19}$NNR$_{20}$R$_{21}$); an acyl hydrazide (R$_{22}$CONR$_{23}$NR$_{24}$R$_{25}$); a diacyl hydrazide (R$_{26}$CONR$_{27}$NR$_{28}$COR$_{29}$); a sulfide (R$_{30}$S—); a sulfoxide (R$_{31}$SO—); a sulfone (R$_{32}$SO$_2$—); a sulfonamide (R$_{33}$R$_{34}$NSO$_2$—); a sulfonamidyl (R$_{35}$NSO$_2$R$_{36}$); a disulfide (R$_{37}$SS—); an acyl thioyl (R$_{38}$COS—); a thioyl carbonate (R$_{39}$OCOS—); a thioyl carbamate (R$_{40}$R$_{41}$NCOS—); a dithioester (—CSSR$_{42}$); a thiocarbonate (—SCSSR$_{43}$); an amidinyl (R$_{44}$R$_{45}$C—C(=NH)NH$_2$); a guanidinyl (R$_{46}$N—C(=NH)NH$_2$); an oxime (R$_{47}$C=NOR$_{48}$); a hydrazide (R$_{49}$C=N—NR$_{50}$R$_{51}$); an acyl hydrazide (R$_{52}$C=N—NR$_{53}$COR$_{54}$); an antioxidant molecule linked through an ester or other carbonyl bond; and R$_j$ is defined according to criteria selected from the group consisting of:
(1) R$_j$ is selected from the group consisting of:
H; an optionally substituted alkyl; a branched alkyl; a cycloalkyl; a bicycloalkyl; a tricycloalkyl; a bicycloalkenyl; a tricycloalkenyl; an alkenyl; an allenyl; a cycloalkenyl; an alkylcycloalkyl; an alkylcycloalkenyl; an alkynyl; an aryl; an arylmethylenyl; an arylethylenyl; a heteroalkyl; a heterocyclic; a heteroaromatic; an alkylheterocyclic; an alkylheteroaryl; an ether (OR$_5$); a di-substituted amine (NR$_6$R$_7$); an ester (COOR$_8$); an aldehyde; a mono-, di- or unsubstituted amide (CONR$_9$R$_{10}$); a ketone (COR$_{11}$); a sulfide ($R_{30}S-$); a sulfoxide ($R_{31}SO-$); and a sulfone ($R_{32}SO_2-$); or (2) $R_j$ comprises a functional group separated from the $R_j$ bearing C atom by at least one additional C atom wherein said functional group is selected from the group consisting of a mono-, or unsubstituted amine ($NR_6R_7$); a formate; formamide ($NR_0CHO$); an acyl ester ($OCOR_{12}$); an acyl carbonate ($OCOOR_{13}$); an acyl carbamate ($OCONR_{14}R_{15}$); an acyl urea ($NR_{16}CONR_{17}R_{18}$); a halide; a nitro; a nitroso; a hydrazide ($R_{19}NNR_{20}R_{21}$); an acyl hydrazide ($R_{22}CONR_{23}NR_{24}R_{25}$); a diacyl hydrazide ($R_{26}CONR_{27}NR_{28}COR_{29}$); a sulfonamide ($R_{33}R_{34}NSO_2-$); a sulfonamidyl ($R_{35}NSO_2R_{36}$); a disulfide ($R_{37}SS-$); an acyl thioyl ($R_{38}COS-$); a thioyl carbonate ($R_{39}OCOS-$); a thioyl carbamate ($R_{40}R_{41}NCOS-$); a dithioester ($-CSSR_{42}$); a thiocarbonate ($-SCSSR_{43}$); an amidinyl ($R_{44}R_{45}C-C(=NH)NH_2$); a guanidinyl ($R_{46}N-C(=NH)NH_2$); an oxime ($R_{47}C=NOR_{48}$); a hydrazide ($R_{49}C=N-NR_{50}R_{51}$); an acyl hydrazide ($R_{52}C=N-NR_{53}COR_{54}$); an antioxidant molecule linked through an ester or other carbonyl bond; and n=0–8; and
m=0–8; and X is selected from the group consisting of:
H, OH, $R_{55}$, $-OR_{56}$, $-SR_{57}$, $-NR_{58}R_{59}$, $-PO(OR_{60})_2$, $-SOR_{61}$, $-SO_2R_{62}$, $-SO_2NR_{63}R_{64}$, COOH; $COOR_{65}$; $CONR_{66}R_{67}$, F, Cl, Br, a substituted aryl, an unsubstituted aryl, a heteroaryl, an arylalkyl, an alkylheteroaryl, a heterocyclic, a saturated ring, and an unsaturated ring; and Y is selected from the group consisting of:
H, OH, $R_{68}$, $-OR_{69}$, $-SR_{70}$, $-NR_{71}R_{72}$, $-PO(OR_{73})_2$; $-SOR_{74}$, $-SO_2R_{75}$, $-SO_2NR_{76}R_{77}$, COOH; $COOR_{78}$; $CONR_{79}R_{80}$, F, Cl, Br, a substituted aryl, an unsubstituted aryl, a heteroaryl, an arylalkyl, an alkylheteroaryl, a heterocyclic, a saturated ring, and an unsaturated ring; and Z is selected from the group consisting of:
H, OH, $OR_{81}$, NHOH, $NH_{82}$, $NHR_{83}$, $NR_{84}R_{85}$, $SR_{86}$; a normal or branched hydrocarbon from C1–C20, an aryl ring, a substituted aryl ring; an alkylaryl ring, a substituted arylalkyl rings; a heterocyclic ring, a substituted heterocyclic ring; a heteroaromatic ring, a substituted heteroaromatic ring; an alkylheteroaryl ring, a substituted alkylheteroaryl rings; an antioxidant molecule linked through an ester or other carbonyl bond; and $R_0$ and each of $R_5$–$R_{86}$ is separately selected from the group consisting of:
H, an alkyl, a branched alkyl, a cycloalkyl, a bicycloalkyl, a bicycloalkenyl, an alkenyl, an allenyl, a cycloalkenyl, an alkylcycloalkyl, an alkylcycloalkenyl, an alkynyl, an aryl, an arylmethylenyl, an arylethylenyl, a heteroalkyl, a heterocyclic, a heteroaromatic, an alkylheterocyclic, and an alkylheteroaryl;

Or a pharmaceutically acceptable salt thereof.

3. A compound in accordance with claim 1, wherein:
n is an integer from 1–6, and m is an integer from 1–6, $R_2$, $R_3$, X, and Y are hydrogen atoms, and Z is $-OR_0$, wherein $R_0$ is a member of a group consisting of hydrogen and optionally substituted ($C_1$–$C_{15}$)alkyl, arylalkanyl or heteroarylalkyl.

4. A compound in accordance with claim 2, wherein:
n is an integer from 1–6, and m is an integer from 1–6, $R_2$, $R_3$, X, and Y are hydrogen atoms, and Z is $-OR_0$, wherein $R_0$ is a member of a group consisting of hydrogen and optionally substituted ($C_1$–$C_{15}$)alkyl, arylalkanyl or heteroarylalkyl.

5. A compound in accordance with claim 3 wherein $R_0$ is an antioxidant selected from the group consisting of ascorbic acid (Vitamin C), retinol (Pro-Vitamin A), vitamin E (the various tocopherols and tocophatrienes), vitamin D, hydroquinone, di(t-butylated)hydroxytoluene BHT, t-butylatedhydroxyanisole BHA, t-butylhydroquinone TBHQ, propyl gallate, reduced coenzyme-Q, flavones and isoflavones such as apigenin, quercetin, genistein, and daidzein.

* * * * *